(12) United States Patent
Bernstein et al.

(10) Patent No.: US 8,466,159 B2
(45) Date of Patent: *Jun. 18, 2013

(54) METHODS FOR TREATING HCV

(75) Inventors: Barry M. Bernstein, Mequon, WI (US);
Rajeev M. Menon, Buffalo Grove, IL (US); Amit Khatri, Waukegan, IL (US);
Sven Mensing, Mannheim (DE);
Sandeep Dutta, Gurnee, IL (US);
Daniel E. Cohen, Wilmette, IL (US);
Thomas J. Podsadecki, Chicago, IL (US); Scott C. Brun, Green Oaks, IL (US); Walid M. Awni, Green Oaks, IL (US); Emily O. Dumas, Libertyville, IL (US); Cheri E. Klein, Northbrook, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/603,022

(22) Filed: Sep. 4, 2012

(65) Prior Publication Data

US 2013/0102525 A1    Apr. 25, 2013

Related U.S. Application Data

(60) Provisional application No. 61/550,352, filed on Oct. 21, 2011, provisional application No. 61/562,181, filed on Nov. 21, 2011, provisional application No. 61/587,225, filed on Jan. 17, 2012, provisional application No. 61/600,276, filed on Feb. 17, 2012, provisional application No. 61/619,870, filed on Apr. 3, 2012, provisional application No. 61/656,251, filed on Jun. 6, 2012.

(51) Int. Cl.
| | | |
|---|---|---|
| A61K 31/4965 | (2006.01) | |
| A61K 31/33 | (2006.01) | |
| A61K 31/505 | (2006.01) | |
| A61K 31/47 | (2006.01) | |
| A61K 31/415 | (2006.01) | |
| A61K 31/40 | (2006.01) | |

(52) U.S. Cl.
USPC ...... 514/255.05; 514/183; 514/269; 514/314; 514/397; 514/309; 514/394; 514/422; 514/81

(58) Field of Classification Search
USPC ................. 514/183, 269, 314, 397, 309, 394, 514/81, 274, 255.04, 422
See application file for complete search history.

(56) References Cited

U.S. PATENT DOCUMENTS

| | | | |
|---|---|---|---|
| 6,056,961 A | 5/2000 | Lavie et al. | |
| 6,143,752 A | 11/2000 | Oren | |

(Continued)

FOREIGN PATENT DOCUMENTS

| | | |
|---|---|---|
| CA | 2518115 C | 3/2012 |
| DE | 102005038768 A1 | 2/2007 |

(Continued)

OTHER PUBLICATIONS

Fridell et al. "Resistance Analysis of the Hepatitis C virus NS5A inhibitor BMS-790052 in an In Vitro Replicon System," Antimicrobial Agents and Chemotherapy, Sep. 2010, vol. 54, No. 9, pp. 3641-3650.*

(Continued)

Primary Examiner — Shengjun Wang
(74) Attorney, Agent, or Firm — Xu Zhang

(57) ABSTRACT

The present invention features interferon-free therapies for the treatment of HCV. Preferably, the treatment is over a shorter duration, such as no more than 12 weeks. In one aspect, the therapies comprise administering at least two direct acting antiviral agents and ribavirin to a subject with HCV infection. For example, the therapies comprise administering to the subject effective amounts of therapeutic agent 1, therapeutic agent 2 (or therapeutic agent 3), an inhibitor of cytochrome P450 (e.g., ritonavir), and ribavirin.

16 Claims, 21 Drawing Sheets

U.S. PATENT DOCUMENTS

| | | |
|---|---|---|
| 6,403,564 B1 | 6/2002 | Ganguly et al. |
| 6,475,985 B1 | 11/2002 | Wagner et al. |
| 6,689,814 B1 | 2/2004 | Argy et al. |
| 6,849,254 B1 | 2/2005 | Brass et al. |
| 6,936,629 B2 | 8/2005 | Chan Chun Kong et al. |
| 6,995,174 B2 | 2/2006 | Wang et al. |
| 7,012,066 B2 | 3/2006 | Saksena et al. |
| 7,105,499 B2 | 9/2006 | Carroll et al. |
| 7,125,855 B2 | 10/2006 | Bhat et al. |
| 7,153,848 B2 | 12/2006 | Hudyma et al. |
| 7,202,224 B2 | 4/2007 | Eldrup et al. |
| 7,205,330 B2 | 4/2007 | Bogen et al. |
| 7,244,721 B2 | 7/2007 | Saksena et al. |
| 7,348,425 B2 | 3/2008 | Hudyma et al. |
| RE40,525 E | 9/2008 | Llinas-Brunet et al. |
| 7,423,058 B2 | 9/2008 | Bogen et al. |
| 7,429,572 B2 | 9/2008 | Clark |
| 7,470,664 B2 | 12/2008 | Holloway et al. |
| 7,491,794 B2 | 2/2009 | Blatt et al. |
| 7,514,557 B2 | 4/2009 | Busacca et al. |
| 7,585,845 B2 | 9/2009 | Llinas-Brunet et al. |
| 7,592,316 B2 | 9/2009 | Njoroge et al. |
| 7,601,820 B2 | 10/2009 | Wang et al. |
| 7,608,600 B2 | 10/2009 | Storer et al. |
| 7,648,998 B2 | 1/2010 | Bondy et al. |
| 7,728,027 B2 | 6/2010 | Pack et al. |
| 7,754,699 B2 | 7/2010 | Chun et al. |
| 7,772,178 B2 | 8/2010 | Malcolm et al. |
| 7,777,395 B2 | 8/2010 | Xu et al. |
| 7,793,040 B2 | 9/2010 | Bittner, Jr. |
| 7,820,671 B2 | 10/2010 | Babine et al. |
| 7,893,264 B2 | 2/2011 | Casarez et al. |
| 7,906,619 B2 | 3/2011 | Phadke et al. |
| 7,910,728 B2 | 3/2011 | Hildbrand et al. |
| 7,915,291 B2 | 3/2011 | Wang et al. |
| 7,939,667 B2 | 5/2011 | Llinas-Brunet et al. |
| 7,951,787 B2 | 5/2011 | McGuigan |
| 7,951,789 B2 | 5/2011 | Sommadossi et al. |
| 7,964,580 B2 | 6/2011 | Sofia et al. |
| 7,973,040 B2 | 7/2011 | Harper et al. |
| 8,017,771 B2 | 9/2011 | Busacca et al. |
| 8,067,438 B2 | 11/2011 | Llinas-Brunet et al. |
| 8,080,654 B2 | 12/2011 | Harper et al. |
| 8,088,368 B2 | 1/2012 | Guo et al. |
| 8,101,765 B2 | 1/2012 | Busacca et al. |
| 8,106,187 B2 | 1/2012 | Scalone et al. |
| 8,119,602 B2 | 2/2012 | Zhang et al. |
| RE43,298 E | 4/2012 | Saksena et al. |
| 8,148,399 B2 | 4/2012 | Simmen et al. |
| 8,178,491 B2 | 5/2012 | Cho et al. |
| 8,216,999 B2 | 7/2012 | Holloway et al. |
| 8,252,923 B2 | 8/2012 | Babine et al. |
| 2002/0022015 A1 | 2/2002 | Okushin |
| 2002/0119122 A1 | 8/2002 | Stalgis et al. |
| 2003/0004119 A1 | 1/2003 | Ganguly et al. |
| 2003/0032590 A1 | 2/2003 | Dieterich |
| 2003/0044824 A1 | 3/2003 | Abe |
| 2003/0109697 A1 | 6/2003 | Shepard et al. |
| 2003/0138403 A1 | 7/2003 | Drustrup |
| 2003/0187000 A1 | 10/2003 | Yao et al. |
| 2003/0199518 A1 | 10/2003 | Dubuisson et al. |
| 2004/0198840 A1 | 10/2004 | Deloach |
| 2004/0202641 A1 | 10/2004 | Wei et al. |
| 2005/0085528 A1 | 4/2005 | Ahola et al. |
| 2005/0123628 A1 | 6/2005 | Zabrecky |
| 2005/0187170 A1 | 8/2005 | Bantia et al. |
| 2005/0245502 A1 | 11/2005 | Keller |
| 2005/0249702 A1 | 11/2005 | Njoroge et al. |
| 2005/0288245 A1 | 12/2005 | Sarnow et al. |
| 2006/0083785 A1 | 4/2006 | Kerrish et al. |
| 2006/0100148 A1 | 5/2006 | Liu et al. |
| 2006/0105063 A1 | 5/2006 | Hann et al. |
| 2006/0142238 A1 | 6/2006 | McGuigan |
| 2006/0228333 A1 | 10/2006 | Paik |
| 2006/0229293 A1 | 10/2006 | Lotsof |
| 2006/0275366 A1 | 12/2006 | Malcolm et al. |
| 2006/0276404 A1 | 12/2006 | Ghosal et al. |
| 2006/0276406 A1 | 12/2006 | Gupta et al. |
| 2006/0276407 A1 | 12/2006 | Albrecht et al. |
| 2006/0281689 A1 | 12/2006 | Malcolm |
| 2006/0287248 A1 | 12/2006 | Malcolm |
| 2006/0293267 A1 | 12/2006 | Zamore et al. |
| 2007/0004635 A1 | 1/2007 | Albrecht et al. |
| 2007/0021351 A1 | 1/2007 | White et al. |
| 2007/0092512 A1 | 4/2007 | Daaka et al. |
| 2007/0105781 A1 | 5/2007 | Lyons et al. |
| 2007/0207949 A1 | 9/2007 | Ghosal et al. |
| 2007/0224167 A1 | 9/2007 | Emini et al. |
| 2007/0232527 A1 | 10/2007 | Ghosal et al. |
| 2007/0237818 A1 | 10/2007 | Malcolm et al. |
| 2007/0274951 A1 | 11/2007 | Tong et al. |
| 2007/0287664 A1 | 12/2007 | Ralston, II et al. |
| 2008/0004236 A1 | 1/2008 | Comper |
| 2008/0019950 A1 | 1/2008 | Heins et al. |
| 2008/0050336 A1 | 2/2008 | Bachand et al. |
| 2008/0070861 A1 | 3/2008 | Clark |
| 2008/0081791 A1 | 4/2008 | Huang et al. |
| 2008/0161232 A1 | 7/2008 | Hummel et al. |
| 2008/0261906 A1 | 10/2008 | Glenn et al. |
| 2008/0269205 A1 | 10/2008 | Loebel et al. |
| 2008/0275005 A1 | 11/2008 | Murphy et al. |
| 2008/0275141 A1 | 11/2008 | Whiteford |
| 2009/0017457 A1 | 1/2009 | Lu et al. |
| 2009/0028824 A1 | 1/2009 | Chiang et al. |
| 2009/0041716 A1 | 2/2009 | Kim et al. |
| 2009/0047245 A1 | 2/2009 | Younossi |
| 2009/0053263 A1 | 2/2009 | Cunningham et al. |
| 2009/0076100 A1 | 3/2009 | Czarnik |
| 2009/0082366 A1 | 3/2009 | Czarnik |
| 2009/0082414 A1 | 3/2009 | Czarnik |
| 2009/0098123 A1 | 4/2009 | Rice et al. |
| 2009/0105471 A1 | 4/2009 | Blatt et al. |
| 2009/0156545 A1 | 6/2009 | Hostetler et al. |
| 2009/0202476 A1* | 8/2009 | Perrone et al. ............... 424/85.2 |
| 2009/0234102 A1 | 9/2009 | Kohara et al. |
| 2009/0286843 A1 | 11/2009 | Blatt et al. |
| 2009/0297518 A1 | 12/2009 | Honjo et al. |
| 2009/0298916 A1 | 12/2009 | Kauppinen et al. |
| 2010/0009970 A1 | 1/2010 | Johansen et al. |
| 2010/0028301 A1 | 2/2010 | Bondy et al. |
| 2010/0034839 A1 | 2/2010 | Newell et al. |
| 2010/0041617 A1 | 2/2010 | Trepel et al. |
| 2010/0055055 A1 | 3/2010 | Albeck et al. |
| 2010/0056770 A1 | 3/2010 | Axt et al. |
| 2010/0068182 A1 | 3/2010 | Huang et al. |
| 2010/0081672 A1 | 4/2010 | Wan et al. |
| 2010/0093792 A1 | 4/2010 | Berkenbusch et al. |
| 2010/0099695 A1 | 4/2010 | Liverton et al. |
| 2010/0158866 A1 | 6/2010 | Zhu |
| 2010/0166661 A1 | 7/2010 | Zheng et al. |
| 2010/0216725 A1 | 8/2010 | Phadke et al. |
| 2010/0221217 A1 | 9/2010 | Porter et al. |
| 2010/0226885 A1 | 9/2010 | Albrecht et al. |
| 2010/0233122 A1* | 9/2010 | Qiu et al. ..................... 424/85.5 |
| 2010/0234585 A1 | 9/2010 | Wang et al. |
| 2010/0254942 A1* | 10/2010 | Ewart et al. ................. 424/85.5 |
| 2010/0256217 A1 | 10/2010 | Weiner et al. |
| 2010/0272682 A1 | 10/2010 | Tran |
| 2010/0286083 A1 | 11/2010 | Bao et al. |
| 2010/0291034 A1 | 11/2010 | Ralston, II et al. |
| 2010/0297080 A1 | 11/2010 | Bertelsen et al. |
| 2010/0298257 A1 | 11/2010 | Ross et al. |
| 2010/0316594 A1 | 12/2010 | Sommadossi et al. |
| 2010/0317568 A1 | 12/2010 | Degoey et al. |
| 2010/0330173 A1 | 12/2010 | Rossignol et al. |
| 2011/0020272 A1 | 1/2011 | Schubert |
| 2011/0038833 A1 | 2/2011 | Clark |
| 2011/0045001 A1 | 2/2011 | Klosel et al. |
| 2011/0117055 A1* | 5/2011 | MacDonald et al. ........ 424/85.4 |
| 2011/0117057 A1 | 5/2011 | Saksena et al. |
| 2011/0160149 A1 | 6/2011 | Chen et al. |
| 2011/0200582 A1 | 8/2011 | Baryza et al. |
| 2011/0245484 A1 | 10/2011 | Ross et al. |
| 2011/0250176 A1 | 10/2011 | Lemm et al. |
| 2011/0251152 A1 | 10/2011 | Ross et al. |
| 2011/0257122 A1 | 10/2011 | Sofia et al. |
| 2011/0268697 A1 | 11/2011 | Kim et al. |

| | | | |
|---|---|---|---|
| 2011/0306541 A1 | 12/2011 | Delaney, IV et al. | |
| 2011/0311482 A1 | 12/2011 | Wang et al. | |
| 2011/0312973 A1 | 12/2011 | Liepold et al. | |
| 2011/0319323 A1 | 12/2011 | Schricker et al. | |
| 2012/0009148 A1 | 1/2012 | Smith | |
| 2012/0010170 A1 | 1/2012 | Painter | |
| 2012/0052046 A1 | 3/2012 | Chamberlain et al. | |
| 2012/0058084 A1 | 3/2012 | Rau et al. | |
| 2012/0059033 A1 | 3/2012 | Yang et al. | |
| 2012/0071434 A1 | 3/2012 | Smith et al. | |
| 2012/0101049 A1 | 4/2012 | Chen et al. | |
| 2012/0107278 A1 | 5/2012 | Berrey et al. | |
| 2012/0135949 A1 | 5/2012 | Boecher et al. | |
| 2012/0157404 A1 | 6/2012 | Guo et al. | |
| 2012/0171157 A1 | 7/2012 | Simmen et al. | |
| 2012/0196272 A1 | 8/2012 | Chu et al. | |
| 2012/0196794 A1 | 8/2012 | Gao et al. | |
| 2012/0232247 A1 | 9/2012 | Song et al. | |

FOREIGN PATENT DOCUMENTS

| | | | |
|---|---|---|---|
| EP | 1627641 A1 | 2/2006 | |
| EP | 1646639 A2 | 4/2006 | |
| EP | 1827460 A1 | 9/2007 | |
| EP | 1970372 B1 | 11/2010 | |
| JP | 2000212099 A | 8/2000 | |
| KR | 20010068676 A | 7/2001 | |
| MD | 2549 F1 | 9/2004 | |
| MD | 20060037 A | 7/2007 | |
| MD | 3477 F1 | 1/2008 | |
| MX | PA05012606 A | 2/2006 | |
| RO | 118842 B | 12/2003 | |
| RU | 2158604 C2 | 11/2000 | |
| RU | 2212248 C1 | 9/2003 | |
| RU | 2293572 C1 | 2/2007 | |
| RU | 2306134 C2 | 9/2007 | |
| RU | 2306934 C1 | 9/2007 | |
| RU | 2336096 C1 | 10/2008 | |
| RU | 2345787 C2 | 2/2009 | |
| RU | 2348412 C1 | 3/2009 | |
| RU | 2373952 C1 | 11/2009 | |
| RU | 2398582 C1 | 9/2010 | |
| RU | 2400229 C1 | 9/2010 | |
| RU | 2424794 C1 | 7/2011 | |
| RU | 2429877 C1 | 9/2011 | |
| UA | 64191 A | 2/2004 | |
| UA | 68233 A | 7/2004 | |
| WO | 9109605 A1 | 7/1991 | |
| WO | WO9401125 A1 | 1/1994 | |
| WO | WO9618419 A1 | 6/1996 | |
| WO | 9629336 A1 | 9/1996 | |
| WO | WO9636351 A1 | 11/1996 | |
| WO | WO9727866 A1 | 8/1997 | |
| WO | 9733565 A1 | 9/1997 | |
| WO | 9814181 A1 | 4/1998 | |
| WO | WO9819670 A2 | 5/1998 | |
| WO | WO9848621 A1 | 11/1998 | |
| WO | WO9849281 A1 | 11/1998 | |
| WO | WO9915194 A1 | 4/1999 | |
| WO | WO9918993 A1 | 4/1999 | |
| WO | 9929321 A1 | 6/1999 | |
| WO | 9930721 A1 | 6/1999 | |
| WO | WO0001715 A1 | 1/2000 | |
| WO | WO0023454 A1 | 4/2000 | |
| WO | WO0037097 A1 | 6/2000 | |
| WO | WO0037110 A2 | 6/2000 | |
| WO | WO0047240 A1 | 8/2000 | |
| WO | WO0061161 A2 | 10/2000 | |
| WO | 0107454 A1 | 2/2001 | |
| WO | WO0112214 A1 | 2/2001 | |
| WO | 0177091 A2 | 10/2001 | |
| WO | WO0179540 A2 | 10/2001 | |
| WO | WO0203886 A1 | 1/2002 | |
| WO | WO0210743 A1 | 2/2002 | |
| WO | WO 02/18369 * | 3/2002 | |
| WO | WO0218369 A2 | 3/2002 | |
| WO | 0230455 A2 | 4/2002 | |
| WO | WO0230259 A2 | 4/2002 | |
| WO | WO0232414 A2 | 4/2002 | |
| WO | 02053096 A2 | 7/2002 | |
| WO | WO02055100 A2 | 7/2002 | |
| WO | 02079234 A1 | 10/2002 | |
| WO | 02089731 A2 | 11/2002 | |
| WO | 02091989 A2 | 11/2002 | |
| WO | WO03002152 A2 | 1/2003 | |
| WO | WO03007981 A1 | 1/2003 | |
| WO | WO03028461 A1 | 3/2003 | |
| WO | WO03028754 A1 | 4/2003 | |
| WO | WO03028755 A1 | 4/2003 | |
| WO | WO03030923 A1 | 4/2003 | |
| WO | 03037908 A1 | 5/2003 | |
| WO | 03040104 A1 | 5/2003 | |
| WO | WO03037312 A2 | 5/2003 | |
| WO | WO03042377 A1 | 5/2003 | |
| WO | WO03049760 A1 | 6/2003 | |
| WO | WO03072135 A2 | 9/2003 | |
| WO | 03101199 A1 | 12/2003 | |
| WO | WO03101478 A1 | 12/2003 | |
| WO | 2004019934 A1 | 3/2004 | |
| WO | WO2004039996 A1 | 5/2004 | |
| WO | WO2004043435 A2 | 5/2004 | |
| WO | WO2004047673 A2 | 6/2004 | |
| WO | 2004073599 A2 | 9/2004 | |
| WO | WO2004078127 A2 | 9/2004 | |
| WO | WO2004078191 A1 | 9/2004 | |
| WO | WO2004078194 A1 | 9/2004 | |
| WO | WO2004094452 A2 | 11/2004 | |
| WO | 2004112720 A2 | 12/2004 | |
| WO | WO2004103396 A1 | 12/2004 | |
| WO | 2005000308 A1 | 1/2005 | |
| WO | 2005010143 A2 | 2/2005 | |
| WO | 2005012327 A2 | 2/2005 | |
| WO | WO2005016288 A2 | 2/2005 | |
| WO | 2005023289 A1 | 3/2005 | |
| WO | 2005025583 A2 | 3/2005 | |
| WO | WO2005018330 A1 | 3/2005 | |
| WO | WO2005037214 A2 | 4/2005 | |
| WO | WO2005037274 A1 | 4/2005 | |
| WO | WO2005038056 A1 | 4/2005 | |
| WO | WO2005040816 A1 | 5/2005 | |
| WO | WO2005042020 A2 | 5/2005 | |
| WO | WO2005043118 A2 | 5/2005 | |
| WO | 2005063281 A2 | 7/2005 | |
| WO | WO2005062949 A2 | 7/2005 | |
| WO | WO2005067454 A2 | 7/2005 | |
| WO | WO2005067963 A1 | 7/2005 | |
| WO | 2005102353 A1 | 11/2005 | |
| WO | 2005108418 A1 | 11/2005 | |
| WO | WO2005123076 A2 | 12/2005 | |
| WO | WO2006005610 A1 | 1/2006 | |
| WO | WO2006016930 A2 | 2/2006 | |
| WO | WO2006038088 A1 | 4/2006 | |
| WO | WO2006039488 A2 | 4/2006 | |
| WO | WO2006043153 A2 | 4/2006 | |
| WO | 2006046039 A2 | 5/2006 | |
| WO | WO2006050250 A2 | 5/2006 | |
| WO | 2006063149 A1 | 6/2006 | |
| WO | 2006067606 A1 | 6/2006 | |
| WO | WO2006064026 A1 | 6/2006 | |
| WO | 2006072347 A2 | 7/2006 | |
| WO | WO2006084141 A2 | 8/2006 | |
| WO | WO2006085747 A1 | 8/2006 | |
| WO | WO2006089113 A2 | 8/2006 | |
| WO | 2006096285 A2 | 9/2006 | |
| WO | 2006110656 A2 | 10/2006 | |
| WO | WO2006113937 A2 | 10/2006 | |
| WO | 2006119646 A1 | 11/2006 | |
| WO | 2006127289 A1 | 11/2006 | |
| WO | WO2006127482 A1 | 11/2006 | |
| WO | WO2006127757 A2 | 11/2006 | |
| WO | 2006130686 A2 | 12/2006 | |
| WO | 2006133092 A1 | 12/2006 | |
| WO | WO2006130532 A2 | 12/2006 | |
| WO | WO2006130626 A2 | 12/2006 | |
| WO | WO2007021494 A2 | 2/2007 | |
| WO | WO2007022459 A2 | 2/2007 | |
| WO | 2007049265 A2 | 5/2007 | |
| WO | 2007056016 A2 | 5/2007 | |
| WO | 2007058384 A1 | 5/2007 | |

| | | |
|---|---|---|
| WO | WO2007059221 A2 | 5/2007 |
| WO | WO2007062272 A1 | 5/2007 |
| WO | WO2007064691 A1 | 6/2007 |
| WO | 2007075896 A2 | 7/2007 |
| WO | WO2007081974 A2 | 7/2007 |
| WO | WO2007098270 A2 | 8/2007 |
| WO | WO2007109080 A2 | 9/2007 |
| WO | WO2007109604 A2 | 9/2007 |
| WO | WO2007109605 A2 | 9/2007 |
| WO | 2007111866 A2 | 10/2007 |
| WO | 2007112028 A2 | 10/2007 |
| WO | 2007138116 A2 | 12/2007 |
| WO | 2007143164 A1 | 12/2007 |
| WO | 2007149382 A2 | 12/2007 |
| WO | WO2007146712 A2 | 12/2007 |
| WO | WO2008005511 A2 | 1/2008 |
| WO | WO2008008502 A1 | 1/2008 |
| WO | 2008017692 A2 | 2/2008 |
| WO | 2008022006 A2 | 2/2008 |
| WO | 2008024763 A2 | 2/2008 |
| WO | WO2008024843 A2 | 2/2008 |
| WO | WO2008033413 A2 | 3/2008 |
| WO | WO2008033466 A2 | 3/2008 |
| WO | WO2008039179 A1 | 4/2008 |
| WO | 2008058393 A1 | 5/2008 |
| WO | 2008063727 A2 | 5/2008 |
| WO | 2008091763 A1 | 7/2008 |
| WO | WO2008086161 A1 | 7/2008 |
| WO | WO2008089034 A2 | 7/2008 |
| WO | WO2008092954 A2 | 8/2008 |
| WO | 2008106167 A1 | 9/2008 |
| WO | 2008116194 A2 | 9/2008 |
| WO | WO2008106151 A2 | 9/2008 |
| WO | 2008118013 A1 | 10/2008 |
| WO | WO2008124384 A2 | 10/2008 |
| WO | WO2008137126 A2 | 11/2008 |
| WO | WO2008137779 A2 | 11/2008 |
| WO | WO2008141227 A1 | 11/2008 |
| WO | WO2008143647 A2 | 11/2008 |
| WO | WO2008144072 A1 | 11/2008 |
| WO | 2008153610 A2 | 12/2008 |
| WO | 2009009951 A1 | 1/2009 |
| WO | WO2009015336 A2 | 1/2009 |
| WO | WO2009026292 A1 | 2/2009 |
| WO | 2009033183 A2 | 3/2009 |
| WO | 2009039127 A1 | 3/2009 |
| WO | 2009039134 A1 | 3/2009 |
| WO | 2009039248 A2 | 3/2009 |
| WO | WO2009032198 A1 | 3/2009 |
| WO | WO2009038663 A1 | 3/2009 |
| WO | WO2009043176 A1 | 4/2009 |
| WO | WO2009046369 A2 | 4/2009 |
| WO | WO2009061395 A2 | 5/2009 |
| WO | WO2009062737 A1 | 5/2009 |
| WO | 2009082701 A1 | 7/2009 |
| WO | 2009085659 A1 | 7/2009 |
| WO | WO2009085267 A1 | 7/2009 |
| WO | WO2009131696 A1 | 10/2009 |
| WO | 2009138146 A2 | 11/2009 |
| WO | WO2009134616 A2 | 11/2009 |
| WO | 2009152589 A1 | 12/2009 |
| WO | WO2009149179 A2 | 12/2009 |
| WO | WO2009149377 A1 | 12/2009 |
| WO | WO2009150194 A1 | 12/2009 |
| WO | 2010020676 A1 | 2/2010 |
| WO | WO2010017178 A1 | 2/2010 |
| WO | WO2010017432 A1 | 2/2010 |
| WO | WO2010021681 A2 | 2/2010 |
| WO | 2010024384 A1 | 3/2010 |
| WO | 2010030359 A2 | 3/2010 |
| WO | WO 2010/031832 * | 3/2010 |
| WO | WO2010025380 A2 | 3/2010 |
| WO | WO2010027921 A1 | 3/2010 |
| WO | WO2010033443 A1 | 3/2010 |
| WO | 2010034670 A2 | 4/2010 |
| WO | 2010039801 A2 | 4/2010 |
| WO | 2010042683 A1 | 4/2010 |
| WO | WO2010036799 A1 | 4/2010 |
| WO | WO2010038796 A1 | 4/2010 |
| WO | WO2010045266 A1 | 4/2010 |
| WO | WO2010049438 A2 | 5/2010 |
| WO | WO2010053942 A1 | 5/2010 |
| WO | 2010081082 A2 | 7/2010 |
| WO | WO2010076323 A1 | 7/2010 |
| WO | WO2010093843 A2 | 8/2010 |
| WO | WO2010099458 A1 | 9/2010 |
| WO | WO2010101649 A2 | 9/2010 |
| WO | WO2010122538 A1 | 10/2010 |
| WO | 2010132601 A1 | 11/2010 |
| WO | WO2010151472 A1 | 12/2010 |
| WO | WO2010151487 A1 | 12/2010 |
| WO | WO2010151488 A1 | 12/2010 |
| WO | WO2011009961 A1 | 1/2011 |
| WO | WO2011013019 A1 | 2/2011 |
| WO | WO2011014882 A1 | 2/2011 |
| WO | WO2011038224 A1 | 3/2011 |
| WO | 2011046811 A1 | 4/2011 |
| WO | WO2011041551 A1 | 4/2011 |
| WO | WO2011053617 A1 | 5/2011 |
| WO | WO2011056630 A2 | 5/2011 |
| WO | WO2011056650 A2 | 5/2011 |
| WO | WO2011066082 A2 | 6/2011 |
| WO | WO2011066260 A2 | 6/2011 |
| WO | WO2011072370 A1 | 6/2011 |
| WO | WO2011079016 A1 | 6/2011 |
| WO | WO2011094489 A1 | 8/2011 |
| WO | 2011112558 A2 | 9/2011 |
| WO | 2011156578 A1 | 12/2011 |
| WO | WO2011156757 A1 | 12/2011 |
| WO | WO2012009503 A1 | 1/2012 |
| WO | WO2012015712 A1 | 2/2012 |
| WO | WO2012016995 A1 | 2/2012 |
| WO | WO2012018829 A1 | 2/2012 |
| WO | WO2012041771 A1 | 4/2012 |
| WO | WO2012050850 A1 | 4/2012 |
| WO | 2012087596 A1 | 6/2012 |
| WO | 2012139028 A2 | 10/2012 |

OTHER PUBLICATIONS

Sofia et al. "Discovery of beta-D-2'-Deoxy-2'-alpha-fluoro-2'-beta-C-methyluridine Nucleotide Prodrug (PSI-7977) for the treatment of Hepatitis C Virus," J. Med. Chem. 2010, vol. 53, pp. 7202-7218.*

Zein "Clinical Significance of Hepatitis C Virus Genotypes," Clinical Microbiology REviews, 2000, vol. 13, No. 2, pp. 223-235.*

Manns "Advances in hepatitis C infection," Hepatology International, 2009, vol. 3, No. 1, pp. 3.*

Confirmation that Quadruple Therapy with Daclatasvir (NS5A Inhibitor), Asunaprevir (NS3 Inhibitor) and Peginterferon/Ribavirin Results in High Rate of SVR4 in HCV Genotype 1 Null Responders, EASL 47th Annual Meeting, Apr. 18-22, 2012, Barcelona, Spain. Retrieved from the Internet:< URL: http://www.natap.org/2012/EASL/EASL_17.htm>.

Dahari H., et al., "Modeling Hepatitis C Virus Dynamics: Liver Regeneration and Critical Drug Efficacy," Journal of Theoretical Biology, 2007, vol. 247 (2), pp. 371-381.

Everson G.T., et al., An Interferon-Free, Ribavirin-Free 12-Week Regimen of Daclatasvir (DCV), Asunaprevir (ASV), and BMS-791325 Yielded SVR4 of 94% in Treatment-Naive Patients with Genotype (GT) 1 Chronic Hepatitis C Virus (HCV) Infection, 63rd Annual Meeting of the American Association for the Study of Liver Diseases, Boston, Oct. 16, 2012.

Four-Week Treatment with GS-9256 and Tegobuvir (GS-9190) +/− RBV +/− PEG, Results in Enhanced Viral Suppression on Follow-up PEG/RBV Therapy, in Genotype 1a/1b HCV Patients, EASL 46th Annual Meeting, Mar. 30-Apr. 3, 2011, Berlin, Germany. Retrieved from the Internet:< URL: http://www.natap.org/2011/EASL/EASL_49.htm>.

Gane E.J., et al., PSI-7977: Electron Interferon is not required for Sustained Virologic Response in Treatment-Naive Patients with HCV GT2 or GT3, 62th Annual Meeting of the American Association for the Study of Liver Diseases, San Francisco, Nov. 6-9, 2011. Retrieved from the Internet:< URL: http://www.natap.org/2011/AASLD/AASLD_07.htm>.

Gane E.J., et al., Vertex Quad Therapy Yielded 83-93% SVR with 12 Weeks Duration of Therapy: VX-222/Telaprevir in Combination with Peginterferon-Alfa-2a and Ribavirin in Treatment-Naive Genotype 1 HCV Patients Treated for 12 Weeks: Zenith study, SVR12 Interim Analysis, 22nd Conference of the Asian Pacific Association for the Study of the Liver, Taipei, Taiwan, Feb. 16-19, 2012. Retrieved from the Internet:< URL: http://www.natap.org/2012/APASL/APASL_11.htm>.

Interim Phase 2 Data Showed Rapid Viral Response to VX-222 in Combination with Telaprevir, Pegylated-Interferon and Ribavirin Among People With Hepatitis C, EASL 46th Annual Meeting, Mar. 30-Apr. 3, 2011, Berlin, Germany. Retrieved from the Internet:< URL: http://www.natap.org/2011/EASL/EASL_11.htm>.

Jacobson I., et al., GS-7977 400 mg QD Safety and Tolerability in the Over 500 Patients Treated for at Least 12 Weeks, EASL 47th Annual Meeting, Apr. 18-22, 2012, Barcelona, Spain. Retrieved from the Internet:< URL: http://www.natap.org/2012/EASL/EASL_55.htm>.

Kowdley K., et al., GS-7977 + PEG/RBV in HCV Genotype 1: The Atomic Trial. An End to Response-Guided Therapy? 47th Annual Meeting of the European Association for the Study of the Liver, Apr. 18-22, 2012, Barcelona, Spain. Retrieved from the Internet:< URL: http://www.natap.org/2012/EASL/EASL_30.htm>.

Lalezari J., et al., Proton Study: PSI-7977 QD with PEG/RBV: 12-week Safety, RVR, cEVR, & SVR12 in Treatment-naive Patients with HCV GT2 or GT3, EASL 46th Annual Meeting, Mar. 30-Apr. 3, 2011, Berlin, Germany. Retrieved from the Internet:< URL: http://www.natap.org/2011/EASL/EASL_22.htm>.

Lawitz E., et al., A Phase 2b Trial Comparing 24 to 48 Weeks Treatment with Tegobuvir (GS-9190)/PEG/RBV to 48 Weeks Treatment with PEG/RBV for Chronic Genotype 1 HCV Infection, EASL 46th Annual Meeting, Mar. 30-Apr. 3, 2011, Berlin, Germany. Retrieved from the Internet:< URL: http://www.natap.org/2011/EASL/EASL_67.htm>.

Lawitz E., et al., GS-7977 Phase 2 Trials: Concordance of SVR4 with SVR12 and SVR24 in HCV Genotypes 1-3, EASL 47th Annual Meeting, Apr. 18-22, 2012, Barcelona, Spain. Retrieved from the Internet:< URL: http://www.natap.org/2012/EASL/EASL_29.htm>.

Lawitz E., et al., Proton: PSI-7977 & Peg/RBV in Treatment-Naive Patients with HCV GT1: Sustained Virologic Response, 62th Annual Meeting of the American Association for the Study of Liver Diseases, San Francisco, Nov. 6-9, 2011. Retrieved from the Internet:< URL: http://www.natap.org/2011/AASLD/AASLD_21.htm>.

Lawitz E., et al., PSI-7977 400 mg with PEG/RBV Provides 93% SVR Across HCV GT 1, 2 and 3, HepDART 2011, Kauai, HI, USA. Retrieved from the Internet:< URL: http://www.natap.org/2011/hepDART/hepDART_02.htm>.

Lok A., et al., Combination Therapy With BMS-790052 and BMS-650032 Alone or With Pegylated Interferon and Ribavirin (pegIFN/RBV) Results in Undetectable HCV RNA Through 12 Weeks of Therapy in HCV Genotype 1 Null Responders, 61th Annual Meeting of the American Association for the Study of Liver Diseases Boston, MA, Oct. 30-Nov. 3, 2010. Retrieved from the Internet:< URL: http://www.natap.org/2010/AASLD/AASLD_16.htm>.

Neal L., et al., Theoretical and Experimental Comparison of Hepatitis C Viral Dynamics Models and Parameter Estimates, American Conference on Pharmacometrics, 2009, Retrieved from the Internet:< URL: http://2009.go-acop.org/acop2009/posters>.

Nelson D.R., et al. PSI-7977 QD Plus PEG/RBV In HCV GT1: 98% Rapid Virologic Response, Complete Early Virologic Response: The Proton Study, EASL 46th Annual Meeting, Mar. 30-Apr. 3, 2011, Berlin, Germany. Retrieved from the Internet:< URL: http://www.natap.org/2011/EASL/EASL_06.htm>.

Nelson D.R., et al., VX-222/Telaprevir in Combination With Peginterferon-Alfa-2a and Ribavirin in Treatment-Naive Genotype 1 HCV Patients Treated for 12 Weeks: Zenith Study, SVR12 Interim Analysis, 62th Annual Meeting of the American Association for the Study of Liver Diseases, San Francisco, Nov. 6-9, 2011. Retrieved from the Internet:< URL: http://www.natap.org/2011/AASLD/AASLD_32.htm>.

Neumann A.U., et al., "Hepatitis C Viral Dynamics in Vivo and the Antiviral Efficacy of Interferon-alpha Therapy," Science, 1998, vol. 282 (5386), pp. 103-107.

Patients of all IL28B Genotypes have High SVR Rates when Treated with VX-222 in Combination with Telaprevir/Peginterferon/Ribavirin in the Zenith Study, EASL 47th Annual Meeting, Apr. 18-22, 2012, Barcelona, Spain. Retrieved from the Internet:< URL: http://www.natap.org/2012/EASL/EASL_53.htm>.

Pawlotsky J.M., et al., Alisporivir (Alv) Plus Ribavirin Is Highly Effective as Interferon-Free or Interferon-Add-On Regimen in Previously Untreated HCV-G2 or G3 Patients: SVR12 Results From Vital-1 Phase 2b Study, EASL 47th Annual Meeting, Apr. 18-22, 2012, Barcelona, Spain. Retrieved from the Internet:< URL: http://www.natap.org/2012/EASL/EASL_36.htm>.

Poordad F., et al., A 12-Week Interferon-Free Regimen of ABT-450/r + ABT-333 + Ribavirin Achieved SVR12 in More Than 90% of Treatment-Naïve HCV Genotype-1-Infected Subjects and 47% of Previous Non-Responders, EASL 47th Annual Meeting, Apr. 18-22, 2012, Barcelona, Spain. Retrieved from the Internet:< URL: http://www.natap.org/2012/EASL/EASL_41.htm>.

Rong L., et al., "Rapid Emergence of Protease Inhibitor Resistance in Hepatitis C Virus," Science Translational Medicine, 2010, vol. 2 (30), pp. 30ra32.

Shudo E., et al., "A Hepatitis C Viral Kinetic Model that Allows for Time-varying Drug Effectiveness," Antiviral Therapy, 2008, vol. 13 (7), pp. 919-926.

Snoeck E., et al., "A Comprehensive Hepatitis C Viral Kinetic Model Explaining Cure," Clinical Pharmacology and Therapeutics, 2010, vol. 87 (6), pp. 706-713.

Suzuki F., et al., Dual Oral Therapy with NS5A Inhibitor Daclatasvir (BMS-790052) and NS3 Protease Inhibitor Asunaprevir (BMS-650032) in HCV Genotype 1b-Infected Null Responders or Patients Ineligible/Intolerant to Peginterferon/Ribavirin, EASL 47th Annual Meeting, Apr. 18-22, 2012, Barcelona, Spain. Retrieved from the Internet:< URL: http://www.natap.org/2012/EASL/EASL_27.htm>.

Zeuzem S., et al., Strong Antiviral Activity and Safety of IFN-Sparing Treatment with the Protease Inhibitor BI 201335, the HCV Polymerase Inhibitor BI 207127, and Ribavirin, in Patients with Chronic Hepatitis C: the Sound-C1 Trial, 61st Annual Meeting of the American Association for the Study of Liver Diseases, Oct. 30-Nov. 3, 2010, Boston, MA, USA. Retrieved from the Internet:< URL: http://www.natap.org/2010/AASLD/AASLD_30.htm>.

Zeuzem S., et al., The Protease Inhibitor GS-9256 and Non-Nucleoside Polymerase Inhibitor Tegobuvir Alone, With RBV or Peginterferon plus RBV in Hepatitis C, Hepatology, Hepatitis C Articles (HCV), Jan. 2012. Retrieved from the Internet:< URL: http://www.natap.org/2012/HCV/011212_06.htm>.

Zeuzem S., et al., Virologic Response to an Interferon-Free Regimen of BI 201335 and BI 207127, with and without Ribavirin, in Treatment-Naive Patients with Chronic Genotype-1 HCV Infection: Week 12 Interim Results of the Sound-C2 Study, 62th Annual Meeting of the American Association for the Study of Liver Diseases, San Francisco. Nov. 6-9, 2011. Retrieved from the Internet:< URL: http://www.natap.org/2011/AASLD/AASLD_19.htm>.

Co-pending U.S. Appl. No. 13/656,012, filed Oct. 19, 2012.

Co-pending U.S. Appl. No. 13/656,024, filed Oct. 19, 2012.

Gane E.J., et al., "Electron: Once Daily PSI-7977 Plus RBV in HCV GT1/2/3," Journal of Hepatology, 2012, vol. 56, pp. S438-S439.

Gane E.J., et al., "Once Daily PSI-7977 Plus RBV: Pegylated Interferon-Alfa not Required for Complete Rapid Viral Response in Treatment-Naive Patients with HCV GT2 or GT3," American Association for the Study of Liver Diseases: The Liver Meeting, Abstracts, Hepatology, 2011, vol. 54 (4), pp. 377A.

Sulkowski M., et al., "High Sustained Virologic Response Rate in Treatment-Naive HCV Genotype 1A and 1B Patients Treated for 12 Weeks with an Interferon-Free All-Oral Quad Regimen: Interim Results," Journal of Hepatology, 2012, vol. 56, pp. S560.

Suzuki F., et al., "Dual Oral Therapy with the NS5A Inhibitor Daclatasvir (BMS-790052) and NS3 Protease Inhibitor Asunaprevir (BMS-650032) in HCV Genotype 1B-Infected Null Responders or Ineligible/intolerant to Peginterferon/Ribavirina," Journal of Hepatology, 2012, vol. 56, pp. S7-S8.

AASLD-INCIVEK™ / VX-222-Interim Data Showed at 12wk 93% SVR, HCV New Drug Research [online], Nov. 2011 [retrieved on Feb. 13, 2012]. Retrieved from the Internet:< URL: http://hepatitiscnewdrugs.blogspot.com/2011/11/aasld-incivek-vx-222-interim-data.html>.

ABT Investor Meeting, Raw Transcript, Abbott Laboratories, Oct. 21, 2011, pp. 16 and 17.

Achillion Announces Positive SVR4 Results From Phase 2 Study of Sovaprevir (Formerly ACH-1625) and Advancement of ACH-3102, News, Achillion Pharmaceuticals, Aug. 7, 2012.

Achillion Reports First Quarter 2012 Financial Results, Achillion Pharmaceuticals, May 9, 2012.

All-Oral Combination of Investigational Hepatitis C (HCV) Compounds Daclatasvir and GS-7977 Achieved Sustained Virologic Response (SVR4) in 100% of Genotype 1 and 91% of Genotype 2 and 3 Treatment- Naïve Patients in Phase II Study, Business Wire Press Release Archive [online], Apr. 2012 [retrieved on Aug. 9, 2012]. Retrieved from the Internet:< URL: http://www.businesswire.com/news/home/20120419005320/en/All-Oral-Combination-Inves>.

All-Oral Combination of Investigational Hepatitis C (Hcv) Compounds Daclatasvir and GS-7977 Achieved Sustained Virologic Response (SVR4) in 100% of Genotype 1 and 91% of Genotype 2 and 3 Treatment-Naïve Patients in Phase II Study, Bristol-Myers Squibb Company Press Release [online] Apr. 2012 [retrieved on Aug. 9, 2012]. Retrieved from the Internet:< URL: http://bms.newshq.businesswire.com/press-release/rd-news/all-oral-combination-investigati>.

Barry A., et al., "A Study of the Safety and Pharmacokinetics of Single Ascending Oral Doses of INX-08189, a Nucleotide Polymerase Inhibitor, in Healthy Subjects," EASL, Poster, 2011.

BI 201335 Demonstrates Potential to Shorten HCV Treatment Duration while Achieving High Sustained Virological Response Rates in Difficult to Treat Patients, Boehringer Ingelheim Press Release Archive [online], Nov. 2011 [retrieved on Feb. 23, 2012]. Retrieved from the Internet:< URL: http://www.boehringer-ingelheim.com/news/news_releases/press_release . . . >.

Chayama K., et al., Dual Oral Combination Therapy with the NS5A Inhibitor Daclatasvir(DCV; BMS-790052) and the NS3 Protease Inhibitor Asunaprevir(ASV; BMS-650032) Achieved 90% Sustained Virologic Response (SVR12) in Japanese HCV Genotype 1b-Infected Null Responders, 62th Annual Meeting of the American Association for the Study of Liver Diseases [online], 2011 [retrieved on Feb. 21, 2012]. Retrieved from the Internet:< URL: http://www.natap.org/2011/AASLD/AASLD_17.htm>.

Chayama K., et al., Dual therapy with the nonstructural Protein 5A Inhibitor, BMS-790052, and the Nonstructural Protein 3 Protease Inhibitor, BMS- 650032, in Hepatitis C Virus Genotype 1b-Infected Null Responders, Hepatology [online], 2012 [retrieved on Feb. 22, 2012]. Retrieved from the Internet:< URL: http://onlinelibrary.wiley.com/doi/10.1002/hep.24724/abstract;jsessionid=C8D1A7A2178A18AE863EAF341C4D644C.d01t03>.

Cheng G., et al., Antiviral Activity and Resistance Profile of the Novel HCV NS5A Inhibitor GS-5885, EASL 2012—Session Planner, Abstract 1172 [online], 2012 [retrieved on Apr. 4, 2012]. Retrieved from the Internet:< URL: http://www.abstractserver.com/easl2012/planner/index.php?go=abstract& . . . >.

Co-pending U.S. Appl. No. 13/412,167, filed Mar. 5, 2012.

Co-pending U.S. Appl. No. 13/603,006, filed Sep. 4, 2012.

Co-pending U.S. Appl. No. 13/621,454, filed Sep. 17, 2012.

Cornpropst M.T., et al., The Effect of Renal Impairment and End Stage Renal Disease on the Single-Dose Pharmacokinetics of PSI-7977, EASL 2012—Session Planner, Abstract 1101 [online], 2012 [retrieved on Apr. 4, 2012]. Retrieved from the Internet:< URL: http://www.abstractserver.com/easl2012/planner/index.php?go=abstract& . . . >.

Devogelaere B., et al., "TMC647055, a Potent Nonnucleoside Hepatitis C Virus NS5B Polymerase Inhibitor with Cross-Genotypic Coverage," Antimicrobial Agents and Chemotherapy, 2012, vol. 56 (9), pp. 4676-4684.

Di Bisceglie A.M., et al., "VX-222 with TVR alone or in Combination with Peginterferon Alfa-2A and Ribavirin in Treatmentnaive Patients with Chronic Hepatitis C: Zenith Study Interim Results," EASL Poster Presentations, 2011.

Dvory-Sobol H., et al., In-Vitro Fitness and Resistance Analyses of NS3 Mutants Detected by Population and Deep Sequencing in HCV Patients from Phase I Studies of GS-9451 and GS-9256, EASL 2012—Session Planner, Abstract 1175 [online], 2012 [retrieved on Apr. 4, 2012]. Retrieved from the Internet:< URL: http://www.abstractserver.com/easl2012/planner/index.php?go=abstract& . . . >.

Flinn R., Gilead Gains on Positive Data From Experimental Hepatitis C Drug, Bloomberg [online], 2012, [retrieved on Feb. 17, 2012]. Retrieved from the Internet:< URL: http://www.bloomberg.com/news/print/2012-02-03/gilead-gains-on-positive-data-from-experimental-hepatitis-c-drug.html>.

Frangou C., "New Study of Interferon-free HCV Therapy Hailed as 'Watershed Moment' in Hep C Research," Gastroenterology & Endoscopy News, 2012, vol. 63:2 [online], [retrieved on Feb. 13, 2012]. Retrieved from the Internet:< URL: http://www.gastroendonews.com/ViewArticle.aspx?d=Breaking+News&d_id=409&i=February+2012&i_id=809&a_id=20098>.

Fridell R.A., et al., "Resistance Analysis of the Hepatitis C Virus NS5A Inhibitor BMS-790052 in an in Vitro Replicon System," Antimicrobial Agents and Chemotherapy, 2010, vol. 54 (9), pp. 3641-3650.

Gane E., et al., Once Daily GS-7977 Plus Ribavirin in HCV Genotypes 1-3: The ELECTRON Trial, 47th Annual Meeting of the European Association for the Study of the Liver, Poster No. 1113, 2012.

Gane E.J., et al., Interferon-Free Treatment with a Combination of Mericitabine and Danoprevir/R with or without Ribavirin in Treatment-Naive HCV Genotype 1-Infected Patients, EASL 2012—Session Planner, Abstract 1412 [online], 2012 [retrieved on Apr. 4, 2012]. Retrieved from the Internet:< URL: http://www.abstractserver.com/easl2012/planner/index.php?go=abstract& . . . >.

Gilead Advancing Therapeutics, Gilead Sciences Annual Meeting of Stockholders, May 10, 2012.

Gilead Advancing Therapeutics, Q2 2012 Earnings Results Conference Call and Webcast, Jul. 26, 2012.

Gilead Announces Early Sustained Virologic Response Rates for GS-7977 Plus Ribavirin in Genotype 1 Treatment-Naive Hepatitis C Patients, Press Releases: Gilead [online], 2012 [retrieved on Jun. 21, 2012]. Retrieved from the Internet:< URL: http://www.gilead.com/pr_1684792>.

Gilead, Bristol Put Profits Ahead of Best Care for Hep C Patients, Apr. 19, 2012, [retrieved on Aug. 9, 2012], Retrieved from the Internet:< URL:http://www.thestreet.com/print/story/11501206.html>.

Gilead Sciences Inc., 10-K, Annual Report Pursuant to Section 13 and 15(d), Filed on Feb. 23, 2012.

Goelzer P., et al., Ritonavir Substantially Reduces Reactive Metabolite Formation of the HCV Protease Inhibitor Danoprevir Both in Vitro and in Vivo, EASL 2012—Session Planner, Abstract 1180 [online], 2012 [retrieved on Apr. 4, 2012]. Retrieved from the Internet:< URL: http://www.abstractserver.com/easl2012/planner/index.php?go=abstract& . . . >.

GS-5885, GS-9451, Tegobuvir and Ribavirin (RBV) in Treatment—Experienced Subjects With Chronic Genotype 1a or 1b Hepatitis C Virus (HCV) Infection, ClinicalTrials.gov Identifier: NCT01435226, Gilead Sciences, 2011.

GS-7977 + Ribavirin for 12 or 16 Weeks in Treatment Experienced Subjects with Chronic Genotype 2 or 3 HCV Infection (Fusion), ClinicalTrials.gov Identifier: NCT01604850, Gilead Sciences. Retrieved from the Internet:< URL: http://clinicaltrials.gov/show/NCT01604850>.

Guidance for Industry Chronic Hepatitis C Virus Infection: Developing Direct—Acting Antiviral Agents for Treatment, Draft Guidance, Food and Drug Administration, Sep. 2010, pp. 1-27.

HCV New Drug Research, Sep. 30, 2011, [retrieved on Feb. 21, 2012], Retrieved from the Internet:< URL: http://hepatitiscnewdrugs.blogspot.in/2011_09_01_archive.html>.

HCV Polymerase Inhibitor VX-222 Demonstrates Good Safety and Antiviral Activity in Treatment-naive Genotype 1 Hepatitis C Patients, 45th EASL [online], Apr. 2010 [retrieved on Feb. 13, 2012]. Retrieved from the Internet:< URL: http://www.hivandhepatitis.com/2010_conference/easl/docs/0420_2010_c.html>.

Hepatitis C Virus Polymerase Inhibitor VX-222 Reduced Viral Levels Over Three Days in Phase 1b Trial, Apr. 2010 [retrieved on Feb. 13, 2012], Retrieved from the Internet:< URL: http://www.medicalnewstoday.com/releases/185729.php>.

Idenix Announces Positive Clinical Data for HCV Drug Candidates IDX184 and IDX719, Idenix Pharmaceuticals News, General Releases, Jun. 19, 2012.

Idenix Pharmaceuticals Announces Restructuring of Development and Commercialization Collaboration With Novartis Pharma AG, Idenix Pharmaceuticals News, General Releases, Jul. 31, 2012.

Inhibitex Reports Recent Clinical and Corporate Developments [online], Nov. 2011, [retrieved on Aug. 9, 2012]. Retrieved from the Internet:< URL: http://markets.financialcontent.com/ir/?Module=MediaViewer&GUID=20067838&Ticker=>.

Interim Data from Phase 2 Study Showed 93% of People With Hepatitis C Who Received a Total of 12 Weeks of a Combination Regimen Including INCIVEK™ (telaprevir) and VX-222 (400mg) Achieved a Viral Cure (SVR), Vertex Pharmaceuticals, Press Release [online], 2012 [retrieved on Feb. 13, 2012]. Retrieved from the Internet:< URL: http://www.evaluatepharma.com/...%22%3a%5c%2226209 3%5c%22%2c%5c%22notSub%5c%22%3afalse%7d%22%7d% 2c%22_Type%22%3a1%7d>.

Jacobson I., et al., PSI-7977 400 Mg QD Safety and Tolerability in the First 450 Patients Treated for 12 Weeks, EASL 2012—Session Planner, Abstract 1120 [online], 2012 [retrieved on Apr. 4, 2012]. Retrieved from the Internet:< URL: http://www.abstractserver.com/easl2012/planner/index.php?go=abstract& ...>.

Jefferies, Gilead Sciences (GILD), Correction: More on EASL Abstracts on Oral Combination Regimens, Apr. 9, 2012.

Kennedy V.B., Can Vertex Pharma Shares Stage a Comeback?, MarketWatch, Feb. 2012, [retrieved on Feb. 13, 2012], Retrieved from the Internet:< URL: http://www.marketwatch.com/story/can-vertex-pharma-shares-stage-a-comeback-2012-02-10>.

Lagace L., et al., "Genotypic and Phenotypic Analysis of the NS5B Polymerase Region from Viral Isolates of HCV Chronically Infected Patients Treated with BI 207127 for 5 Days' Monotherapy," The 61st Annual Meeting of the American Association for the Study of Liver Diseases (AASLD), 2010.

Lam A.M., et al., "PSI-7851, a Pronucleotide of Beta-D-2'-deoxy-2'-fluoro-2'-C-methyluridine Monophosphate, is a Potent and Pan-genotype Inhibitor of Hepatitis C Virus Replication," Antimicrobial Agents and Chemotherapy, 2010, vol. 54 (8), pp. 3187-3196.

Larrey D., et al., "High Sustained Virological Response (SVR) Rate After Danoprevir for Only 14 Days Associated with Peg-Interferon Alfa-2A and Ribavirin in Treatment-Naive Chronic HCV Genotype 1 Patients, Poster 1218," Journal of Hepatology, 2011, vol. 54, pp. S481.

Lawitz E., et al., A 12-Week Interferon-Free Regimen of ABT-450/R, ABT-072, and Ribavirin was Well Tolerated and Achieved Sustained Virologic Response in 91% Treatment-Naive HCV IL28B-CC Genotype-1-Infected Subjects, EASL 2012—Session Planner, Abstract 13 [online], 2012 [retrieved on Apr. 4, 2012]. Retrieved from the Internet:< URL: http://www.abstractserver.com/easl2012/planner/index.php?go=abstract& ...>.

Lawitz E., et al., "ABT-450/Ritonavir (ABT-450/R) Combined with Pegylated Interferon Alpha-2A and Ribavirin (Soc) After 3-Day Monotherapy in Genotype 1 HCV-Infected Treatment-Naive Subjects: 12-Week Interim Efficacy and Safety Results, Poster 1220," Journal of Hepatology, 2011, vol. 54, pp. S482.

Lawitz E., et al., PSI-7977 Proton and Electron: 100% Concordance of SVR4 With SVR24 in HCV GT1, GT2, & GT3, EASL 2012—Session Planner, Abstract 7 [online], 2012 [retrieved on Apr. 4, 2012]. Retrieved from the Internet:< URL: http://www.abstractserver.com/easl2012/planner/index.php?go=abstract& ...>.

Lawitz E., et al., The Effect of Hepatic Impairment on the Pharmacokinetics and Antiviral Activity of PSI-7977 in Hepatitis C Infected Subjects Treated for Seven Days, EASL 2012—Session Planner, Abstract 1130 [online], 2012 [retrieved on Apr. 4, 2012]. Retrieved from the Internet:< URL: http://www.abstractserver.com/easl2012/planner/index.php?go=abstract& ...>.

Lawitz E., et al., Three-Day, Dose-Ranging Study of the HCV NS5A Inhibitor GS-5885, 46th Annual Meeting of the European Association for the Study of the Liver, Poster No. 1219, 2011.

Lawitz E., et al., "Three-Day, Dose-Ranging Study of the HCV NS5A Inhibitor GS-5885, Poster 1219," Journal of Hepatology, 2011, vol. 54, pp. S481-S482.

Lawitz E.J., et al., "A Phase 1, Randomized, Placebo-controlled, 3-day, Dose-ranging Study of GS-5885, an NS5A Inhibitor, in Patients with Genotype 1 Hepatitis C," Journal of Hepatology, 2012, vol. 57 (1), pp. 24-31.

Le Pogam S., et al., "RG7128 Alone or in Combination with Pegylated Interferon-alpha2a and Ribavirin Prevents Hepatitis C Virus (HCV) Replication and Selection of Resistant Variants in HCV-infected Patients," Journal of Infectious Diseases, 2010, vol. 202 (10), pp. 1510-1519.

Lemke C.T., et al., "Combined X-ray, NMR, and Kinetic Analyses Reveal Uncommon Binding Characteristics of the Hepatitis C Virus NS3-NS4A Protease Inhibitor BI 201335," Journal of Biological Chemistry, 2011, vol. 286 (13), pp. 11434-11443.

Lemm J.A., et al., "Discovery of Potent Hepatitis C Virus NS5A Inhibitors with Dimeric Structures," Antimicrobial Agents and Chemotherapy, 2011, vol. 55 (8), pp. 3795-3802.

Lemm J.A., et al., In Vitro DAA Combination Studies to Address HCV Clinical Findings, European Association for the Study of the Liver [online], Apr. 2011 [retrieved on Feb. 22, 2012], Retrieved from the Internet:< URL: http://www1.easl.eu/easl2011/program/Posters/Abstract680.htm>.

Levin J., GS-7977 + Ribavirin in HCV Genotype 1 Null Responders: Results from the Electron Trial, Mar. 2012 [retrieved on Mar. 23, 2012], Retrieved from the Internet:< URL: http://www.natap.org/2012/CROI/croi_07.htm>.

Levin J., Interferon-free Treatment with a Combination of Mericitabine and Danoprevir/R without Ribavirin in Treatment-naive HCV Genotype 1—Infected Patients, European Association for the Study of the Liver [online], Apr. 2012 [retrieved on Jun. 13, 2012], Retrieved from the Internet:< URL: http://www.natap.org/2012/EASL/EASL_52.htm>.

Link J., et al., Nonclinical Profile and Phase I Results in Healthy Volunteers of the Novel and Potent HCV NS5A Inhibitor GS-5885, 61st AASLD, Poster No. 1883, 2010.

Lok A.S., et al., "Preliminary Study of Two Antiviral Agents for Hepatitis C Genotype 1," New England Journal of Medicine, 2012, vol. 366 (3), pp. 216-224.

McGuigan C., et al., "Dual Pro-Drugs of 2'-C-Methyl Guanosine Monophosphate as Potent and Selective Inhibitors of Hepatitis C Virus," Bioorganic & Medicinal Chemistry Letters, 2011, vol. 21 (19), pp. 6007-6012.

McPhee F., et al., "Resistance Analysis of the Hepatitis C Virus NS3 Protease Inhibitor Asunaprevir," Antimicrobial Agents and Chemotherapy, 2012, vol. 56 (7), pp. 3670-3681.

Medivir AB, A Phase IIa Interferon Free Combination Hepatitis C Trial of Simeprevir (TMC435) and TMC647055 will Commence Shortly, Press Release, Stockholm, Sweden, Sep. 20, 2012.

Medivir Announces an Interferon-free Phase II Combination Trial with TMC435 and Daclatascir to Commence Shortly, Press Release on Jun. 29, 2012.

Medivir Announces TMC435 in an Expanded Clinical Collaboration, Press Release on Apr. 18, 2012.

Murakami E., et al., "Mechanism of Activation of PSI-7851 and its Diastereoisomer PSI-7977," Journal of Biological Chemistry, 2010, vol. 285 (45), pp. 34437-34347.

Nettles R., et al., BMS-790052 is a First-in-class Potent Hepatitis C Virus (HCV) NS5A Inhibitor for Patients with Chronic HCV Infection: Results from a Proof-of-concept Study, Annual Meeting of the American Association for the Study of Liver Diseases (AASLD), 2008.

New Data on Tibotec Investigational Hepatitis C Compounds Being Presented at EASL, [retrieved on Feb. 14, 2012], Retrieved from the Internet:< URL:http://www.jnj.com/connect/news/all/20090424_100000>.

Novartis, Pharmaceuticals, Jul. 2012, 19 pages.

Pharmasset, Bristol-Myers Squibb and Pharmasset Enter into a Clinical Collaboration Agreement for Proof of Concept Combination Study in Patients Chronically Infected with Hepatitis C.

Pharmasset, NASDAQ: VRUS.

Phase 2b Study of Boehringer Ingelheim's Interferon-Free Hepatitis C Treatment Shows Undetectable Virus in HCV Genotype-1 Patients 12 Weeks After Treatment Ended (SVR12), Apr. 19, 2012.
Poordad F., et al., 12-Week Interferon-Free Regimen of ABT-450/R+ABT-333+Ribavirin Achieved SVR12 in more than 90% of Treatment-Naive HCV Genotype-1-Infected Subjects and 47% of Previous Non-Responders, EASL 2012—Session Planner, Abstract 1399 [online], 2012 [retrieved on Apr. 4, 2012]. Retrieved from the Internet:< URL: http://www.abstractserver.com/easl2012/planner/index.php?go=abstract& . . . >.
Potent Viral Suppression with the All-Oral Combination of Daclatasvir (NS5A Inhibitor) and GS-7977 (Nucleotide NS5B Inhibitor), +/− Ribavirin, in Treatment-Naive Patients With Chronic HCV GT1, 2, or 3 (100% SVR gt1, 91% gt2), EASL 47th Annual Meeting [online], 2012 [retrieved on Jun. 11, 2012]. Retrieved from the Internet:< URL: http://www.natap.org/2012/EASL/EASL_24.htm>.
Rodriguez-Torres M., et al., Antiviral Activity and Safety of INX-08189, a Nucleotide Polymerase Inhibitor, Following 7-Days of Oral Therapy in Naive Genotype-1 HCV Patients, American Association for the Study of Liver Diseases (AASLD), 2011, Poster 354.
Rodriguez-Torres M., et al. The Effect of Hepatic Impairment on the Safety, Pharmacokinetics and Antiviral Activity of PSI-938 in Hepatitis C Infected Subjects Treated for Seven Days, EASL 2012—Session Planner, Abstract 1153 [online], 2012 [retrieved on Apr. 4, 2012]. Retrieved from the Internet:< URL: http://www.abstractserver.com/easl2012/planner/index.php?go=abstract& . . . >.
Safety, Antiviral Effect and PK of BI 207127 + BI 201335 +/− RBV for 4 up to 40 Weeks in Patients With Chronic HCV Genotype 1 Infection, BI201335, ClinicalTrials.gov Identifier: NCT01132313, Jun. 28, 2011.
Sarrazin C., et al., "Antiviral Strategies in Hepatitis C Virus Infection," Journal of Hepatology, 2012, Suppl. 1, pp. S88-S100.
Setback for Gilead Drug, The Wall Street Journal, [retrieved on Feb. 17, 2012], Retrieved from the Internet:< URL: http://online.wsj.com/article/SB10001424052970204792404577229083586877226.html?mod=WSJ_hps_sections_health>.
Shi J., et al., "Synthesis and Biological Evaluation of New Potent and Selective HCV NS5A Inhibitors," Bioorganic & Medicinal Chemistry Letters, 2012, vol. 22 (10), pp. 3488-3491.
Simion A., et al., Absence of Photosensitivity Potential of TMC435 in Healthy Volunteers, EASL 2012—Session Planner, Abstract 1159 [online], 2012 [retrieved on Apr. 4, 2012]. Retrieved from the Internet:< URL: http://www.abstractserver.com/easl2012/planner/index.php?go=abstract& . . . >.
Soriano V., et al., The Efficacy and Safety of the Interferon-Free Combination of BI201335 and BI207127 in Genotype 1 HCV Patients with Cirrhosis—Interim ANalysis from Sound-C2, EASL 2012—Session Planner, Abstract 1420 [online], 2012 [retrieved on Apr. 12, 2012]. Retrieved from the Internet:< URL: http://www.abstractserver.com/easl2012/planner/index.php?go=abstract&action_i . . . >.
Study to Determine the Safety and Effectiveness of Antiviral Combination Therapy to Treat Hepatitis C Virus (HCV) Infected Patients Who Have Previously not been Treated with Standard of Care, Pharmasset, ClinicalTrials.gov Identifier: NCT01359644, Aug. 30, 2011.
Sulkowski M., et al., High Sustained Virologic Response Rate in Treatment-Naive HCV Genotype 1A and 1B Patients Treated for 12 Weeks with an Interferon-Free All-Oral Quad Regimen: Interim Results, EASL 2012—Session Planner, Abstract 1421 [online], 2012 [retrieved on Apr. 4, 2012]. Retrieved from the Internet:< URL: http://www.abstractserver.com/easl2012/planner/index.php?go=abstract& . . . >.
Sulkowski M., et al., Interim Sustained Virologic Response Rates in Treatment-Naive HCV Genotype 1a and 1b Patients Treated for 12 or 24 Weeks with an Interferon-Free All-Oral Quad Regimen, European Association for the Study of the Liver, 2012, Poster 1421.
Suzuki F., et al., Dual Oral Therapy with the NS5A Inhibitor Daclatasvir (BMS-790052) and NS3 Protease Inhibitor Asunaprevir (BMS-650032) in HCV Genotype 1B-Infected Null Responders or Ineligible/Intolerant to Peginterferon/Ribavirin, EASL 2012—Session Planner, Abstract 14 [online], 2012 [retrieved on Apr. 4, 2012].
Retrieved from the Internet:< URL: http://www.abstractserver.com/easl2012/planner/index.php?go=abstract& . . . >.
The Big Bang in Hepatitis C, Credit Suisse, Jul. 13, 2011.
Vertex Advances INCIVEK (telaprevir) and Broad Portfolio of Medicines in Development With Goal of Further Expanding and Improving Treatment for People With Hepatitis C, Apr. 18, 2012.
Vertex and Alios BioPharma Announce Exclusive Worldwide Licensing Agreement for Two Nucleotide Drug Candidates, Broadening Vertex's Efforts to Develop New Combinations of Medicines for Hepatitis C, Vertex Pharmaceuticals, Press Release [online], Jun. 2011 [retrieved on Feb. 13, 2012]. Retrieved from the Internet:< URL: http://www.evaluatepharma.com/...%22%3a%5c%2224748 3%5c%22%2c%5c%22notSub%5c%22%3afalse%7d%22%7d% 2c%22_Type%22%3a1%7d>.
Vertex Announces 12-Week On-Treatment Data and SVR4 From Phase 2 Study of Interferon—Free (All-Oral) Treatment Regimen of INCIVEK, VX-222 and Ribavirin in People with Genotype 1 Hepatitis C, Feb. 23, 2012.
Vertex Announces Positive Results from Viral Kinetic Study of the Nucleotide Analogue ALS-2200 in People with Hepatitis C, Jul. 30, 2012.
Vertex Pharmaceutical Incorporated, Second Quarter Financial Results, Jul. 30, 2012.
Vertex Starts Global Phase 3b Study to Evaluate the Potential for People with Hepatitis C to Achieve a Viral Cure (SVR) with a Total Treatment Duration of 12 Weeks of INCIVEK Combination Therapy, Oct. 24, 2011.
Viral Cure Achieved without Interferon in up to 82% of Hepatitis C Patients (GT-1a & -1b*), Boehringer Ingelheim Press Release Archive [online], Apr. 2012 [retrieved on Aug. 9, 2012]. Retrieved from the Internet:< URL: http://www.boehringer-ingelheim.com/news/news_releases/press_releases/2012/19_april_2 . . . >.
VRUS Pharmasset Enters into a Clinical Collaboration Agreement with Tibotec Pharmaceuticals for a Combination Study in Patients Chronically Infected with Hepatitis C, Jul. 6, 2011.
VRUS Pharmasset Receives Notice of Allowance—USPTO to Grant Patent Covering the Anti-HCV Drug PSI-6130 and Its Active Metabolites, Jun. 26, 2008.
VRUS Pharmasset Reports Fiscal Year End 2011 Financial Results, Nov. 14, 2011.
White P.W., et al., "Preclinical Characterization of BI 201335, a C-terminal Carboxylic Acid Inhibitor of the Hepatitis C Virus NS3-NS4A Protease," Antimicrobial Agents and Chemotherapy, 2010, vol. 54 (11), pp. 4611-4618.
Yang J.C., et al., In Vitro Inhibition of Hepatic Bilirubin Transporters by the HCV NS3 Protease Inhibitor GS-9451 and In Vivo Correlation in Healthy Subjects, EASL 2012—Session Planner, Abstract 1216 [online], 2012 [retrieved on Apr. 4, 2012]. Retrieved from the Internet:< URL: http://www.abstractserver.com/easl2012/planner/index.php?go=abstract& . . . >.
Zeuzem S., et al., SVR4 and SVR12 with an Interferon-Free Regimen of B1201335 and BI207127, +/− Ribavirin, in Treatment-Naive Patients with Chronic Genotype-1 HCV Infection: Interim Results of Sound-C2, EASL 2012, Abstract [online], 2012 [retrieved on Apr. 27, 2012]. Retrieved from the Internet:< URL: http://mobile.ilcapp.eu/EASL_161/poster_24354/program.aspx>.
A Phase 2a Study of BMS-790052 and BMS-650032 in Combination Therapy with Japanese Subjects with Genotype 1 Chronic Hepatitis C (HCV) Virus Infection, NCT01051414 [online], Oct. 17, 2011 [retrieved on Jan. 17, 2013]. Retrieved from the Internet:< URL: http://clinicaltrials.gov/archive/NCT01051414/2011_10_17>.
An Exploratory Phase IIa, Randomized, Open-Label Trial to Investigate the Efficacy and Safety of 12 Weeks or 24 Weeks of TMC435 in Combination With PSI-7977 With or Without Ribavirin in Chronic Hepatitis C Genotype 1-Infected Prior Null Responders to Peginterferon/Ribavirin Therapy, NCT01466790 [online], Nov. 7, 2011 [retrieved on Jan. 17, 2013]. Retrieved from the Internet:< URL: http://clinicaltrials.gov/archive/NCT01466790/2011_11_07>.
Di Bisceglie A.M., et al., "VX-222 with TVR alone or in Combination with Peginterferon Alfa-2A and Ribavirin in Treatmentnaive Patients with Chronic Hepatitis C: Zenith Study Interim Results," EASL Poster Presentations, 2013.

GS 5885 Administered Concomitantly With GS-9451, Tegobuvir and Ribavirin (RBV) in Chronic Genotype 1 Hepatitis C Virus (HCV) Infection, NCT01353248 [online], May 12, 2011 [retrieved on Feb. 13, 2013]. Retrieved from the Internet:< URL: http://clinicaltrials.gov/archive/NCT01353248/2011_05_12>.
Incivek (Telaprevir) Film Coated Tablets, for Oral Use, 2011.
Non-Final Office Action mailed Nov. 27, 2012 for U.S. Appl. No. 13/603,006, filed Sep. 4, 2012.
Parallel, Open-Label, Randomized Study to Evaluate the Safety, Pharmacokinetics, and Pharmacodynamics of PSI-7977 in Combination with BMS-790052 with or without Ribavirin in Treatment Naive Subjects Chronically Infected with Hepatitis C Virus Genotypes 1, 2, or 3, NCT01359644 [online], Dec. 14, 2011 [retrieved on Jan. 17, 2013]. Retrieved from the Internet:< URL: http://clinicaltrials.gov/archive/NCT01359644/2011_12_14>.
Parallel, Open-Label, Randomized Study to Evaluate the Safety, Pharmacokinetics, and Pharmacodynamics of PSI-7977 in Combination with BMS-790052 with or without Ribavirin in Treatment Naive Subjects Chronically Infected with Hepatitis C Virus Genotypes 1, 2, or 3, NCT01359644 [online], Oct. 17, 2011 [retrieved on Jan. 17, 2013]. Retrieved from the Internet:< URL: http://clinicaltrials.gov/archive/NCT01359644/2011_10_17>.
Quantum: An International, Multi-center, Blinded, Randomized Study to Investigate Safety, Tolerability, Pharmacokinetics and Pharmacodynamics Following Administration of Regimens Containing PSI-352938, PSI-7977, and Ribavirin in Patients With Chronic Hepatitis C Virus (HCV) Infection, NCT01435044 [online], Sep. 14, 2011 [retrieved on Feb. 13, 2013]. Retrieved from the Internet:< URL: http://clinicaltrials.gov/archive/NCT01435044/2011_09_14>.
Victrelis (Boceprevir) Capsules for Oral Use, 2011.
Gane E.J., et al., Electron: 100% SVR Rate for Once-Daily Sofosbuvir Plus Ledipasvir Plus Ribavirin Given for 12 Weeks in Treatment-Naive and Previously Treated Patients With HCV GT 1, Conference Reports for NATAP, Mar. 3-6, 2013 [retrieved on Mar. 5, 2013]. Retrieved from the Internet:< URL: http://www.natap.org/2013/CROI/croi_07.htm>.
Bae A., et al., "Susceptibility of Treatment-naive Hepatitis C Virus (HCV) Clinical Isolates to HCV Protease Inhibitors," Antimicrobial Agents and Chemotherapy, 2010, vol. 54 (12), pp. 5288-5297.
Gao M., et al., "Chemical Genetics Strategy Identifies an HCV NS5A Inhibitor with a Potent Clinical Effect," Nature, 2010, vol. 465 (7294), pp. 96-100.
International Search Report and Written Opinion for Application No. PCT/US2012/061075, mailed on Mar. 21, 2013, 22 pages.
International Search Report and Written Opinion for Application No. PCT/US2012/061085, mailed on Mar. 21, 2013, 26 pages.
Non-Final Office Action mailed Mar. 21, 2013 for U.S. Appl. No. 13/656,012, filed Feb. 19, 2012.
Sofia M.J., et al., "Discovery of a Beta-D-2'-Deoxy-2'-Alpha-fluoro-2'-Beta-C-methyluridine Nucleotide Prodrug (PSI-7977) for the Treatment of Hepatitis C Virus," Journal of Medicinal Chemistry, 2010, vol. 53 (19), pp. 7202-7218.
A Multi-Center, Open-Labeled Exploratory Study to Investigate the Safety, Tolerability, Pharmacokinetics and Pharmacodynamics Following Oral Administration of PSI-7977 400 mg and Ribavirin for 12 Weeks with and without Pegylated Interferon in Treatment-Naive Patients with Chronic HCV Infection Genotype 2 or Genotype 3, NCT01260350 [online], May 7, 2012 [retrieved on Jan. 18, 2013]. Retrieved from the Internet:< URL: http://clinicaltrials.gov/archive/NCT01260350/2012_05_07>.
A Multi-Center, Open-Labeled Exploratory Study to Investigate the Safety, Tolerability, Pharmacokinetics and Pharmacodynamics Following Oral Administration of PSI-7977 400 mg and Ribavirin for 12 Weeks with and without Pegylated Interferon in Treatment-Naive Patients with Chronic HCV Infection Genotype 2 or Genotype 3, NCT01260350 [online], Dec. 14, 2010 [retrieved on Jan. 18, 2013]. Retrieved from the Internet:< URL: http://clinicaltrials.gov/archive/NCT01260350/2010_12_14>.
A Multi-Center, Open-Labeled Exploratory Study to Investigate the Safety, Tolerability, Pharmacokinetics and Pharmacodynamics Following Oral Administration of PSI-7977 400 mg and Ribavirin for 12 Weeks with and without Pegylated Interferon in Treatment-Naive Patients with Chronic HCV Infection Genotype 2 or Genotype 3, NCT01260350 [online], Jun. 15, 2011 [retrieved on Jan. 18, 2013]. Retrieved from the Internet:< URL: http://clinicaltrials.gov/archive/NCT01260350/2011_06_15>.
A Phase III, Randomized, Partially Double-Blind and Placebo-Controlled Study of BI 207127 in Combination with Faldaprevir and Ribavirin in Treatment-Naive Patients with Chronic Genotype 1 HCV Infection, NCT01732796 [online], Nov. 23, 2012 [retrieved on Jan. 21, 2013]. Retrieved from the Internet:< URL: http://clinicaltrials.gov/archive/NCT01732796/2012_11_23>.
A Pilot Study to Evaluate the Safety, Tolerability, Pharmacokinetics, and Antiviral Activity of ABT-450 with Ritonavir (ABT-450/r) Dosed in Combination with ABT-072 and Ribavirin (RBV), CTg M12-267 Initial Registration, IND/IDE No. 103526, 103122, Oct. 2010.
A Pilot Study to Evaluate the Safety, Tolerability, Pharmacokinetics, and Antiviral Activity of ABT-450 With Ritonavir (ABT-450/r) Dosed in Combination with ABT-072 and Ribavirin (RBV), NCT01221298 [online], Oct. 13, 2010 [retrieved on Dec. 18, 2012]. Retrieved from the Internet:< URL: http://clinicaltrials.gov/ct2/show/record/NCT01221298>.
A Randomized Controlled Study to Assess Safety, Tolerability and Efficacy of PSI-7977 alone or in Combination with RBV in HCV Genotype 1, Monoinfected Treatment Naive Participants, NCT01441180 [online], Sep. 26, 2011 [retrieved on Jan. 18, 2013]. Retrieved from the Internet:< URL: http://clinicaltrials.gov/archive/NCT01441180/2011_09_26>.
A Randomized, Open Label, Multi-Center Study to Evaluate the ANtiviral Activity, Safety, and Pharmacokinetics of ABT-450 with Ritonavir (ABT-450/r) in Combination with ABT-267 and/or ABT-333 with and without Ribavirin (RBV) in Treatment-Naive and Null Responder Subjects with Genotype 1 Chronic Hepatitis C Virus Infection, NCT01464827 [online], Nov. 3, 2011 [retrieved on Jan. 17, 2013]. Retrieved from the Internet:< URL: http://clinicaltrials.gov/archive/NCT01464827/2011_11_03>.
Abraham T.W., et al., "Synthesis and Biological Activity of Aromatic Amino Acid Phosphoramidates of 5-fluoro-2'-deoxyuridine and 1-beta-arabinofuranosylcytosine: Evidence of Phosphoramidase Activity," Journal of Medicinal Chemistry, 1996, vol. 39 (23), pp. 4569-4575.
An Open-label, Ascending Dose, Phase II Study to Evaluate Tolerability, Safety, Antiviral Activity and Pharmacokinetics of BI 207127 NA in Combination with BI 201335 NA and Ribavirin for 8 weeks in Treatment-Naive Japanese Patients with Genotype 1 Chronic Hepatitis C Virus Infection, NCT01528735 [online], Feb. 7, 2012 [retrieved on Jan. 21, 2013]. Retrieved from the Internet:< URL: http://clinicaltrials.gov/archive/NCT01528735/2012_02_07>.
An Open-Label Pilot Study to Evaluate the Antiviral Activity, Safety and Pharmacokinetics of ABT-450 with Ritonavir (ABT-450/r) Dosed in Combination with ABT-333 and Ribavirin (RBV) in Treatment-Naive and Non-Responder Subjects with Genotype 1 Chronic Hepatitis C Virus (HCV) Infection, NCT01306617 [online], Aug. 11, 2011 [retrieved on Jan. 17, 2013]. Retrieved from the Internet:< URL: http://clinicaltrials.gov/archive/NCT01306617/2011_08_11>.
An Open-Label Pilot Study to Evaluate the Antiviral Activity, Safety and Pharmacokinetics of ABT-450 with Ritonavir (ABT-450/r) Dosed in Combination with ABT-333 and Ribavirin (RBV) in Treatment-Naive Subjects with Genotype 1 Chronic Hepatitis C Virus (HCV) Infection, NCT01306617 [online], Mar. 1, 2011 [retrieved on Jan. 17, 2013]. Retrieved from the Internet:< URL: http://clinicaltrials.gov/archive/NCT01306617/2011_03_01>.
Co-pending U.S. Appl. No. 12/821,915, filed Jun. 23, 2010.
Co-pending U.S. Appl. No. 13/474,398, filed May 17, 2012.
Co-pending U.S. Appl. No. 13/474,411, filed May 17, 2012.
Cunningham M., et al., "Efficacy and Safety of Telaprevir in Patients with Genotype 1 Hepatitis C Infection," Therapeutic Advances in Gastroenterology, 2012, vol. 5 (2), pp. 139-151.
Foster G.R., et al., "Four-Week Treatment with GS-9256 and Tegobuvir (GS-9190), ± RBV ± PEG, Results in Enhanced Viral Suppression on Follow-up PEG/RBV Therapy, in Genotype 1A/1B HCV Patients," Poster Presentations [online], Mar. 31, 2011 [retrieved on Dec. 17, 2012]. Retrieved from the Internet:< URL: http://www1.easl.eu/easl2011/program/Posters/Abstract232.htm>.

Franciscus A., et al., Hepatitis C Treatments in Current Clinical Development, Dec. 19, 2011.

Harris S.A., et al., "Synthesis and Antiviral Evaluation of Phosphoramidate Derivatives of (E)-5-(2-bromovinyl)-2'-deoxyuridine," Antiviral Chemistry and Chemotherapy, 2001, vol. 12 (5), pp. 293-300.

Highleyman L., CROI: GS-7977 Rapidly Suppresses HCV, but Most Patients Relapse after Stopping Treatment [online], Mar. 7, 2012 [retrieved on Jan. 18, 2013]. Retrieved from the Internet: <URL: http://www.hivandhepatitis.com/hepatitis-c/hepatitis-c-topics/hcv-treatment/3487-croi-gs-7977>.

Invitation to Pay Additional Fees and Partial International Search Report for Application No. PCT/US2012/061075, mailed on Jan. 10, 2013, 10 pages.

Invitation to Pay Additional Fess and Partial International Search Report for Application No. PCT/US2012/061085, mailed on Jan. 3, 2013, 11 pages.

Jacobson I.M., et al., "VX-222, Telaprevir and Ribavirin in Treatment-Naive Patients with Genotype 1 Chronic Hepatitis C: Results of the ZENITH Study Interferon-Free Regimen," Hepatology, AASLD Abstracts, Oct. 2012, Abstract 231.

Lackey D.B., et al., "Enzyme-catalyzed Therapeutic Agent (ECTA) Design: Activation of the Antitumor ECTA Compound NB1011 by Thymidylate Synthase," Biochemical Pharmacology, 2001, vol. 61 (2), pp. 179-189.

Lawitz E., et al., "A 12-Week Interferon-Free Regimen of ABT-450/R, ABT-072, and Ribavirin was well Tolerated and Achieved Sustained Virologic Response in 91% Treatment-Naive HCV IL28B-CC Genotype-1-Infected Subjects," Journal of Hepatology (Oral Presentations), 2012, vol. 56, pp. S7 (Abs. 13).

McGuigan C., et al., "Synthesis and Evaluation of Some Masked Phosphate Esters of the Anti-herpesvirus Drug 882C (Netivudine) as Potential Antiviral Agents," Antiviral Chemistry and Chemotherapy, 1998, vol. 9 (3), pp. 233-243.

McPhee F., et al., "Characterization of Virologic Escape in HCV Genotype 1 Null Responders Receiving a Combination of the NS3 Protease Inhibitor BMS-650032 and NS5A Inhibitor BMS-790052," Journal of Hepatology, 2011, vol. 54, pp. S25-S29.

Membreno F.E., et al., "The HCV NS5B Nucleoside and Non-nucleoside Inhibitors," Clinics in Liver Disease, 2011, vol. 15 (3), pp. 611-626.

Open-Label, Multiple-Dose, Dose Escalation Study to Evaluate the Pharmacodynamics, Pharmacokinetics, and Safety of Coadministration of BMS-650032, BMS-790052, and BMS-791325 When Administered for 24 or 12 Weeks in Treatment-Naive Subjects Infected with Hepatitis C Virus Genotype 1, NCT01455090 [online], Oct. 18, 2011 [retrieved on Jan. 17, 2013]. Retrieved from the Internet:< URL: http://clinicaltrials.gov/archive/NCT01455090/2011_10_18>.

Parallel, Open-Label, Randomized Study to Evaluate the Safety, Pharmacokinetics, and Pharmacodynamics of PSI-7977 in Combination with BMS-790052 with or without Ribavirin in Treatment Naive Subjects Chronically Infected with Hepatitis C Virus Genotypes 1, 2, or 3, NCT01359644 [online], Jan. 5, 2012 [retrieved on Jan. 17, 2013]. Retrieved from the Internet:< URL: http://clinicaltrials.gov/archive/NCT01359644/2012_01_05>.

Partial European Search Report for Application No. EP12189195, mailed on Jan. 8, 2013, 7 pages.

Partial European Search Report for Application No. EP12189198, mailed on Jan. 10, 2013, 9 pages.

Safety, Antiviral Effect and Pharmacokinetics of BI 207127 in Combination with BI 201335 and with Ribavirin for 4 (Part 1) and with or without Ribavirin for 24-48 Weeks (Part 2) in Patients with Chronic HCV Genotype 1 Infection (Randomized, Open Label, Phase Ib/II), NCT01132313 [online], May 27, 2010 [retrieved on Jan. 17, 2013]. Retrieved from the Internet:< URL: http://clinicaltrials.gov/archive/NCT01132313/2010_05_27>.

Safety, Antiviral Effect and Pharmacokinetics of BI 207127 in Combination with BI 201335 and with Ribavirin for 4 Weeks (Part 1) and with or without Ribavirin for 16, 28 or 40 Weeks (Part 2) in Patients with Chronic HCV Genotype 1 Infection (Randomized, Open Label, Phase Ib/II), NCT01132313 [online], Oct. 19, 2011 [retrieved on Jan. 1, 2013]. Retrieved from the Internet:< URL: http://clinicaltrials.gov/archive/NCT01132313/2011_10_19>.

Sharma P., et al., "Interferon-free Treatment Regimens for Hepatitis C: Are We there Yet?," Gastroenterology, 2011, vol. 141 (6), pp. 1963-1967.

Sulkowski M., et al., "Potent Viral Suppression with All-Oral Combination of Daclatasvir (NS5A Inhibitor) and GS-7977 (Ns5B Inhibitor), +/−Ribavirin, in Treatment-Naive Patients with Chronic HCV GT1, 2, or 3," EASL 47th Annual Meeting, Apr. 18-22, 2012, Abstract 1422.

Tsantrizos Y.S., "TMC-435, an NS3/4A Protease Inhibitor for the Treatment of HCV Infection," Current Opinion in Investigational Drugs, 2009, vol. 10 (8), pp. 871-881.

Whalen L.J., et al., "Synthesis and Evaluation of Phosphoramidate Amino Acid-based Inhibitors of Sialyltransferases," Bioorganic and Medicinal Chemistry Letters, 2003, vol. 13 (2), pp. 301-304.

Yuodka B., et al., "Oligonucleotides and Nucleotide-Peptides XXXVII on the Mechanism of Hydrolysis of Uridylyl-(5->N)-Amino Acids. Intramolecular Catalysis by the Alpha-Carboxyl Group of Amino Acids," Journal of Carbohydrates Nucleosides Nucleotides, 1981, vol. 8 (6), pp. 519-535.

Zeuzem S., et al., "SVR4 and SVR12 with an Interferon-Free Regimen of BI201335 and BI207127, +/− Ribavirin, in Treatment-Naïve Patients with Chromic Genotype-1HCV Infection: Interim Results of Sound-C2," EASL 47th Annual Meeting, Apr. 18-22, 2012, Abstract 101.

* cited by examiner

METHODS FOR TREATING HCV

This application claims the benefit of U.S. Provisional Application No. 61/550,352 filed Oct. 21, 2011, U.S. Provisional Application No. 61/562,181 filed Nov. 21, 2011, U.S. Provisional Application No. 61/587,225 filed Jan. 17, 2012, U.S. Provisional Application No. 61/600,276 filed Feb. 17, 2012, U.S. Provisional Application No. 61/619,870 filed Apr. 3, 2012, and U.S. Provisional Application No. 61/656,251 filed Jun. 6, 2012.

FIELD OF THE INVENTION

The present invention relates to interferon-free treatment for hepatitis C virus (HCV).

BACKGROUND OF THE INVENTION

The HCV is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

Chronic HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often incomplete. Therefore, there is a need for new therapies to treat HCV infection.

BRIEF SUMMARY OF THE INVENTION

As one aspect of the present invention, methods for treating HCV infection in a subject are provided. The methods comprise administering at least two direct acting antiviral agents (DAAs) and ribavirin for a duration of no more than twelve weeks, or for another duration as set forth herein. Preferably, the duration of the treatment is twelve weeks. The duration of the treatment can also be no more than eight weeks. Preferably, the two or more direct acting antiviral agents (DAAs) and ribavirin are administered in amounts effective to provide a sustained virological response (SVR) or achieve another desired measure of effectiveness in a subject. The subject is not administered interferon during the treatment regimen. Put another way, the methods exclude the administration of interferon to the subject, thereby avoiding the side effects associated with interferon. In some embodiments, the methods further comprise administering an inhibitor of cytochrome P-450 (such as ritonavir) to the subject to improve the pharmacokinetics or bioavailability of one or more of the DAAs.

As another aspect, methods for treating HCV infection in a subject are provided. The methods comprise administering (a) therapeutic agent 1, (b) at least one polymerase inhibitor selected from the group consisting of therapeutic agent 2, therapeutic agent 3, and combinations thereof, (c) ribavirin and (d) an inhibitor of cytochrome P-450 to the subject for a duration of no more than twelve weeks, or for another duration as set forth herein (e.g., the treatment regimen can last a duration of for no more than 8 weeks). Preferably, therapeutic agent 1, the polymerase inhibitor(s), ribavirin and the inhibitor of cytochrome P-450 are administered in amounts effective to provide high rates of SVR or another measure of effectiveness in the subject. As non-limiting examples, therapeutic agent 1 and the inhibitor of cytochrome P-450 can be co-formulated and administered once daily, and the polymerase inhibitor(s) can be administered once daily or twice daily, and the treatment regimen preferably lasts for twelve weeks (the treatment regimen can also last, for example, for eight weeks).

As still another aspect, methods for treating a population of subjects having HCV infection are provided. The methods comprise administering at least two DAAs, together with ribavirin, to the subjects for a duration of no more than 12 weeks. Preferably, the at least two DAAs are administered to the subjects in amounts effective to result in SVR or another measure of effectiveness in at least about 50% of the population, preferably at least about 70% of the population.

In the foregoing methods as well as methods described hereinbelow, the DAAs can be selected from the group consisting of protease inhibitors, nucleoside or nucleotide polymerase inhibitors, non-nucleoside polymerase inhibitors, NS3B inhibitors, NS4A inhibitors, NS5A inhibitors, NS5B inhibitors, cyclophilin inhibitors, and combinations of any of the foregoing. For example, in some embodiments, the DAAs used in the present methods comprise or consist of at least one HCV protease inhibitor and at least one HCV polymerase inhibitor. The HCV polymerase inhibitor can be a nucleotide or nucleoside polymerase inhibitor or a non-nucleoside polymerase inhibitor. The HCV polymerase inhibitor can also be a non-nucleotide polymerase inhibitor.

In some embodiments, the HCV protease inhibitor is therapeutic agent 1 (described below) and the HCV polymerase inhibitor is therapeutic agent 2 and/or therapeutic agent 3 (also described below). By way of example, therapeutic agent 1 can be administered a total daily dose of from about 100 mg to about 250 mg, or administered at least once daily at a dose of from about 150 mg to about 250 mg, and therapeutic agent 2 is administered in a total daily dose of from about 300 mg to about 1800 mg or administered at least twice daily at doses from about 200 mg to about 400 mg. For some embodiments, the HCV protease inhibitor is therapeutic agent 1 and the non-nucleoside HCV polymerase inhibitor is therapeutic agent 3. By way of example, therapeutic agent 1 can be administered at a total daily dose of about 100 mg, alternatively about 200 mg, or alternatively about 250 mg; and therapeutic agent 3 is administered at a total daily dose of about 400 mg. Ritonavir (or another cytochrome P-450 3A4 inhibitor) can be co-administered with therapeutic agent 1 to improve the pharmacokinetics and bioavailability of therapeutic agent 1.

In some embodiments, the at least two DAAs comprise at least one HCV protease inhibitor and at least one NS5A inhibitor. Preferably, the HCV protease inhibitor is therapeutic agent 1 and the NS5A inhibitor is therapeutic agent 4. By way of example, therapeutic agent 1 can be administered at a total daily dosage from about 100 mg to about 250 mg, and therapeutic agent 4 can be administered in a total daily dose from about 25 mg to about 200 mg. Ritonavir (or another cytochrome P-450 3A4 inhibitor) can be co-administered with therapeutic agent 1 to improve the pharmacokinetics and bioavailability of therapeutic agent 1.

In the foregoing methods as well as methods described herein, the DAAs and ribavirin can be administered in any effective dosing schemes and/or frequencies, for example, they can each be administered daily. Each DAA can be administered either separately or in combination, and each DAA can be administered at least once a day, at least twice a day, or at least three times a day. Likewise, the ribavirin can be administered at least once a day, at least twice a day, or at least three times a day, either separately or in combination with one or more of the DAAs. In some preferred embodiments, therapeutic agent 3 is administered once daily (QD) or twice daily (BID), and therapeutic agent 1 is administered once daily.

In some aspects, the present technology provides a method for treating HCV infection comprising administering to a subject in need thereof at least two DAAs and ribavirin for a duration of no more than twelve weeks, wherein the subject is not administered with interferon during said duration. In some aspects, the at least two DAAs and ribavirin are administered in an amount effective to result in SVR. Some methods further comprise administering an inhibitor of cytochrome P450 to the subject. In some aspects, the duration is no more than eight weeks.

In some aspects of the present technology, the at least two direct acting antiviral agents comprise (i) Compound 1 or a pharmaceutically acceptable salt thereof, which is co-administered or co-formulated with ritonavir, and (ii) Compound 2 or a pharmaceutically acceptable salt thereof.

In other aspects, the at least two direct acting antiviral agents comprise (i) Compound 1 or a pharmaceutically acceptable salt thereof, which is co-administered or co-formulated with ritonavir, and (ii) Compound 3 or a pharmaceutically acceptable salt thereof.

In yet another aspect, the at least two direct acting antiviral agents comprise (i) Compound 1 or a pharmaceutically acceptable salt thereof, which is co-administered or co-formulated with ritonavir, and (ii) compound 4 or a pharmaceutically acceptable salt thereof.

In yet a further aspect, the at least two direct acting antiviral agents comprise (i) Compound 1 or a pharmaceutically acceptable salt thereof, which is co-administered or co-formulated with ritonavir, (ii) Compound 2 or a pharmaceutically acceptable salt thereof, and (iii) compound 4 or a pharmaceutically acceptable salt thereof.

In yet another aspect, the at least two direct acting antiviral agents comprises a drug combination selected from the group consisting of: a combination of PSI-7977 and PSI-938, a combination of BMS-790052 and BMS-650032, a combination of GS-5885 and GS-9451, a combination of GS-5885, GS-9190 and GS-9451, a combination of BI-201335 and BI-27127, a combination of telaprevir and VX-222, a combination of PSI-7977 and TMC-435, and a combination of danoprevir and R7128. In yet another aspect, the at least two direct acting antiviral agents comprises a combination of PSI-7977 and BMS-790052 (daclatasvir). In yet another aspect, the at least two direct acting antiviral agents comprises a combination of PSI-7977 and BMS-650032 (asunaprevir). In still another aspect, the at least two direct acting antiviral agents comprises a combination of PSI-7977, BMS-650032 (asunaprevir) and BMS-790052 (daclatasvir).

In other aspects, the present technology provides a method for treating HCV infection in a subject comprising administering (a) therapeutic agent 1, (b) at least one polymerase inhibitor selected from the group consisting of therapeutic agent 2, therapeutic agent 3 and combinations thereof, (c) ribavirin and (d) an inhibitor of cytochrome P450 to the subject and for a duration of no more than twelve weeks, wherein the therapeutic agent 1, the at least one polymerase inhibitor, the ribavirin and the inhibitor of cytochrome P450 are administered in amounts effective to result in sustained virological response (SVR) in the subject.

In yet another aspect, the present technology provides a method for treating a population of subjects having HCV infection, the method comprising administering at least two DAAs to the subjects for a duration of no more than 12 weeks, wherein the at least two DAAs are administered to the subjects in amounts and for a duration effective to provide a SVR in at least about 70% of the population.

In another aspect, the present technology features a combination of at least two DAAs for use in treating HCV infection, wherein the duration of the treatment regimen is no more than twelve weeks (e.g., the duration being 12 weeks; or the duration being 11, 10, 9, 8, 7, 6, 5, 4, or 3 weeks). The treatment comprises administering the at least two DAAs to a subject infected with HCV. Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may also include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder, a partial responder or a relapser), or not a candidate for interferon treatment.

In another aspect, the present technology features a combination of Compound 1 (or a pharmaceutically acceptable salt thereof) and Compound 2 (or a pharmaceutically acceptable salt thereof) for use in treating HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon; and ritonavir or another CYP3A4 inhibitor (e.g., cobicistat) is administered with Compound 1 (or the salt thereof) to improve the pharmacokinetics of the latter. Compound 1 (or the salt thereof) and Compound 2 (or the salt thereof) can be administered concurrently or sequentially. For example, Compound 1 (or the salt thereof) can be administered once daily, together with ritonavir or another CYP3A4 inhibitor (e.g., cobicistat), and Compound 2 (or the salt thereof) can be administered twice daily. For yet another example, Compound 1 (or the salt thereof) and ritonavir (or another CYP3A4 inhibitor, e.g., cobicistat) are co-formulated in a single composition and administered concurrently (e.g., once daily). For yet another example, Compound 1 (or the salt thereof), co-formulated with ritonavir (or another CYP3A4 inhibitor, e.g., cobicistat), is administered once daily, and Compound 2 (or the salt thereof) is administered twice daily. As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder infected (e.g., a null responder) with HCV genotype 1.

In another aspect, the present technology features a combination of Compound 1 (or a pharmaceutically acceptable salt thereof) and Compound 3 (or a pharmaceutically acceptable salt thereof) for use in treating HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon; and ritonavir or another CYP3A4 inhibitor (e.g., cobicistat) is administered with Compound 1 (or the salt thereof) to improve the pharmacokinetics of the latter. Compound 1 (or the salt thereof) and Compound 3 (or the salt thereof) can be administered concurrently or sequentially. For example, Compound 1 (or the salt thereof) can be administered once daily, together with ritonavir or another CYP3A4 inhibitor (e.g., cobicistat), and Compound 3 (or the salt thereof) can be administered twice daily. For another example, Compound 1 (or the salt thereof) and Compound 3 (or the salt thereof) are administered once daily. For yet another example, Compound 1 (or the salt thereof) and ritonavir (or another CYP3A4 inhibitor, e.g., cobicistat) are co-formulated in a single composition and administered concurrently (e.g., once daily). For yet another example, Compound 1 (or the salt thereof), ritonavir (or another CYP3A4 inhibitor, e.g., cobicistat), and Compound 3 (or the salt thereof) are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1.

In another aspect, the present technology features a combination of Compound 1 (or a pharmaceutically acceptable salt thereof) and compound 4 (or a pharmaceutically acceptable salt thereof) for use in treating HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon; and ritonavir or another CYP3A4 inhibitor (e.g., cobicistat) is administered with Compound 1 (or the salt thereof) to improve the pharmacokinetics of the latter. Compound 1 (or the salt thereof) and compound 4 (or the salt thereof) can be administered concurrently or sequentially. For example, Compound 1 (or the salt thereof) can be administered once daily, together with ritonavir or another CYP3A4 inhibitor (e.g., cobicistat), and compound 4 (or the salt thereof) can be administered twice daily. For another example, Compound 1 (or the salt thereof) and compound 4 (or the salt thereof) are administered once daily. For yet another example, Compound 1 (or the salt thereof) and ritonavir (or another CYP3A4 inhibitor, e.g., cobicistat) are co-formulated in a single composition and administered concurrently (e.g., once daily). For yet another example, Compound 1 (or the salt thereof), ritonavir (or another CYP3A4 inhibitor, e.g., cobicistat), and compound 4 (or the salt thereof) are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1.

In another aspect, the present technology features a combination of Compound 1 (or a pharmaceutically acceptable salt thereof), Compound 2 (or a pharmaceutically acceptable salt thereof), and compound 4 (or a pharmaceutically acceptable salt thereof) for use in treating HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon; and ritonavir or another CYP3A4 inhibitor (e.g., cobicistat) is administered with Compound 1 (or the salt thereof) to improve the pharmacokinetics of the latter. Compound 1 (or the salt thereof), Compound 2 (or the salt thereof), and compound 4 (or the salt thereof) can be administered concurrently or sequentially. For example, Compound 1 (or the salt thereof) can be administered once daily, together with ritonavir or another CYP3A4 inhibitor (e.g., cobicistat), and compound 4 (or the salt thereof) can be administered once daily, and Compound 2 (or the salt thereof) can be administered twice daily. For yet another example, Compound 1 (or the salt thereof), compound 4 (or the salt thereof), and ritonavir (or another CYP3A4 inhibitor, e.g., cobicistat) are co-formulated in a single composition and administered concurrently (e.g., once daily). For yet another example, Compound 1 (or the salt thereof), ritonavir (or another CYP3A4 inhibitor, e.g., cobicistat), and compound 4 (or the salt thereof) are co-formulated in a single composition and administered concurrently (e.g., once daily), and Compound 2 (or the salt thereof) are administered twice daily. As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 12 weeks, and the subject being treated is a naïve patient infected with HCV genotype 1. In another example, the treatment lasts for 11 weeks, and the subject being treated is a naïve patient infected with HCV genotype 1.

In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1.

In another aspect, the present technology features a combination of at least two DAAs for use in treating HCV infection, wherein said combination comprises a combination selected from:

a combination of PSI-7977 and PSI-938,
a combination of BMS-790052 and BMS-650032,
a combination of GS-5885 and GS-9451,
a combination of GS-5885, GS-9190 and GS-9451,
a combination of BI-201335 and BI-27127,
a combination of telaprevir and VX-222,
a combination of PSI-7977 and TMC-435, and
a combination of danoprevir and R7128.

The treatment comprises administering the DAA combination to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may also include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment.

In yet another aspect, the present technology features a combination of at least two DAAs for use in treating HCV infection, wherein said combination comprises a combination selected from:

a combination of PSI-7977 and BMS-790052
a combination of PSI-7977 and BMS-650032,
a combination of PSI-7977, BMS-790052 and BMS-650032,
a combination of INX-189 and BMS-790052
a combination of INX-189 and BMS-650032, or
a combination of INX-189, BMS-790052 and BMS-650032.

The treatment comprises administering the DAA combination to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment.

In still another aspect, the present technology features PSI-7977, or a combination of at least two DAAs, for use in treating HCV infection, wherein said combination comprises a combination selected from:

a combination of mericitabine and danoprevir,
a combination of INX-189, daclatasvir and BMS-791325, and
a combination of PSI-7977 and GS-5885.

The treatment comprises administering PSI-7977 or the DAA combination to a subject infected with HCV. The duration of the treatment regimen is no more than twelve weeks (e.g., the duration being 12 weeks; or the duration being 11, 10, 9, 8, 7, 6, 5, 4, or 3 weeks). For example, the duration of the treatment regimen is no more than eight weeks (e.g., the duration being 8 weeks; or the duration being 7, 6, 5, 4, or 3 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment.

In still another aspect, the present technology features PSI-7977, or a combination of at least two DAAs, for use in treating HCV infection, wherein said combination comprises a combination selected from:

a combination of mericitabine and danoprevir, a combination of INX-189, daclatasvir and BMS-791325, and a combination of PSI-7977 and GS-5885.

The treatment comprises administering PSI-7977 or the DAA combination to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment.

In still another aspect, the present technology features a combination of at least two DAAs, for use in treating HCV infection, wherein said combination comprises a combination selected from:

a combination of tegobuvir and GS-9256, a combination of BMS-791325, asunaprevir and daclatasvir, and a combination of TMC-435 and daclatasvir.

The treatment comprises administering the DAA combination to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment.

In yet another aspect, the present technology features a combination of PSI-7977 and BMS-790052 for use in treating HCV infection. The treatment comprises administering the DAA combination to a subject infected with HCV. The duration of the treatment can last, for example, no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2.

In yet another example, the treatment lasts for 8 weeks, and the subject being treated is a naïve patient infected with HCV genotype 2. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1.

In yet another aspect, the present technology features a combination of PSI-7977 and TMC-435 for use in treating HCV infection. The treatment comprises administering the DAA combination to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1.

In yet another aspect, the present technology features a combination of danoprevir and mercitabine for use in treating HCV infection. The treatment comprises administering the DAA combination to a subject infected with HCV. The duration of the treatment regimen is no more than sixteen weeks (e.g., the duration being 16 weeks; or the duration being 14, 12 or 10 weeks). The duration of the treatment regimen may also be less than 10 weeks. The treatment includes administering ribavirin but does not include administering interferon. The treatment also includes co-administering ritonavir or another CYP3A4 inhibitor (e.g., cobicistat) with danoprevir to improve the pharmacokinetics of danoprevir. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 16 weeks, and the subject being treated is a naïve patient infected with HCV genotype 1. In another example, the treatment lasts for 15 weeks, and the subject being treated is a naïve patient infected with HCV genotype 1. In still another example, the treatment lasts for 14 weeks, and the subject being treated is a naïve patient infected with HCV genotype 1. In yet another example, the treatment lasts for 13 weeks, and the subject being treated is a naïve patient infected with HCV genotype 1. In yet another example, the treatment lasts for 12 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 16 weeks, and the subject being treated is a naïve patient infected with HCV genotype 3. In another example, the treatment lasts for 15 weeks, and the subject being treated is a naïve patient infected with HCV genotype 3. In still another example, the treatment lasts for 14 weeks, and the subject being treated is a naïve patient infected with HCV genotype 3. In yet another example, the treatment lasts for 13 weeks, and the subject being treated is a naïve patient infected with HCV genotype 3. In yet another example, the treatment lasts for 12 weeks, and the subject being treated is a naïve patient infected with HCV genotype 3. In yet another example, the treatment lasts for 16 weeks, and the subject being treated is a non-responder (e.g., a null responder) infected with HCV genotype 1. In another example, the treatment lasts for 15 weeks, and the subject being treated is a non-responder (e.g., a null responder) infected with HCV genotype 1. In still another example, the treatment lasts for 14 weeks, and the subject being treated is a non-responder (e.g., a null responder) infected with HCV genotype 1. In yet another example, the treatment lasts for 13 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 1.

In yet another aspect, the present technology features a combination of INX-189, daclatasvir and BMS-791325 for use in treating HCV infection. The treatment comprises administering the DAA combination to a subject infected with HCV. The duration of the treatment regimen is no more than sixteen weeks (e.g., the duration being 16 weeks; or the duration being 14, 12 or 10 weeks). The duration of the treatment regimen may also be less than 10 weeks. The treatment includes administering ribavirin but does not include administering interferon. The treatment may include administering ritonavir or another CYP3A4 inhibitor (e.g., cobicistat) if one of the DAAs requires pharmacokinetic enhancement. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 16 weeks, and the subject being treated is a naïve patient infected with HCV genotype 1. In another example, the treatment lasts for 15 weeks, and the subject being treated is a naïve patient infected with HCV genotype 1. In still another example, the treatment lasts for 14 weeks, and the subject being treated is a naïve patient infected with HCV genotype 1. In yet another example, the treatment lasts for 13 weeks, and the subject being treated is a naïve patient infected with HCV genotype 1. In yet another example, the treatment lasts for 12 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 16 weeks, and the subject being treated is a naïve patient infected with HCV genotype 3. In another example, the treatment lasts for 15 weeks, and the subject being treated is a naïve patient infected with HCV genotype 3. In still another example, the treatment lasts for 14 weeks, and the subject being treated is a naïve patient infected with HCV genotype 3. In yet another example, the treatment lasts for 13 weeks, and the subject being treated is a naïve patient infected with HCV genotype 3. In yet another example, the treatment lasts for 12 weeks, and the subject being treated is a naïve patient infected with HCV genotype 3. In yet another example, the treatment lasts for 16 weeks, and the subject being treated is a non-responder (e.g., a null responder) infected with HCV genotype 1. In another example, the treatment lasts for 15 weeks, and the subject being treated is a non-responder (e.g., a null responder) infected with HCV genotype 1. In still another example, the treatment lasts for 14 weeks, and the subject being treated is a non-responder (e.g., a null responder) infected with HCV genotype 1. In yet another example, the treatment lasts for 13 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 1.

In yet another aspect, the present technology features a combination of PSI-7977 and GS-5885 for use in treating HCV infection. The treatment comprises administering the DAA combination to a subject infected with HCV. The duration of the treatment regimen is no more than sixteen weeks (e.g., the duration being 16 weeks; or the duration being 14, 12 or 10 weeks). The duration of the treatment regimen may also be less than 10 weeks. The treatment includes administering ribavirin but does not include administering interferon. The treatment may include administering ritonavir or another CYP3A4 inhibitor (e.g., cobicistat) if one of the DAAs requires pharmacokinetic enhancement. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responder (e.g., a null responder), or not a candidate for interferon treatment. In one example, the treatment lasts for 16 weeks, and the subject being treated is a naïve patient infected with HCV genotype 1. In another example, the treatment lasts for 15 weeks, and the subject being treated is a naïve patient infected with HCV genotype 1. In still another example, the treatment lasts for 14 weeks, and the subject being treated is a naïve patient infected with HCV genotype 1. In yet another example, the treatment lasts for 13 weeks, and the subject being treated is a naïve patient infected with HCV genotype 1. In yet another example, the treatment lasts for 12 weeks, and the subject being treated is a naïve patient infected with HCV genotype 1. In yet another example, the treatment lasts for 12 weeks, and the subject being treated is a naïve patient infected with HCV genotype 2. In another example, the treatment lasts for 11 weeks, and the subject being treated is a naïve patient infected with HCV genotype 2. In still another example, the treatment lasts for 10 weeks, and the subject being treated is a naïve patient infected with HCV genotype 2. In yet another example, the treatment lasts for 9 weeks, and the subject being treated is a naïve patient infected with HCV genotype 2. In yet another example, the treatment lasts for 8 weeks, and the subject being treated is a naïve patient infected with HCV genotype 2. In yet another example, the treatment lasts for 16 weeks, and the subject being treated is a naïve patient infected with HCV genotype 3. In another example, the treatment lasts for 15 weeks, and the subject being treated is a naïve patient infected with HCV genotype 3. In still another example, the treatment lasts for 14 weeks, and the subject being treated is a naïve patient infected with HCV genotype 3. In yet another example, the treatment lasts for 13 weeks, and the subject being treated is a naïve patient infected with HCV genotype 3. In yet another example, the treatment lasts for 12 weeks, and the subject being treated is a naïve patient infected with HCV genotype 3. In yet another example, the treatment lasts for 16 weeks, and the subject being treated is a non-responder (e.g., a null responder) infected with HCV genotype 1. In another example, the treatment lasts for 15 weeks, and the subject being treated is a non-responder (e.g., a null responder) infected with HCV genotype 1. In still another example, the treatment lasts for 14 weeks, and the subject being treated is a non-responder (e.g., a null responder) infected with HCV genotype 1. In yet another example, the treatment lasts for 13 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 1.

In another aspect, the present invention features methods for treatment of HCV infection, wherein the methods comprise administering to a subject in need thereof at least two direct acting antiviral agents (DAAs) and ribavirin, and the treatment does not include administration of interferon to the subject. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In one embodiment of this aspect of the invention, the at least two DAAs comprise (i) Compound 1 or a pharmaceutically acceptable salt thereof, and (ii) Compound 2 or a pharmaceutically acceptable salt thereof, and said method further comprises administering ritonavir to the subject. Ritonavir improves the pharmacokinetics or drug exposure of Compound 1. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In another embodiment of this aspect of the invention, the at least two DAAs comprise (i) Compound 1 or a pharmaceutically acceptable salt thereof, and (ii) Compound 4 or a pharmaceutically acceptable salt thereof, and the method further comprises administering ritonavir to the subject to improve the pharmacokinetics or drug exposure of Compound 1. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In another embodiment of this aspect of the invention, the at least two DAAs comprise (i) Compound 1 or a pharmaceutically acceptable salt thereof, (ii) Compound 2 or a pharmaceutically acceptable salt thereof, and (iii) Compound 4 or a pharmaceutically acceptable salt thereof, and the method further comprises administering ritonavir to the subject to improve the pharmacokinetics or drug exposure of Compound 1. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV protease inhibitor and a HCV polymerase inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV protease inhibitor and a non-nucleoside or non-nucleotide HCV polymerase inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV protease inhibitor and a nucleoside or nucleotide HCV polymerase inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV protease inhibitor and a HCV NS5A inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV polymerase inhibitor and a HCV NS5A inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV non-nucleoside or non-nucleotide polymerase inhibitor and a HCV NS5A inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a HCV nucleoside or nucleotide polymerase inhibitor and a HCV NS5A inhibitor. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise PSI-7977 and TMC-435. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise PSI-7977 and daclatasvir. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise PSI-7977 and GS-5885. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise mericitabine and danoprevir. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise BMS-790052 and BMS-650032. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1b. As a non-limiting example, the subject being treatment is infected with HCV genotype 1a. As another non-limiting example, the subject being treatment is infected with HCV genotype 3.

In yet another embodiment of this aspect of the invention, the at least two DAAs comprise INX-189, daclatasvir and BMS-791325. The treatment can last, for example and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another aspect, the present invention features methods for treatment of a treatment-naïve subject with HCV genotype 1 infection, wherein the method comprises administering to said patient PSI-7977 and ribavirin, and the treatment does not include administration of interferon to the subject. The treatment can last, for example and without limitation, for no more than 12 weeks, such as 8, 9, 10, 11 or 12 weeks. Preferably, the treatment lasts for 12 weeks. The treatment can also last for 8 weeks. Preferably, the subject being treated is infected with genotype 1a. More preferably, the subject being treated is a naïve patient infected with genotype 1. The subject being treated can also be a treatment-experienced patient or an interferon non-responder (e.g., a null responder), and/or is infected with HCV genotype 3. In one example, the treatment lasts for 12 weeks, and the subject being treated is a naïve patient infected with genotype 1. In another example, the treatment lasts for 11 weeks, and the subject being treated is a naïve patient infected with genotype 1. In still another example, the treatment lasts for 10 weeks, and the subject being treated is a naïve patient infected with genotype 1. In yet another example, the treatment lasts for 9 weeks, and the subject being treated is a naïve patient infected with genotype 1. In yet another example, the treatment lasts for 8 weeks, and the subject being treated is a naïve patient infected with genotype 1. The present invention also features PSI-7977 or a pharmaceutical acceptable salt thereof for use in any treatment described in this aspect of the invention.

A treatment regimen of the present technology generally constitutes a complete treatment regimen, i.e., no subsequent interferon-containing regimen is intended. Thus, a treatment or use described herein generally does not include any subsequent interferon-containing treatment.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description

DETAILED DESCRIPTION OF THE INVENTION

Figure 1:
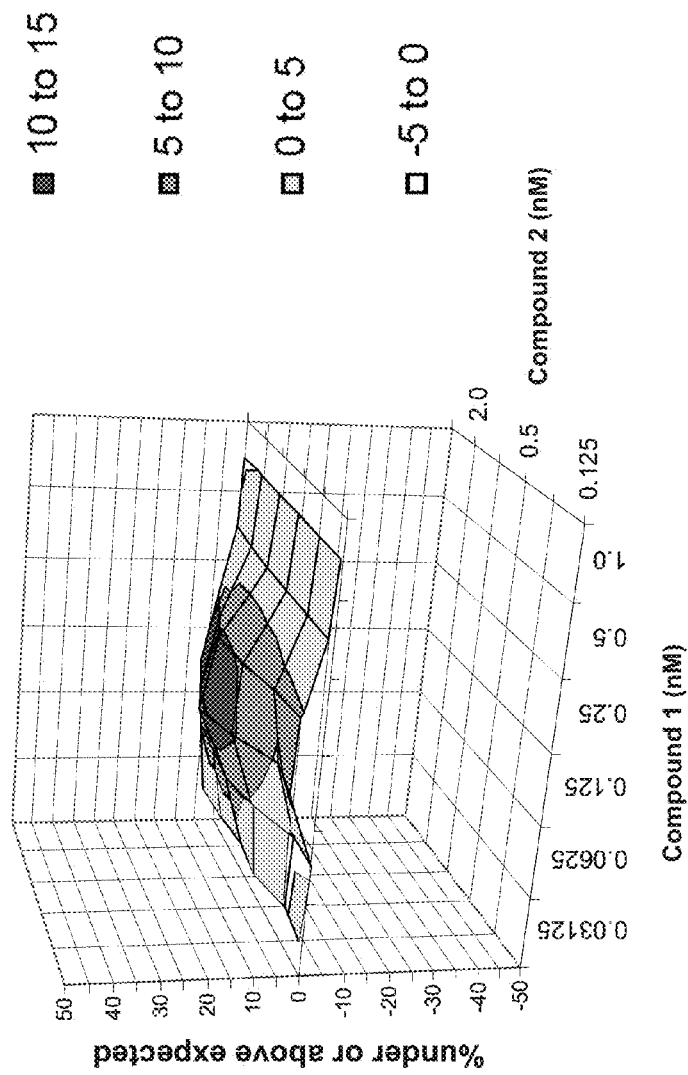
FIG. 1 is a 3-D surface plot illustrating deviations from expected inhibitory effects from varying concentrations of Compound 1 and Compound 2 in a genotype 1b HCV replicon assay.

The present methods can include administering therapeutic agent 1 to a subject. Therapeutic agent 1 is Compound 1

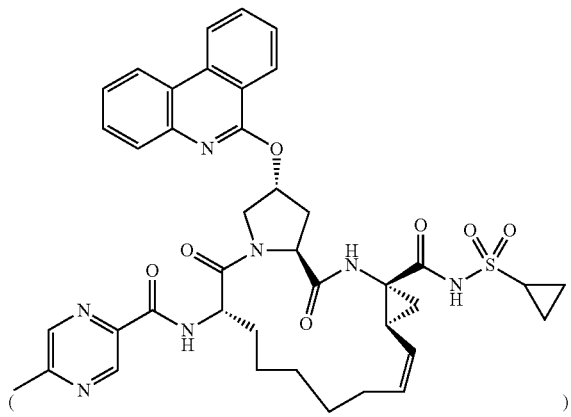 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

or a pharmaceutically acceptable salt thereof. Compound 1 is also known as (2R,6S,13aS,14aR,16aS,Z)—N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. Compound 1 is a potent HCV protease inhibitor. The synthesis and formulation of Compound 1 are described in U.S. Patent Application Publication No. 2010/0144608, U.S. Provisional Application Ser. No. 61/339,964 filed on Mar. 10, 2010, and U.S. Patent Application Publication No. 2011/0312973 filed on Mar. 8, 2011. All of these applications are incorporated herein by reference in their entireties. Therapeutic agent 1 includes various salts of Compound 1. Therapeutic agent 1 may be administered in any suitable amount such as, for example, in doses of from about 0.01 to about 50 mg/kg body weight, alternatively from about 0.1 to about 25 mg/kg body weight. As non-limiting examples, therapeutic agent 1 may be administered in a total daily dose amount of from about 50 mg to about 250 mg, preferably from about 100 mg to about 250 mg, and includes, but is not limited to, for example, about 50 mg, about 75 mg, about 100 mg, about 125 mg, about 150 mg, about 175 mg, about 200 mg, about 225 mg, about 250 mg and suitable amounts there between.

In preferred embodiments, ritonavir or another inhibitor of cytochrome P-450 is co-administered with therapeutic agent 1 to improve the pharmacokinetics of Compound 1.

The present methods can include administering therapeutic agent 2 to a subject. Therapeutic agent 2 is Compound 2 or a salt thereof.

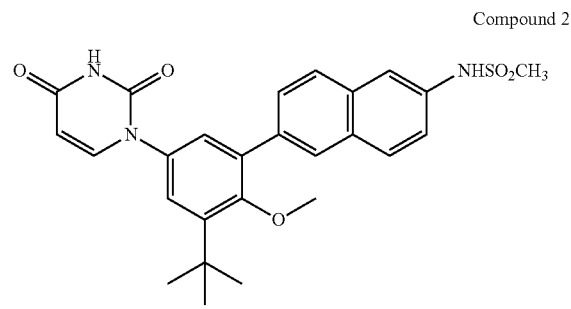

Compound 2 is also known N-(6-(3-tert-butyl-5-(2,4-dioxo-3,4-dihydropyrimidin-1(2H)-yl)-2-methoxyphenyl)naphthalen-2-yl)methanesulfonamide. As described in, for example, International Publication No. WO2009/039127, therapeutic agent 2 includes various salts of Compound 2, such as sodium salts, potassium salts, and choline salts. Therapeutic agent 2 also includes crystalline forms of Compound 2 and its salts such as solvate, hydrate, and solvent-free crystalline forms of Compound 2 and its salts. Compositions comprising therapeutic agent 2 can be prepared as described in, for example, International Publication No. WO2009/039127 which is incorporated by reference herein.

Therapeutic agent 2 may be administered as a free acid, salt or particular crystalline form of Compound 2. In some embodiments, therapeutic agent 2 is administered as a sodium salt. Therapeutic agent 2 may be administered in any suitable amount such as, for example, in doses of from about 5 mg/kg to about 30 mg/kg. As non-limiting examples, therapeutic agent 2 may be administered in a total daily dose amount of from about 300 mg to about 1800 mg, or from about 400 mg to about 1600 mg, or from about 600 mg to about 1800 mg, or from about 800 mg to about 1600 mg or any amounts there between. In some embodiments, the total daily dosage amount for therapeutic agent 2 is about 600 mg. In some embodiments, the total daily dosage amount for therapeutic agent 2 is about 800 mg. In some embodiments, the total daily dosage amount for therapeutic agent 2 is about 1200 mg. In some embodiments, the total daily dosage amount for therapeutic agent 2 is about 1600 mg.

The present methods can include administering therapeutic agent 3 or a salt thereof to a subject. Therapeutic agent 3 is Compound 3 or a salt thereof.

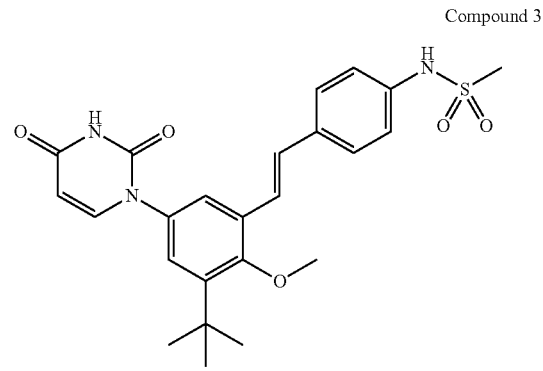 [SMILES: COc1c(/C=C/c2ccc(NS(C)(=O)=O)cc2)cc(-n2ccc(=O)[nH]c2=O)cc1C(C)(C)C]

Compound 3 is also known as (E)-N-(4-(3-tert-butyl-5-(2,4-dioxo-3,4-dihydropyrimidin-1(2H)-yl)-2-methoxystyryl)phenyl)methanesulfonamide. As described in, for example, International Publication No. WO2009/039127, therapeutic agent 3 includes various salts of Compound 3, such as sodium salts, potassium salts, and choline salts. Therapeutic agent 3 also includes crystalline forms of Compound 3 and its salts such as solvate, hydrate, and solvent-free crystalline forms of Compound 3 and its salts. Compositions comprising therapeutic agent 3 can be prepared as described in, for example, International Publication No. WO2009/039127 which is incorporated by reference herein.

Therapeutic agent 3 may be administered as a free acid, salt or particular crystalline form of Compound 3. In some embodiments, Compound 3 is administered as a potassium salt. Therapeutic agent 3 may be administered in any suitable amount such as, for example, in doses of from about 0.5 mg/kg to about 15 mg/kg or from about 1 mg/kg to about 10 mg/kg. As non-limiting examples, therapeutic agent 3 may be administered in a total daily dose amount of from about 100 mg to about 600 mg. In some embodiments, the total daily dosage amount for therapeutic agent 3 is about 300 mg. In some embodiments, the total daily dosage amount for therapeutic agent 3 is about 320 mg. In some embodiments, the total daily dosage amount for therapeutic agent 3 is about 400 mg. In some embodiments, the total daily dosage amount for therapeutic agent 3 is about 600 mg.

The present methods can include administering therapeutic agent 4 or a salt thereof to a subject. Therapeutic agent 4 is compound 4 or a salt thereof.

ribavirin include COPEGUS®, REBETOL® and RIBASPHERE®. An exemplary pro-drug of ribavirin is taribavirin having the chemical name of 1-β-D-ribofuranosyl-1,2,4-triazole-3-carboxamidine. Ribavirin and taribavirin may be administered in accordance with ribavirin and taribavirin administration well known in the art. In some embodiments, COPEGUS® or REBETOL® is administered in a daily dosage amount of from about 500 mg to about 1500 mg in one dose or in divided doses. In some embodiments, COPEGUS® or REBETOL® is administered in a daily dosage amount of about 800 mg. In some embodiments, REBETOL® is administered in a daily dosage amount of about 1000 mg. In some embodiments, COPEGUS® or REBETOL® is administered in a daily dosage amount of about 1200 mg. In some embodiments, REBETOL® is administered in a daily dosage amount of about 1400 mg. Suitable dosages of ribavirin are dependent on the weight of the subject, for example about 1000-1200 mg. Suitable total daily dosages of ribavirin include, but are not limited to about 400 mg to about 1400 mg a day, alternatively about 800 mg to about 1400 mg per day, alternatively about 400 mg to about 1200 mg, alternatively about 800 mg to about 1200 mg.

The current standard of care (SOC) for the treatment of HCV includes a course of treatment of interferon, e.g. pegylated interferon (e.g., pegylated interferon-alpha-2a or pegylated interferon-alpha-2b, such as PEGASYS by Roche, or PEG-INTRON by Schering-Plough) and the antiviral drug Compound 4

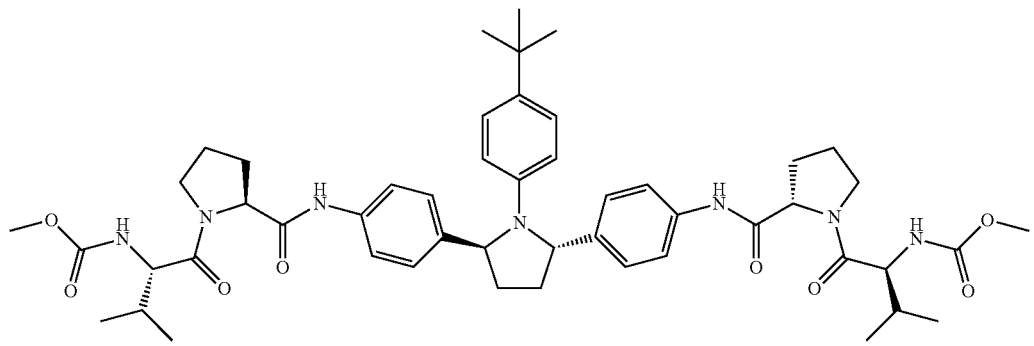

Compound 4 is also known as dimethyl (2S,2'S)-1,1'-((2S,2'S)-2,2'-(4,4'-((2S,5S)-1-(4-tert-butylphenyl)pyrrolidine-2,5,diyl)bis(4,1-phenylene))bis(azane diyl)bis(oxomethylene)bis(pyrrolidine-2,1-diyl)bis(3-methyl-1-oxobutane-2,1-diyl) dicarbamate. Compound 4 can be prepared as described in, for example, U.S. Publication No. 2010/0317568, which is incorporated herein by reference.

Therapeutic agent 4 may be administered as a free acid, or a salt form. Therapeutic agent 4 may be administered in any suitable amount such as, for example, in doses of from about 0.1 mg/kg to about 200 mg/kg body weight, or from about 0.25 mg/kg to about 100 mg/kg, or from about 0.3 mg/kg to about 30 mg/kg. As non-limiting examples, therapeutic agent 4 may be administered in a total daily dose amount of from about 5 mg to about 300 mg, or from about 25 mg to about 200 mg, or from about 25 mg to about 50 mg or any amounts there between. In some embodiments, the total daily dosage amount for therapeutic agent 4 is about 25 mg.

The at least two DAAs may also be co-administered with ribavirin, or a pro-drug thereof, in the same or separate pharmaceutical compositions. Ribavirin may include any suitable form or formulation of ribavirin. Exemplary formulations of ribavirin (e.g., COPEGUS by Roche, REBETOL by Schering-Plough, or RIBASPHERE by Three Rivers Pharmaceuticals). The treatment often lasts for 24-48 weeks, depending on hepatitis C virus genotype. Other interferons include, but are not limited to, interferon-alpha-2a (e.g., Roferon-A by Roche), interferon-alpha-2b (e.g., Intron-A by Schering-Plough), and interferon alfacon-1 (consensus interferon) (e.g., Infergen by Valeant). Less than 50% of patients with chronic HCV infection with genotype 1 virus respond to this therapy. Further, interferon therapy has many side effects that hinder patient compliance and results in premature discontinuation of the treatment.

The interferon/ribavirin-based treatment may be physically demanding, and can lead to temporary disability in some cases. A substantial proportion of patients will experience a panoply of side effects ranging from a "flu-like" syndrome (the most common, experienced for a few days after the weekly injection of interferon) to severe adverse events including anemia, cardiovascular events and psychiatric problems such as suicide or suicidal ideation. The latter are exacerbated by the general physiological stress experienced by the patients. Ribavirin also has a number of side effects, including, anemia, high pill burden (e.g. 5-6 pills a day split BID) and teratogenicity restricting use in women of child-bearing age.

The present methods provide effective treatment of HCV infection without the use of interferon and for a shorter period of time, such as a treatment duration of no more than twelve weeks, alternatively no more than eleven weeks, alternatively no more than ten weeks, alternatively no more than nine weeks, alternatively no more than eight weeks, alternatively no more than seven weeks, alternatively no more than six weeks, alternatively no more than five weeks, alternatively no more than four weeks, or alternatively, no more than three weeks.

In some embodiments, the present technology provides methods for treating HCV infection in a subject comprising administering at least two DAAs with ribavirin in the absence of interferon for a duration of no more than twelve weeks, alternatively no more than eight weeks. Put another way, the present methods exclude interferon, or the subject does not receive interferon for the duration of the treatment. The at least two DAAs can be co-administered or can be administered independently (with the same or different dosing frequencies) and can be administered once a day, alternatively twice a day, alternatively three times a day.

In some embodiments, the methods of treatment comprise daily administration of two or more DAAs, wherein a first DAA may be administered once a day, twice a day, or three times a day, and a second DAA may be administered once a day, twice a day, or three times a day. In some embodiments, a third DAA may be administered once a day, twice a day, or three times a day. The DAAs may be co-administered or administered at different times or frequencies. Preferably, in the methods, at least two DAAs and ribavirin are administered in effective amounts to provide a desired measure of effectiveness in the subject. Preferably, the treatment has reduced side effects as compared with interferon-containing treatments.

Various measures may be used to express the effectiveness of the present methods of HCV treatment. One such measure is rapid virological response (RVR), meaning that HCV is undetectable in the subject after 4 weeks of treatment, for example, after 4 weeks of administration of two or more of DAAs and ribavirin. Another measure is early virological response (EVR), meaning that the subject has >2 $\log_{10}$ reduction in viral load after 12 weeks of treatment. Another measure is complete EVR (cEVR), meaning the HCV is undetectable in the serum of the subject after 12 weeks of treatment. Another measure is extended RVR (eRVR), meaning achievement of RVR and cEVR, that is, HCV is undetectable at week 4 and 12. Another measure is the presence or absence of detectable virus at the end of therapy (EOT). Another measure is (SVR), which, as used herein, means that the virus is undetectable at the end of therapy and for at least 8 weeks after the end of therapy (SVR8); preferably, the virus is undetectable at the end of therapy and for at least 12 weeks after the end of therapy (SVR12); more preferably, the virus is undetectable at the end of therapy and for at least 16 weeks after the end of therapy (SVR16); and highly preferably, the virus is undetectable at the end of therapy and for at least 24 weeks after the end of therapy (SVR24). SVR24 is often considered as a functional definition of cure; and a high rate of SVR at less than 24 week post-treatment (e.g., SVR8 or SVR12) can be predictive of a high rate of SVR24. Likewise, a high rate of SVR at less than 12 week post-treatment (e.g., SVR4 or SVR8) can be predictive of a high rate of SVR12. A high rate of EOT (e.g., at week 8 or week 12) can also be indicative of a significant rate of SVR12 or SVR24.

In some embodiments, the amounts of the two or more DAAs and ribavirin, and/or the duration of the treatment regimen of the two or more DAAs and ribavirin, are effective to provide an RVR in a subject, or an EVR in a subject, or a cEVR in a subject, or an eRVR in a subject, or an absence of detectable virus at EOT in a subject. In some embodiments, the present methods comprise treating a population of subjects having HCV infection (e.g. treatment naïve subjects), and the methods comprise administering at least two DAAs and ribavirin to the subjects for a duration of no more than 12 weeks, or for another duration disclosed herein, wherein the at least two DAAs and ribavirin are administered to the subjects in amounts effective to provide an SVR (e.g., SVR after 8 weeks post-treatment, or SVR after 24 weeks post-treatment) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, the present methods comprise treating a population of IFN experienced subjects (e.g., interferon non-responders) having HCV infection, and the methods comprise administering at least two DAAs and ribavirin to the subjects for a duration of no more than 12 weeks, or for another duration disclosed herein, wherein the at least two DAAs and ribavirin are administered to the subjects in amounts effective to provide an SVR (e.g., SVR after 8 weeks post-treatment, or SVR after 24 weeks post-treatment) in at least about 50% of the population, alternatively at least about 55% of the population, alternatively at least about 60% of the population, alternatively at least about 65% of the population. In other embodiments, the amount of DAAs and ribavirin and the duration of the treatment are effective to provide one or more of an SVR (e.g., SVR after 8 weeks post-treatment, or SVR after 24 weeks post-treatment), an RVR, an EVR, a cEVR, an eRVR, or an absence of detectable virus at EOT, in at least about 50% of the population, alternatively at least about 55%, in at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. For example, the present methods comprise administering at least two DAAs and ribavirin in amounts and for durations effective to provide an SVR (e.g., SVR after 8 weeks post-treatment, or SVR after 24 weeks post-treatment) in a subject. In some embodiments, the present technology provides for an SVR (e.g., SVR after 8 weeks post-treatment, or SVR after 24 weeks post-treatment) in at least about 50% of the population, alternatively at least about 55% of the population, in at least about 60% of the population, preferably in at least about 65% of the population, preferably in at least about 70% of the population, preferably at least about 75% of the patients treated by such methods herein described, more preferably in at least 80% of the population, and highly preferably in at least about 90% of the patients being treated. In some embodiments, a treatment of the present technology provides an RVR or undetectable level of HCV RNA in the bloodstream at four (4) weeks of treatment (preferably in addition to a SVR).

A DAA of the present technology includes, but is not limited to, a protease inhibitor, a HCV polymerase inhibitor, an HCV NS5A inhibitor, an HCV NS3B inhibitor, an HCV NS4A inhibitor, an HCV NS5B inhibitor, an HCV entry inhibitor, a cyclophilin inhibitor, a CD81 inhibitor, or an internal ribosome entry site inhibitor. The HCV polymerase inhibitor may be a nucleoside polymerase inhibitor or a non-nucleoside polymerase inhibitor. The HCV polymerase inhibitor may be a nucleotide polymerase inhibitor or a non-nucleotide polymerase inhibitor.

In yet another example of this aspect of the technology, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052 (daclatasvir). In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir).

It was unexpectedly discovered that an interferon-free treatment using a combination of two or more DAAs, together with ribavirin, and for a duration of no more than 12 weeks, could achieve significant SVR. In many cases, such a treatment can achieve an SVR in at least about 75% of patients, and in some cases, such a treatment can achieve an SVR in at least about 85% of patients, and in certain cases, such a treatment can achieve an SVR in at least about 90% of patients. It was also surprising that such a treatment could achieve significant viral suppression even at 4 weeks of the treatment. In some embodiments, the interferon-free treatment using a combination of two or more DAAs, together with ribavirin, and for a duration of no more than 12 weeks, could achieve significant SVR in interferon non-responders, for example, treatment can achieve an SVR in at least about 50% of patients in the interferon non-responder population, preferably at least about 60% of patients in the interferon non-responder population, more preferably at least about 65% of patients in the interferon non-responder population.

Accordingly, in one aspect, the present technology features a method of treating HCV infection, comprising administering to a patient in need thereof an effective amount of a combination of two or more DAAs, together with an effective amount of ribavirin. The treatment lasts 8 weeks and does not include administration of any interferon. The DAAs and ribavirin can be administered at the same or different dosing frequencies. The patient being treated can be a treatment naïve patient, a treatment experienced patient, including, but not limited to, a relapser, an interferon partial responder, an interferon non-responder (e.g., a null responder), or a patient unable to take interferon. The patient may be infected with, for example and without limitation, HCV genotype 1, such as HCV genotype 1a or HCV genotype 1b; or HCV genotype 2 or 3. The treatment according to this aspect of the technology may also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside or nucleotide polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside or nucleotide polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052 (daclatasvir). In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the combination of two or more DAAs includes PSI-7977, Compound 1 (with ritonavir), and Compound 4. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In another aspect, the present technology features a method of treating HCV, comprising administering to a patient in need thereof an effective amount of a combination of two or more DAAs, together with an effective amount of ribavirin. The treatment lasts 7 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052 (daclatasvir). In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the combination of two or more DAAs includes PSI-7977, Compound 1 (with ritonavir), and Compound 4. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 6 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside or nucleotide polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside or nucleotide polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC- 435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the combination of two or more DAAs includes PSI-7977, Compound 1 (with ritonavir), and Compound 4. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 5 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside or nucleotide polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 4 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 3 weeks (or even less, depending on the patient's condition) and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 24 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside or nucleotide polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts from 13 to 23 weeks (e.g., the duration of the treatment is selected from 13, 14, 15, 16, 17, 18, 19, 20, 21, 22 or 23 weeks) and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside or nucleotide polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 12 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052 (daclatasvir). In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 11 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 10 weeks and does not include administration of any interferon. The DAAs and ribavirin can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In yet another aspect, the present technology features a method of treating HCV, comprising administering to a patient in need thereof an effective amount of a combination of two or more DAAs, together with an effective amount of ribavirin. The treatment lasts 9 weeks and does not include administration of any interferon. The DAAs and ribavirin can be administered at the same or different dosing frequency. The patient being treated can be an interferon naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect of the technology can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside polymerase inhibitors, or a combination of at least one nucleoside or nucleotide polymerase inhibitor and at least one non-nucleoside or nucleotide polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 1 (or a salt thereof) and Compound 2 (or a salt thereof). Compound 1 (or a salt thereof) can be co-formulated with ritonavir. In another example, the combination of two or more DAAs is a combination of Compound 1 (or a salt thereof) and Compound 3 (or a salt thereof). Compound 1 (or a salt thereof) can be co-formulated with ritonavir. In still another example, the combination of two or more DAAs is a combination of Compound 1 (or a salt thereof) and Compound 4 (or a salt thereof). Compound 1 (or a salt thereof) can be co-formulated with ritonavir. In a further example, the combination of two or more DAAs is a combination of Compound 1 (or a salt thereof), Compound 2 (or a salt thereof) and Compound 4 (or a salt thereof). Compound 1 (or a salt thereof) can be co-formulated with ritonavir. In yet another example, the combination of two or more DAAs is a combination of Compound 1 (or a salt thereof), Compound 3 (or a salt thereof) and Compound 4 (or a salt thereof). Compound 1 (or a salt thereof) can be co-formulated with ritonavir. In yet another example, the combination of two or more DAAs comprises PSI-7977 and PSI-938. In yet another example, the combination of two or more DAAs comprises PSI-7977 and TMC-435. In yet another example, the combination of two or more DAAs comprises BMS-790052 and BMS-650032. In yet another example, the combination of two or more DAAs comprises GS-5885, GS-9190, and GS-9451. In yet another example, the combination of two or more DAAs comprises BI-201335 and BI-207127. In yet another example, the combination of two or more DAAs comprises telaprevir and VX-222. In another example, the combination of two or more DAAs comprises GS-5885 and GS-9451. In yet another example, the combination of two or more DAAs includes danoprevir (with ritonavir) and R7128. In yet another example, the combination of two or more DAAs includes PSI-7977 and BMS-790052. In yet another example, the combination of two or more DAAs includes PSI-7977 and BMS-650032 (asunaprevir). In still another example, the combination of two or more DAAs includes PSI-7977, BMS-650032 (asunaprevir) and BMS-790052 (daclatasvir). In yet another example, the combination of two or more DAAs includes INX-189 and BMS-790052 (daclatasvir). In yet another example, the combination of two or more DAAs includes INX-189 and BMS-650032 (asunaprevir). In still another example, the combination of two or more DAAs includes INX-189, BMS-650032 (asunaprevir) and BMS-790052 (daclatasvir). In still another example, the combination of two or more DAAs includes mericitabine and danoprevir. In still another example, the combination of two or more DAAs includes INX-189, daclatasvir and BMS-791325. In still another example, the combination of two or more DAAs includes PSI-7977 and GS-5885. In still another example, the method comprises administering to a patient in need thereof an effective amount of PSI-7977 as the sole DAA in lieu of a combination of two or more DAAs, together with an effective amount of ribavirin. In still another example, the method comprises administering 100 or 200 mg Compound 1 together with 100 mg ritonavir once daily, and 25 mg compound 4 once daily. In yet another example, the method comprises administering 150 mg or 250 mg Compound 1 together with 100 mg ritonavir once daily, and 400 mg Compound 2 twice daily. In another example, the method comprises administering 150 mg Compound 1 together with 100 mg ritonavir once daily, and 400 mg Compound 3 once daily. In another example, the method comprises administering 150 mg Compound 1 together with 100 mg ritonavir once daily, and 400 mg Compound 3 twice daily. In another example, the method comprises administering 100 or 150 mg Compound 1 together with 100 mg ritonavir once daily, 25 mg compound 4 once daily, and 400 mg Compound 2 twice daily. In another example, the method comprises administering 100 or 150 mg Compound 1 together with 100 mg ritonavir once daily, 25 mg compound 4 once daily, and 400 mg Compound 3 twice daily. Ribavirin can be administered based on patient weight, and in many cases, 1000 to 1200 mg divided twice daily. Other DAA(s) can also be included in a treatment regimen according to this aspect of the technology.

In another embodiment, the present technology provides interferon-free treatment comprising administering daily two DAAs with ribavirin, where the two DAAs include a HCV polymerase inhibitor, for example PSI-7977 and a NS5A inhibitor, for example BMS-790052 for a duration of no more than twelve weeks (e.g., no more than eleven weeks), preferably no more than eight weeks.

In some embodiments, the present technology provides a method of treating Hepatitis C virus infection in a subject comprising administering daily a HCV protease inhibitor and a HCV polymerase inhibitor to the subject in the absence of interferon for a duration of no more than twelve weeks, preferably no more than eight weeks. In some embodiments, ritonavir (or an equivalent thereof) is co-administered with one or more protease inhibitors to improve the pharmacokinetics of the protease inhibitor(s). The treatment further comprises administering ribavirin to the patient. In some embodiments, the HCV polymerase inhibitor is at least one nucleoside or nucleotide polymerase inhibitor or at least one non-nucleoside polymerase inhibitor. In some embodiments, both a nucleoside or nucleotide polymerase inhibitors and a non-nucleoside polymerase inhibitor may be administered.

The methods of the present technology as described herein may be used to treat a naïve patient or a treatment experienced patient. Treatment experienced patients include interferon non-responders, partial responders (patients whose HCV RNA levels declined but never became undetectable), and relapsers (patients who achieved undetectable levels of HCV RNA during therapy but rebound). Methods of the present technology may also be used to treat patients who are not candidates for interferon treatment. Patients who are not candidates for interferon treatment include, but are not limited to, one or more of the following groups: patients intolerant to interferon, patients who refuse to take interferon treatment, patients with medical conditions which preclude them from taking interferon, and patients who have an increased risk of side effects or infection by taking interferon.

In some embodiments, a cytochrome P-450 inhibitor, e.g. ritonavir, is administered either in the same or separate pharmaceutical composition with the protease inhibitor (e.g. Compound 1 (or a pharmaceutically acceptable salt thereof)) to improve the pharmacokinetics. A cytochrome P450 inhibitor reduces the metabolism of some protease inhibitors, such as Compound 1, thereby improving the pharmacokinetics and bioavailability of the protease inhibitor, for example Compound 1. More preferably, Compound 1 (or a pharmaceutically acceptable salt thereof) is co-formulated with ritonavir in the same dosage form. Other cytochrome P450 inhibitors, such as cobicistat, may also be administered in lieu of ritonavir, to enhance the pharmacokinetics of Compound 1 (or a pharmaceutically acceptable salt thereof).

Inhibitors of cytochrome P450, such as ritonavir, may be co-administered with the DAAs, either sequentially or simultaneously, in the same or different compositions. In some embodiments, the cytochrome P450 inhibitors are administered in order to improve the pharmacokinetics of at least one of the DAAs. Not to be bound by any theory, but a cytochrome P450 inhibitor may also reduce the development of resistant strains of HCV when co-administered with a DAA, thus providing the effectiveness in a shorter treatment. In some embodiments, ritonavir is co-administered with therapeutic agent 1. In some embodiments, ritonavir is co-administered with therapeutic agent 1 in the same compositions.

In some embodiments, the present technology provides a method of treating HCV infection comprising administering at least one protease inhibitor and at least one HCV polymerase inhibitor with ribavirin in a course of treatment of no more than, or less than, eight weeks in the absence of interferon. In some embodiments, the HCV polymerase inhibitor is Compound 1 (or a pharmaceutically acceptable salt thereof).

In some embodiments, the present technology provides a method of treating HCV infection without using interferon, the method comprising administering at least two DAAs and ribavirin to a patient in need of such treatment, wherein the at least two DAAs include at least one protease inhibitor and at least one HCV polymerase inhibitor. In some embodiments, the at least two DAAs includes therapeutic agent 1 with at least one HCV polymerase inhibitor. In some embodiments, the HCV polymerase inhibitor is at least one non-nucleoside polymerase inhibitor. In some embodiments, the non-nucleoside polymerase inhibitor is therapeutic agent 2 or therapeutic agent 3 or a combination thereof.

In some embodiments, the present technology provides a method of treating HCV infection without using interferon, the method comprising administering a HCV protease inhibitor, preferably therapeutic agent 1, with at least one HCV NS5A inhibitor to a patient in need of such treatment. In some embodiments, the NS5A inhibitor is therapeutic agent 4.

In some embodiments of the present technology, a method of treating HCV infection without using interferon, the method comprises administering at least three DAAs and ribavirin to a subject for no more than 8 weeks without administering interferon. The at least three DAAs can be at least one protease inhibitor, at least one HCV polymerase inhibitor, and at least one NS5A inhibitors. In a preferred embodiment, the at least one protease inhibitor is therapeutic agent 1, the at least one polymerase inhibitor is therapeutic agent 2 or therapeutic agent 3, and the at least one NS5A inhibitor is therapeutic agent 4.

Preferred HCV protease inhibitors include, but are not limited to, therapeutic agent 1, telaprevir (Vertex), boceprevir (Merck), BI-201335 (Boehringer Ingelheim), GS-9451 (Gilead), and BMS-650032 (BMS). Other suitable protease inhibitors include, but are not limited to, ACH-1095 (Achillion), ACH-1625 (Achillion), ACH-2684 (Achillion), AVL-181 (Avila), AVL-192 (Avila), BMS-650032 (BMS), danoprevir (RG7227/ITMN-191, Roche), GS-9132 (Gilead), GS-9256 (Gilead), IDX-136 (Idenix), IDX-316 (Idenix), IDX-320 (Idenix), MK-5172 (Merck), narlaprevir (Schering-Plough Corp), PHX-1766 (Phenomix), TMC-435 (Tibotec), vaniprevir (MK-7009, Merck), VBY708 (Virobay), VX-500 (Vertex), VX-813 (Vertex), VX-985 (Vertex), or a combination thereof.

Preferred non-nucleoside HCV polymerase inhibitors for use in the present technology include, but are not limited to, therapeutic agent 2, therapeutic agent 3, GS-9190 (Gilead), BI-207127 (Boehringer Ingelheim), and VX-222 (VCH-222) (Vertex & ViraChem). Preferred nucleotide HCV polymerase inhibitors include, but are not limited to, PSI-7977 (Pharmasset), and PSI-938 (Pharmasset). Other suitable and non-limiting examples of suitable HCV polymerase inhibitors include ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-759 (Vertex), GS-6620 (Gilead), IDX-102 (Idenix), IDX-184 (Idenix), INX-189 (Inhibitex), MK-0608 (Merck), RG7128 (Roche), TMC64912 (Medivir), GSK625433 (GlaxoSmithKline), BCX-4678 (BioCryst), ALS-2200 (Alios BioPharma/Vertex), ALS-2158 (Alios BioPharma/Vertex), or a combination thereof. A polymerase inhibitor may be a nucleoside polymerase inhibitor, such as GS-6620 (Gilead), IDX-102 (Idenix), IDX-184 (Idenix), INX-189 (Inhibitex), MK-0608 (Merck), PSI-7977 (Pharmasset), PSI-938 (Pharmasset), RG7128 (Roche), TMC64912 (Medivir), ALS-2200 (Alios BioPharma/Vertex), ALS-2158 (Alios BioPharma/Vertex), or a combination therefore. A polymerase inhibitor may also be a non-nucleoside polymerase inhibitor, such as PF-00868554 (Pfizer), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-222 (VCH-222) (Vertex & ViraChem), VX-759 (Vertex), or a combination thereof.

Preferred NS5A inhibitors include, but are not limited to, therapeutic agent 4, BMS-790052 (BMS) and GS-5885 (Gilead). Non-limiting examples of suitable NS5A inhibitors include GSK62336805 (Glaxo SmithKline), ACH-2928 (Achillion), AZD2836 (Astra-Zeneca), AZD7295 (Astra-Zeneca), BMS-790052 (BMS), BMS-824393 (BMS), GS-5885 (Gilead), PPI-1301 (Presidio), PPI-461 (Presidio) A-831 (Arrow Therapeutics), A-689 (Arrow Therapeutics) or a combination thereof.

Non-limiting examples of suitable cyclophilin inhibitors include alisporovir (Novartis & Debiopharm), NM-811 (Novartis), SCY-635 (Scynexis), or a combination thereof.

Non-limiting examples of suitable HCV entry inhibitors include ITX-4520 (iTherx), ITX-5061 (iTherx), or a combination thereof.

Specific examples of other DAA agents that are suitable for the present methods include, but are not limited to, AP-H005, A-831 (Arrow Therapeutics) (NS5A inhibitor), A-689 (Arrow Therapeutics) (NS5A inhibitor), INX08189 (Inhibitex) (polymerase inhibitor), ITMN-191 (Intermune/Roche) (NS3/4A Protease inhibitor), VBY-376 (Protease Inhibitor) (Virobay), ACH-1625 (Achillion, Protease inhibitor), IDX136 (Idenix, Protease Inhibitor), IDX316 (Idenix, Protease inhibitor), VX-813 (Vertex), SCH 900518 (Schering-Plough), TMC-435 (Tibotec), ITMN-191 (Intermune, Roche), MK-7009 (Merck), IDX-PI (Novartis), R7128 (Roche), PF-868554 (Pfizer) (non-nucleoside polymerase inhibitor), PF-4878691 (Pfizer), IDX-184 (Idenix), IDX-375 (Idenix, NS5B polymerase inhibitor), PPI-461 (Presidio), BILB-1941 (Boehringer Ingelheim), GS-9190 (Gilead), BMS-790052 (BMS), CTS-1027 (Conatus), GS-9620 (Gilead), PF-4878691 (Pfizer), RO5303253 (Roche), ALS-2200 (Alios BioPharma/Vertex), ALS-2158 (Alios BioPharma/Vertex), GSK62336805 (GlaxoSmithKline), or any combinations thereof.

In some embodiments, the present technology features methods for treating patients with genotype 1, such as 1a or 1b, HCV infection. The methods comprise administering to such a patient a combination of at least 2 DAAs and ribavirin for no more than 12 weeks, preferably no more than 8 weeks, wherein the treatment does not include administration of interferon. Patients with genotype 1, such as 1a or 1b, infection can be treated with a combination of at least 2 DAAs without interferon where the at least two DAAs include therapeutic agent 1 and therapeutic agent 2 with ribavirin. Therapeutic agent 1 and therapeutic agent 2 with ribavirin can be administered in therapeutically effective amounts to provide a SVR (for example, a SVR8, SVR12, SVR16, or SVR24) after a treatment duration of no more than 12 weeks (e.g., the duration being 12 weeks), preferably no more than 8 weeks (e.g., the duration being 8 weeks). The patients may be treatment naïve patients or treatment experienced HCV patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than t 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 2 can be administered with therapeutic agent 1 in any of the dosages of therapeutic agent 1 described above. The total daily dosage of therapeutic agent 2 can be, but is not limited to, for example, about 400 mg, about 500 mg, about 600 mg, about 700 mg, about 800 mg, about 900 mg, about 1000 mg, about 1500 mg, or 1800 mg. Suitably, ribavirin may be administered in connection with therapeutic agent 1 and therapeutic agent 2 at any of the dosages described above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. In some embodiments, ritonavir can be either co-administered or administered separately with therapeutic agent 1. Suitable dosages of ritonavir include, but are not limited to, from about 50 mg to about 400 mg per day, preferably about 100 mg per day.

In some embodiments, the present technology features methods for treating patients with genotype 2 or 3 HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. Patients with genotype 2 or 3 HCV infection can be treated with a combination of at least 2 DAAs without interferon where the at least two DAAs include therapeutic agent 1 and therapeutic agent 2 with ribavirin. Therapeutic agent 1 and therapeutic agent 2 can be administered in therapeutically effective amounts to provide a SVR (for example, a SVR8, SVR12, SVR16, or SVR24) with a treatment duration of no more than 12 weeks, preferably no more than 8 weeks. The patients may be treatment naïve HCV patients or treatment experienced HCV patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 300 mg. Therapeutic agent 2 can be administered in connection with therapeutic agent 1 in any of the dosages described above. The total daily dosage of therapeutic agent 2 can be, but is not limited to, about 400 mg, about 500 mg, about 600 mg, about 700 mg, about 800 mg, about 900 mg, about 1000 mg, about 1500 mg, or 1800 mg. Suitably, ribavirin may be administered in connection with therapeutic agent 1 and therapeutic agent 2 in any combination of suitable dosages described above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. In some embodiments, ritonavir can be either co-administered or administered separately with therapeutic agent 1. Suitable dosages of ritonavir include, from about 50 mg to about 400 mg per day, preferably about 100 mg per day.

In some embodiments, the present technology features methods for treating patients with HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 2 and ribavirin. Suitably, the patient may be a treatment naïve patient, a treatment experienced patient or an interferon non-responder. In some embodiments, the patient is infected with HCV genotype 1, such as genotype 1a. In some embodiments, the patient is infected with HCV genotype 1b. In some embodiments, the patient is infected with HCV genotype 2 or 3, such as 2a or 2b. In some other embodiments, the patient is infected with HCV genotype 3a. The treatment according to this aspect of the technology can also be effective against other HCV genotypes. The treatment duration can be for no more than 12 weeks, preferably no more than 8 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. Therapeutic agent 1 and therapeutic agent 2 can be administered in therapeutically effective amounts to provide a SVR (for example, a SVR8, SVR12, SVR 16, or SVR 24) after treatment duration of no more than 12 weeks, preferably no more than 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 2 can be administered with therapeutic agent 1 in any of the dosages described above. The total daily dosage of therapeutic agent 2 can be, but is not limited to, for example, about 400 mg, about 500 mg, about 600 mg, about 700 mg, about 800 mg, about 900 mg, about 1000 mg. Suitably, ribavirin may be administered in connection with therapeutic agent 1 and therapeutic agent 2 at any combination of the dosages described above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg.

In some embodiments, the present technology features methods for treating patients with HCV infection who are not candidates for interferon treatment. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. Patients who are not candidates for interferon treatment include, but are not limited to, one or more of the following groups: patients intolerant to interferon, patients who refuse to take interferon treatment, patients with medical conditions which preclude them from taking interferon, and patients who have an increased risk of side effects or infection by taking interferon. A non-candidate for interferon treatment can be infected with HCV genotype 1 or 2, for example, genotype 1a or 1b. A non-candidate for interferon treatment can be infected with HCV genotype 2, for example, genotype 2a or 2b. The treatment according to this aspect of the technology can also be effective against other HCV genotypes. In some embodiments, non-candidate for interferon treatment patients can be treated with a combination of at least 2 DAAs without interferon and with ribavirin for a treatment duration of no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The at least two DAAs include at least one HCV protease inhibitor and at least one HCV polymerase inhibitor. Suitably, the at least one HCV protease inhibitor can be therapeutic agent 1 and the at least one HCV polymerase inhibitor can be therapeutic agent 2. Therapeutic agent 1 and therapeutic agent 2 can be administered in therapeutically effective amounts to provide a SVR after a treatment duration of no more than 12 weeks, preferably no more than 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 2 can be administered with therapeutic agent 1 with therapeutic agent 1 administered at any of the dosages described above. The total daily dosage of therapeutic agent 2 can be, but is not limited to, for example, about 400 mg, about 500 mg, about 600 mg, about 700 mg, about 800 mg, about 900 mg, or about 1000 mg. Suitably, ribavirin may be administered in connection with therapeutic agent 1 and therapeutic agent 2 at any of the dosages described above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg.

In another aspect, the present technology features methods for treating patients with HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 2, therapeutic agent 4 and ribavirin. In some embodiments, the patient is infected with HCV genotype 1, such as genotype 1a. The treatment according to this aspect of the technology can also be effective against other HCV genotypes. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks or the duration being 8 weeks. Therapeutic agent 1, therapeutic agent 2, and therapeutic agent 3 can be provided in effective amounts to provide a SVR (for example, a SVR8, SVR12, SVR16, or SVR24) after a treatment duration of no more than 12 weeks, preferably no more than 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 300 mg. Therapeutic agent 2 can be administered with therapeutic agent 1 with therapeutic agent 1 being administered in any of the dosages described above. The total daily dosage of therapeutic agent 2 can be, but is not limited to, for example, about 400 mg, about 500 mg, about 600 mg, about 700 mg, about 800 mg, about 900 mg, or about 1000 mg. Therapeutic agent 4 can be provided in combination with therapeutic agent 1 and therapeutic agent 2 in which therapeutic agent 1 and therapeutic agent 2 are administered in any combination of the dosages for therapeutic agent 1 and therapeutic agent 2 described above. Therapeutic agent 4 can be provided in combination with therapeutic agent 1 and therapeutic agent 2 in a total daily dose of therapeutic agent 4 of an amount from about 5 mg to about 350 mg, preferably about 5 mg to about 300 mg, more preferably about 25 mg to about 200 mg. The total daily dosage of therapeutic agent 4 can be, but are not limited to, for example, about 20 mg, about 25 mg, about 30 mg, about 40 mg, about 50 mg, about 60 mg, about 70 mg, about 75 mg, about 80 mg, about 90 mg, or about 100 mg. In some embodiments, ritonavir can be either co-administered or administered separately with therapeutic agent 1. Suitable dosages of ritonavir include, from about 50 mg to about 400 mg per day, preferably about 100 mg per day. Suitably, ribavirin may be administered in connection with therapeutic agent 1, therapeutic agent 2, and therapeutic agent 4 in which therapeutic agent 1, therapeutic agent 2, and therapeutic agent 4 are administered in any combination of the dosages described above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. Suitably, in some embodiments, the patient may be a treatment naïve patient, a treatment experienced patient, or an interferon nonresponder.

In some embodiments, the present technology features methods for treating patients with genotype 1, such as genotype 1a or 1b, HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 3 and ribavirin. The treatment duration may be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 3 can be administered in connection with therapeutic agent 1 with therapeutic agent 1 being administered at any of the dosages of described above. Therapeutic agent 3 can be provided in combination with therapeutic agent 1. The total daily dosage of therapeutic agent 3 can be, but is not limited to, for example, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 650 mg, about 700 mg, about 750 mg, about 800 mg, about 850 mg, about 900 mg, about 950 mg, or about 1000 mg. Ribavirin can be administered either at the same time or at a separate time than therapeutic agent 1 and therapeutic agent 3; and therapeutic agent 1 and therapeutic agent 3 can be administered in any of the suitable dosages of therapeutic agent 1 or therapeutic agent 3 recited above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. In some embodiments, ritonavir can be either co-administered or administered separately with therapeutic agent 1. Suitable dosages of ritonavir include, from about 50 mg to about 400 mg per day, preferably about 100 mg per day.

In some embodiments, the present technology features methods for treating patients with genotype 2 or 3, such as genotype 2a, 2b or 3a, HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 3 and ribavirin. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. Therapeutic agent 1 and therapeutic agent 3 and ribavirin can be administered in therapeutically effective amounts to provide a SVR (for example, a SVR8, SVR12, SVR16 or SVR24) in a treatment duration of no more than 12 weeks, preferably no more than 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 3 can be administered with therapeutic agent 1 with therapeutic agent 1 being administered at any of the dosages described above. Therapeutic agent 3 can be provided in combination with therapeutic agent 1. The total daily dosage of therapeutic agent 3 can be, but is not limited to, for example, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 650 mg, about 700 mg, about 750 mg, about 800 mg, about 850 mg, about 900 mg, about 950 mg, or about 1000 mg. Ribavirin can be administered either at the same time or at a separate time than therapeutic agent 1 and therapeutic agent 3; and therapeutic agent 1 and therapeutic agent 3 can be administered in any combination of dosage of therapeutic agent 1 or therapeutic agent 3 recited above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. In some embodiments, ritonavir can be either co-administered or administered separately with therapeutic agent 1. Suitable dosages of ritonavir include, from about 50 mg to about 400 mg per day, preferably about 100 mg per day.

In some embodiments, the present technology features methods for treating patients with HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 3 and ribavirin. Suitably, the patient may be a treatment naïve patient, a treatment experienced patient or an interferon non-responder. In some embodiments, the patient is infected with HCV genotype 1, such as genotype 1a. In some embodiments, the patient is infected with HCV genotype 1b. In some other embodiments, the patient is infected with HCV genotype 2 or 3, such as 2a or 2b. In some other embodiments, the patient is infected with HCV genotype 3a. The treatment according to this aspect of the technology can also be effective against other HCV genotypes. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 3 can be administered in connection with therapeutic agent 1 with therapeutic agent 1 being administered at any of the dosages described above. Therapeutic agent 3 can be provided in combination with therapeutic agent 1. The total daily dosage of therapeutic agent 3 can be, but is not limited to, for example, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 650 mg, about 700 mg, about 750 mg, about 800 mg, about 850 mg, about 900 mg, about 950 mg, or about 1000 mg. Ribavirin can be administered either at the same time or at a separate time than therapeutic agent 1 and therapeutic agent 3; and therapeutic agent 1 and therapeutic agent 3 can be administered in any combination of the suitable dosages recited above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. In some embodiments, ritonavir can be either co-administered or administered separately with therapeutic agent 1. Suitable dosages of ritonavir include, from about 50 mg to about 400 mg per day, preferably about 100 mg per day.

In some embodiments, the present technology features methods for treating patients with HCV infection who are not candidates for interferon treatment. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 3 and ribavirin. Patients who are not candidates for interferon treatment include, but are not limited to, one or more of the following groups: patients intolerant to interferon, patients who refuse to take interferon treatment, patients with medical conditions which preclude them from taking interferon, and patients who have an increased risk of side effects or infection by taking interferon. In some embodiments, the patient is infected with HCV genotype 1, such as genotype 1a. In some embodiments, the patient is infected with HCV genotype 1b. In some other embodiments, the patient is infected with HCV genotype 2 or 3, such as 2a or 2b. In some other embodiments, the patient is infected with HCV genotype 3a. The treatment according to this aspect of the technology can also be effective against other HCV genotypes. The treatment duration can be no more than 12 weeks, including but not limited to, no more than 11 weeks, no more than 10 weeks, no more than 9 weeks, but preferably patients who are more than 8 weeks, no more than 7 weeks, no more than 6 weeks, no more than 5 weeks, no more than 4 weeks, or no more than 3 weeks, e.g., the duration being 12 week, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 3 can be administered with therapeutic agent 1 with therapeutic agent 1 being administered at any of the dosages described above. Therapeutic agent 3 can be provided in combination with therapeutic agent 1. The total daily dosage of therapeutic agent 3 can be, but is not limited to, for example, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 650 mg, about 700 mg, about 750 mg, about 800 mg, about 850 mg, about 900 mg, about 950 mg, or about 1000 mg. Ribavirin can be administered either at the same time or at a separate time than therapeutic agent 1 and therapeutic agent 3; and therapeutic agent 1 and therapeutic agent 3 can be administered in any combination of dosages of therapeutic agent 1 and therapeutic agent 3 recited above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg. In some embodiments, ritonavir can be either co-administered or administered separately with therapeutic agent 1. Suitable dosages of ritonavir include, from about 50 mg to about 400 mg per day, preferably about 100 mg per day.

In some embodiments, the present technology features methods for treating patients with HCV genotype 1, such as 1a or 1b, infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 4 and ribavirin. Patients with genotype 1a or 1b infection can be treated with a combination of at least 2 DAAs without interferon in which the at least two DAAs include therapeutic agent 1 and therapeutic agent 4 with ribavirin. Therapeutic agent 1 and therapeutic agent 4 can be administered in therapeutically effective amounts to provide a SVR (for example, a SVR8, SVR12, SVR16, or SVR24) in a treatment duration of no more than 12 weeks, preferably no more than 8 weeks. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 4 can be administered in connection with therapeutic agent 1 where therapeutic agent 1 is administered in any of the dosages described above. Therapeutic agent 4 can be provided in combination with therapeutic agent 1 in a total daily dose of therapeutic agent 4 of from about 25 mg to about 200 mg. The total daily dosage of therapeutic agent 4 can be, but is not limited to, for example, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, or about 350 mg. In some embodiments, ritonavir can be either co-administered or administered separately with therapeutic agent 1. Suitable dosages of ritonavir include, from about 50 mg to about 400 mg per day, preferably about 100 mg per day. In suitable embodiments, therapeutic agent 1 and therapeutic agent 4 are administered once a day. Suitably, ribavirin may be administered in connection with therapeutic agent 1 and therapeutic agent 4 where therapeutic agent 1 and therapeutic agent 4 are administered in any combination of the suitable dosages detailed above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg.

In some embodiments the present technology features methods for treating patients with HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 4 and ribavirin. The patients may be treatment naïve patients or treatment experienced patients. The treatment can be administered for a duration of no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The patient can have HCV genotype 1, such as HCV genotype 1a or 1b. In other embodiments, the patient may have HCV genotype 1b. In some embodiments, it is contemplated to treat other HCV genotypes. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 4 can be administered in connection with therapeutic agent 1 in any of the dosages described above. Therapeutic agent 4 can be provided alone or in combination with therapeutic agent 1. The total daily dosage of therapeutic agent 4 can be, but is not limited to, for example, about 15 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, or about 350 mg. In some embodiments, ritonavir can be either co-administered or administered separately with therapeutic agent 1. Suitable dosages of ritonavir include, from about 50 mg to about 400 mg per day, preferably about 100 mg per day. In suitable embodiments, therapeutic agent 1 and therapeutic agent 4 are administered once a day. In some embodiments, therapeutic agent 1 and therapeutic agent 4 are administered with ribavirin. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg.

In some embodiments, the present technology features methods for treating patients with HCV infection. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 4 and ribavirin. The patients may be treatment naïve patients or treatment experienced patients. The treatment can be administered for a duration of no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The patient can have HCV genotype 2 or 3, such as HCV genotype 2a. In some embodiments, the patient may have HCV genotype 2b. In other embodiments the patient may have HCV genotype 3a. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 4 can be administered in connection with therapeutic agent 1 in which therapeutic agent 1 is administered in any of the dosages described above. Therapeutic agent 4 can be provided in combination with therapeutic agent 1. The total daily dosage of therapeutic agent 4 can be, but is not limited to, for example, about 15 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, or about 350 mg. In some embodiments, ritonavir can be either co-administered or administered separately with therapeutic agent 1. Suitable dosages of ritonavir include, from about 50 mg to about 400 mg per day, preferably about 100 mg per day. In suitable embodiments, therapeutic agent 1 and therapeutic agent 4 are administered once a day. In some embodiments, therapeutic agent 1 and therapeutic agent 4 are administered with ribavirin. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg.

In some embodiments, the present technology features methods for treating patients with HCV infection who are not candidates for interferon treatment. The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. The combination comprises therapeutic agent 1, therapeutic agent 4 and ribavirin. Patients who are not candidates for interferon treatment include, but are not limited to one or more of the following groups: patients intolerant to interferon, patients who refuse to take interferon treatment, patients with medical conditions which preclude them from taking interferon, and patients who have an increased risk of side effects or infection by taking interferon. In some embodiments, the patient is infected with HCV genotype 1, such as genotype 1a. In some embodiments, the patient is infected with HCV genotype 1b. In some other embodiments, the patient is infected with HCV genotype 2 or 3, such as 2a or 2b. In some other embodiments, the patient is infected with HCV genotype 3a. The treatment according to this aspect of the technology can also be effective against other HCV genotypes. Therapeutic agent 1 and therapeutic agent 4 can be administered in therapeutically effective amounts to provide a SVR (for example, a SVR8, SVR12, SVR16 or SVR24) after treatment of no more than 12 weeks, preferably no more than 8 weeks. The interferon non-responder patients include partial interferon responders and interferon rebound patients. See GUIDANCE FOR INDUSTRY— CHRONIC HEPATITIS C VIRUS INFECTION: DEVELOPING DIRECT-ACTING ANTIVIRAL AGENTS FOR TREATMENT (FDA, September 2010, draft guidance) for the definitions of naive, partial responder, responder relapser (i.e., rebound), and null responder patients. The interferon non-responder patients also include null responder patients. The treatment can be administered for a duration of no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 4 can be administered with therapeutic agent 1 where therapeutic agent 1 is administered in any of the dosages described above. Therapeutic agent 4 can be provided in combination with therapeutic agent 1. The total daily dosage of therapeutic agent 4 can be, but is not limited to, for example, about 15 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, or about 350 mg. In some embodiments, ritonavir can be either co-administered or administered separately with therapeutic agent 1. Suitable dosages of ritonavir include, from about 50 mg to about 400 mg per day, preferably about 100 mg per day. In suitable embodiments, therapeutic agent 1 and therapeutic agent 4 are administered once a day. Suitably, ribavirin may be administered in connection with therapeutic agent 1 and therapeutic agent 4 where therapeutic agent 1 and therapeutic agent 4 are administered in any combination of suitable dosages as described above. Suitable total daily dosages of ribavirin can be based on the weight of the patient and include, but are not limited to, from from about 800 mg to about 1200 mg, including, for example, about 1000 mg per day for a patient <75 kg or about 1200 mg per day for a patient ≧75 kg.

In some embodiments, the present technology features methods for treating patients with HCV infection who are interferon non-responders (e.g., null responders). The methods comprise administering to such a patient a combination of at least 2 DAAs and ribavirin for no more than 12 weeks (e.g., the duration being 12 weeks), preferably no more than 8 weeks (e.g., the duration being 8 weeks), wherein the treatment does not include administration of interferon. Interferon nonresponder patients can be treated with a combination of at least 2 DAAs without interferon with ribavirin wherein the two DAAs include therapeutic agent 1 and therapeutic agent 4 with ribavirin. Therapeutic agent 1 and therapeutic agent 4 can be administered in therapeutically effective amounts to provide a SVR (for example, a SVR8, SVR12, SVR16 or SVR24) after treatment duration of no more than 12 weeks, preferably no more than 8 weeks. The interferon non-responder patients include partial interferon responders and interferon rebound patients. The interferon nonresponder patient may have HCV genotype 1, such as 1a. The interferon nonresponder patient may have HCV genotype 1b. The interferon nonresponder patient can have HCV genotype 2 or 3, such as HCV genotype 2a. In some embodiments, the patient may have HCV genotype 2b. In other embodiments the patient may have HCV genotype 3a. In some embodiments, it is contemplated to treat other HCV genotypes. The treatment can be administered for a duration of no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks. The total daily dosage of therapeutic agent 1 can be, but is not limited to, for example, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. Therapeutic agent 4 can be administered with therapeutic agent 1 wherein therapeutic agent 1 is administered in any of the dosages described above. Therapeutic agent 4 can be provided in combination with therapeutic agent 1. The total daily dosage of therapeutic agent 4 can be, but is not limited to, for example, about 15 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, or about 350 mg. In some embodiments, ritonavir can be either co-administered or administered separately with therapeutic agent 1. Suitable dosages of ritonavir include, from about 50 mg to about 400 mg per day, preferably about 100 mg per day. In suitable embodiments, therapeutic agent 1 and therapeutic agent 4 are administered once a day. Suitably, ribavirin may be administered in connection with therapeutic agent 1 and therapeutic agent 4 wherein therapeutic agent 1 and therapeutic agent 4 are administered in any combination of suitable dosages as described above. Suitable total daily dosages of ribavirin can be based on the weight of the patient and include, but are not limited to, from about 800 mg to about 1200 mg, including, for example, about 1000 mg per day for a patient <75 kg or about 1200 mg per day for a patient ≧75 kg.

Accordingly, in some embodiments, the present technology features a method of treating HCV infection, comprising administering to a patient in need thereof an effective amount of a combination of two or more DAAs, together with an effective amount of ribavirin. The treatment lasts no more than 12 weeks, alternatively no more than 11 weeks, alternatively no more than 10 weeks, alternatively no more than 9 weeks, preferably no more than 8 weeks, alternatively no more than 7 weeks, alternatively no more than 6 weeks, alternatively no more than 5 weeks, alternatively no more than 4 weeks, alternatively no more than 3 weeks and does not include administration of any interferon. The DAAs and ribavirin can be administered at the same or different dosing frequencies. The patient being treated can be an HCV-treatment naïve patient or HCV-treatment experienced patient, including, interferon non-responders, interferon partial responders (patients whose HCV RNA levels declined but never became undetectable when treated with interferon), or relapsers (patients who achieved undetectable levels of HCV RNA during therapy but rebound) or a patient unable to take interferon. The patient can be infected with, for example and without limitation, HCV genotypes 1 or 2. In some embodiments are preferably genotypes 1a or 1b. In other embodiments, the HCV genotype is 2 or 3. Each DAA can be selected from HCV protease inhibitors, HCV polymerase inhibitors, or HCV NS5A inhibitors.

For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor).

For another instance, the combination of two or more DAAs can be a combination of at least one HCV protease inhibitor and at least one HCV NS5A inhibitor. In an example, the combination of two or more DAAs comprises GS-5885 (an NS5A inhibitor), and GS-9451 (a protease inhibitor or an NS3 protease inhibitor). In some examples, GS-5885 is provided in a daily dose from about 3 mg to about 200 mg, alternatively from about 3 mg to about 100 mg, alternatively from about 30 mg to about 90 mg, including, but not limited to, for example, about 3 mg, about 5 mg, about 10 mg, about 15 mg, about 20 mg, about 25 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. GS-9451 can be administered in combination with any of the daily dosages of GS-5885 described above. GS-9451 can be administered in a total daily dose from about 100 mg to about 500 mg, alternatively from about 200 mg to about 400 mg, including, but not limited to, for example, about 100 mg, about 150 mg, about 200 mg, about 250 mg, about 300 mg, about 400 mg, or about 500 mg. Suitably examples include total daily dosages of about 30 mg GS-5885 and about 200 mg GS-9451; alternatively about 60 mg GS-5885 and about 200 mg GS-9451; alternatively about 90 mg GS-5885 and about 200 mg GS-9451.

In another instance, the present technology provides the at least two DAAs comprise at least two HCV polymerase inhibitors. In some embodiments, the at least two HCV polymerase inhibitors comprise at least one nucleoside or nucleotide analog polymerase inhibitor. In some embodiments, the at least two HCV polymerase inhibitors comprise at least two nucleoside or nucleotide analog polymerase inhibitors. Suitable nucleotide analog polymerase inhibitors include PSI-7977 (Pharmasset) and PSI-938 (Pharmasset). Suitable daily dosages of the at least one nucleoside or nucleotide analog polymerase inhibitor include from about 100 mg to about 500 mg, alternatively from about 200 mg to about 400 mg, including, but not limited to, for example, about 100 mg, about 150 mg, about 200 mg, about 250 mg, about 300 mg, about 350 mg, about 400 mg, about 450 mg, or about 500 mg. For example, a suitable combination includes a total daily dose of PSI-7977 of about 400 mg and a total daily of PSI-938 of about 300 mg, alternatively a total daily dose of about 200 mg PSI-7977 and a total daily dose of about 300 mg PSI-938. Suitably, ribavirin can be administered with the at least two DAAs, preferably in an amount based on weight of the subject, in a total daily dose of from about 400 mg to about 1400 mg, suitably about 1000 mg or about 1200 mg per day. For example, a suitable ribavirin daily treatment is weight based, for example, 1000 mg/day<75 kg and 1200 mg/day≧75 kg, divided twice daily (BID). In yet another instance, the combination of two or more DAAs comprises at least one HCV protease inhibitor and at least one HCV polymerase inhibitor. In some embodiments, the at least one protease inhibitor is TMC-435 (Medivir) and the at least one polymerase inhibitor is a nucleotide/nucleoside analog polymerase inhibitor, for example PSI-7977. Suitably, the at least one protease inhibitor, e.g. TMC-435, is provided in a total daily dosage from about 25 mg to about 250 mg, alternatively from about 25 mg to about 200 mg, alternatively from about 50 mg to about 200 mg, alternatively from about 75 mg to about 150 mg, for example, about 25 mg, about 50 mg, about 75 mg, about 100 mg, about 125 mg, about 150 mg, about 175 mg, or about 200 mg; and the at least one polymerase inhibitor (e.g. PSI-7977) is provided in a total daily dose from about 100 mg to about 500 mg, alternatively from about 200 mg to about 400 mg, including, but not limited to, for example, about 100 mg, about 150 mg, about 200 mg, about 250 mg, about 300 mg, about 350 mg, about 400 mg, about 450 mg, or about 500 mg. For example, a combination can be a total daily dosage of about 75 mg TMC-435 and about 400 mg PSI-7977, alternatively about 100 mg TMC-435 and about 400 mg PSI-7977, alternatively about 150 mg TMC-435 and about 400 mg PSI-7977, alternatively about 100 mg TMC-435 and about 400 mg PSI-7977, alternatively about 75 mg TMC-435 and about 200 mg PSI-7977, alternatively about 150 mg TMC-435 and about 200 mg PSI-7977, alternatively about 100 mg TMC-435 and about 200 mg PSI-7977, alternatively about 75 mg TMC-435 and about 100 mg PSI-7977, alternatively about 100 mg TMC-435 and about 100 mg PSI-7977, alternatively about 150 mg TMC-435 and about 100 mg PSI-7977, and can include other suitable combinations. Suitably, in some embodiments, ritonavir or a suitable equivalent can be added to the at least two DAAs comprising at least one protease inhibitor, suitably in an amount from about 100 mg to about 400 mg per day, preferably about 100 mg per day. Suitable ribavirin can be administered with the at least two DAAs, preferably in an amount based on weight of the subject, suitably about 1000 mg or about 1200 mg per day. For example, a suitable ribavirin daily treatment is weight based, for example, 1000 mg/day<75 kg and 1200 mg/day≧75 kg, divided twice daily (BID). In alternative embodiments, the at least one protease is BI-201335 (NS3/4A protease inhibitor) and the at least one HCV polymerase inhibitor is a non-nucleoside polymerase inhibitor, e.g. BI-207127. In some examples, the BI-201335 is provided in a total daily dose from about 100 mg to about 400 mg, alternatively from about 120 mg to about 240 mg, including about 100 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 275 mg, about 300 mg, about 320 mg, about 330 mg, about 350 mg, about 360 mg, about 370 mg, about 380 mg, or about 400 mg; and BI-207127 can be administered in a total daily dose from about 300 mg to about 3600 mg, preferably from about 1200 mg to about 2100 mg, including, but not limited to, for example, about 300 mg, about 400 mg, about 500 mg, about 600 mg, about 700 mg, about 750 mg, about 800 mg, about 900 mg, about 1000 mg, about 1100, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2400 mg, about 2500 mg, about 2600 mg, about 2700 mg, about 2800 mg, about 3000 mg, about 3200 mg, about 3400 mg, or about 3600 mg. Suitable examples, include, but are not limited to, a combination of a total daily dose of about 120 mg BI-201335 and about 1200 mg BI-207127, alternatively about 120 mg BI-201335 and about 1500 mg BI-207127, alternatively about 120 mg BI-201335 and about 1800 mg BI-207127, alternatively about 120 mg BI-201335 and about 2100 mg BI-207127, alternatively about 240 mg BI-201335 and about 1200 mg BI-207127, alternatively about 240 mg BI-201335 and about 1500 mg BI-207127, alternatively about 240 mg BI-201335 and about 1800 mg BI-207127, alternatively about 240 mg BI-201335 and about 2100 mg BI-207127. Suitably, in some embodiments, ritonavir or a suitable equivalent can be added to the at least two DAAs comprising at least one protease inhibitor, suitably in an amount of about 100 mg per day. Suitably, in some embodiments, ritonavir or a suitable equivalent can be added to the at least two DAAs comprising at least one protease inhibitor, suitable in an amount from about 100 mg to about 400 mg per day, preferably about 100 mg per day. Suitable ribavirin can be administered with the at least two DAAs, preferably in an amount based on weight of the subject, suitably from about 400 mg to about 1400 mg per day, for example, about 1000 mg or about 1200 mg per day. For example, a suitable ribavirin daily treatment is weight based, for example, from 400 mg to about 1400 mg, preferably about 1000 mg/day<75 kg and 1200 mg/day≧75 kg, divided twice daily (BID). In yet another example, the combination of two or more DAAs comprises telaprevir (VX-950, protease inhibitor) and VX-222 (non-nucleoside polymerase inhibitor). In some examples, the telaprevir is provided in total daily doses from about 1000 mg to about 2500 mg, alternatively from about 2000 mg to about 2500 mg, including, but not limited to, for example, about 1000 mg, about 1200 mg, about 1300 mg, about 1500 mg, about 1700 mg, about 1800 mg, about 1900 mg, about 2000 mg, about 2100 mg, about 2200 mg, about 2250 mg, about 2300 mg, about 2400 mg, about 2500 mg. VX-222 can be administered with telaprevir in any combination with the dosage amounts of telaprevir provided above. VX-222 can be provided in a total daily dosage from about 100 mg to about 1000 mg, alternatively from about 200 mg to about 800 mg, including, but not limited to, for example, about 100 mg, about 200 mg, about 300 mg, about 400 mg, about 500 mg, about 600 mg, about 700 mg, about 800 mg, about 900 mg, or about 1000 mg. In some examples, telaprevir can be a total daily dose of about 2250 mg and VX-222 can be a total daily dose of about 100 mg, alternatively telaprevir can be a total daily dose of about 2250 mg and VX-222 can be a total daily dose of about 200 mg, alternatively telaprevir can be a total daily dose of about 2250 mg and VX-222 can be a total daily dose of about 400 mg, alternatively telaprevir can be a total daily dose of about 2250 mg and VX-222 can be a total daily dose of about 600 mg, alternatively telaprevir can be a total daily dose of about 2250 mg and VX-222 can be a total daily dose of about 800 mg, alternatively telaprevir can be a total daily dose of about 1500 mg and VX-222 can be a total daily dose of about 200 mg, alternatively telaprevir can be a total daily dose of about 1500 mg and VX-222 can be a total daily dose of about 400 mg, alternatively telaprevir can be a total daily dose of about 1500 mg and VX-222 can be a total daily dose of about 800 mg. Suitably, telaprevir can be administered three times a day (TID), for example 3 times a day with 750 mg per dose. Other suitable daily dosage of telaprevir is 1125 mg twice a day (BID). Suitably, in some embodiments, ritonavir or a suitable equivalent can be added to the at least two DAAs comprising at least one protease inhibitor, suitably in an amount of about 100 mg to about 400 mg per day, preferably about 100 mg per day. Suitable ribavirin can be administered with the at least two DAAs, preferably in an amount based on weight of the subject, from about 400 mg to about 1400 mg, suitably about 1000 mg or about 1200 mg per day. For example, a suitable ribavirin daily treatment is weight based, for example, 1000 mg/day<75 kg and 1200 mg/day≧75 kg, divided twice daily (BID).

In yet another example, the combination of two or more DAAs includes danoprevir (protease inhibitor) and R7128 (nucleoside polymerase inhibitor). In some embodiments, danoprevir can be administered in a total daily dosage from about 100 mg to about 2000 mg, alternatively from about 200 mg to about 1800 mg, alternatively from about 400 mg to about 1800 mg, including, but not limited to, for example, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, and other amounts therebetween. R7128 can be administered in a total daily dose from about 100 mg to about 2000 mg, alternatively from about 200 mg to about 2000 mg, alternatively from about 1000 mg to about 2000 mg, including, but not limited to, for example, about 150 mg, about 200 mg, about 400 mg, about 500 mg, about 600 mg, about 700 mg, about 800 mg, about 900 mg, about 1000 mg, about 1200 mg, about 1300 mg, about 1400 mg, about 1500 mg, about 1600 mg, about 1700 mg, about 1800 mg, about 1900 mg, or about 2000 mg. In some examples, the total daily dose of the danoprevir is about 200 mg and the total daily dose of R7128 is about 200 mg, alternatively the total daily doses of the danoprevir is about 400 mg and the total daily dose of R7128 is about 200 mg, alternatively, the total daily dose of the danoprevir is about 1000 mg and the total daily dose of R7128 at about 200 mg, alternatively the total daily dose of the danoprevir is about 1800 mg and the total daily dose of R7128 is about 200 mg, alternatively the total daily dose of the danoprevir is about 2000 mg and the total daily dose of R7128 is about 200 mg, alternatively the total daily dose of the danoprevir is about 400 mg and the total daily dose of R7128 is about 400 mg, alternatively, the total daily dose of the danoprevir is about 1000 mg and the total daily dose of R7128 is about 400 mg, alternatively the total daily dose of the danoprevir is about 2000 mg and the total daily dose of R7128 is about 400 mg, alternatively the total daily dose of the danoprevir is about 1800 mg and the total daily dose of R7128 is about 400 mg, alternatively the total daily dose of the danoprevir is about 400 mg and the total daily dose of R7128 is about 1000 mg, alternatively, the total daily dose of the danoprevir is about 1000 mg and the total daily dose of R7128 is about 1000 mg, alternatively the total daily dose of the danoprevir is about 2000 mg and the total daily dose of R7128 is about 1000 mg, alternatively the total daily dose of the danoprevir is about 1800 mg and the total daily dose of R7128 is about 1000 mg, alternatively the total daily dose of the danoprevir is about 400 mg and the total daily dose of R7128 is about 2000 mg, alternatively, the total daily dose of the danoprevir is about 1000 mg and the total daily dose of R7128 is about 2000 mg, alternatively the total daily dose of the danoprevir is about 2000 mg and the total daily dose of R7128 is about 2000 mg, alternatively the total daily dose of the danoprevir is about 1800 mg and the total daily dose of R7128 is about 2000 mg. In suitable embodiments, danoprevir and R7128 can be administered with ritonavir, suitably in an amount of about 100 mg to about 400 mg per day, preferably about 100 mg per day. Suitable ribavirin can be administered with the at least two DAAs, preferably in an amount based on weight of the subject, from about 400 mg to about 1400 mg, suitably about 1000 mg or about 1200 mg per day. For example, a suitable ribavirin daily treatment is weight based, for example, 1000 mg/day<75 kg and 1200 mg/day≧75 kg, divided twice daily (BID).

In some other instances of the present technology, the combinations of two or more DAAs may be at least one protease inhibitor and at least one NS5A inhibitor. In some examples, the at least one protease inhibitor is an NS3 protease inhibitor. In some embodiments, the at least one protease inhibitor and at least one NS5A inhibitor comprises BMS-650032 (BMS) and BMS-790052 (BMS) respectively. In suitable embodiments, BMS-650032 can be administered in a total daily dose from about 300 mg to about 1500 mg, alternatively from about 500 mg to about 1500 mg, including, but not limited to, for example, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, and about 1500 mg, and BMS-790052 (BMS) can have a total daily dose from about 10 mg to about 200 mg, alternatively from about 50 mg to about 100 mg, including, but not limited to, for example, about 10 mg, about 20 mg, about 30 mg, about 40 mg, about 50 mg, about 60 mg, about 75 mg, about 100 mg, about 125 mg, about 150 mg, or about 200 mg. In suitable examples, BMS-650032 (BMS) total daily dose is about 1200 mg and BMS-790052 (BMS) total daily dose is about 60 mg, alternatively BMS-650032 (BMS) total daily dose is about 300 mg and BMS-790052 (BMS) total daily dose is about 60 mg. Suitable ribavirin can be administered with the at least two DAAs, preferably in an amount based on weight of the subject, from about 400 mg to about 1400 mg, suitably about 1000 mg or about 1200 mg per day. For example, a suitable ribavirin daily treatment is weight based, for example, 1000 mg/day<75 kg and 1200 mg/day≧75 kg, divided twice daily (BID).

In some other instances of the present technology, the combinations of two or more DAAs may be at least one nucleoside or nucleotide polymerase inhibitor, at least one protease inhibitor, and at least one NS5A inhibitor. In some examples, the at least one protease inhibitor is an NS3 protease inhibitor. In some embodiments, the at least one nucleoside or nucleotide polymerase inhibitor is INX-189, the at least one protease inhibitor is BMS-650032 (asunaprevir), and the at least one NS5A inhibitor comprises is BMS-790052 (daclatasivr). Such embodiments are especially contemplated for treating a patient infected with HCV genotype 1, such as genotype 1a or 1b (particularly genotype 1a), as well as patients infected with other HCV genotypes, such as genotypes 2 or 3. In suitable embodiments, INX-189 can be administered in a total daily dose from about 5 mg to about 400 mg, alternatively from about 25 mg to about 200 mg, including but not limited to, for example, about 5 mg, about 10 mg, about 15 mg, about 20 mg, about 25 mg, about 30 mg, about 40 mg, about 50 mg, about 60 mg, about 70 mg, about 80 mg, about 90 mg, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, or about 300 mg. In suitable embodiments, BMS-650032 can be administered in a total daily dose from about 300 mg to about 1500 mg, alternatively from about 500 mg to about 1500 mg, including, but not limited to, for example, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, and about 1500 mg, and BMS-790052 (BMS) can have a total daily dose from about 10 mg to about 200 mg, alternatively from about 50 mg to about 100 mg, including, but not limited to, for example, about 10 mg, about 20 mg, about 30 mg, about 40 mg, about 50 mg, about 60 mg, about 75 mg, about 100 mg, about 125 mg, about 150 mg, or about 200 mg. In suitable examples, BMS-650032 (BMS) total daily dose is about 1200 mg and BMS-790052 (BMS) total daily dose is about 60 mg, alternatively BMS-650032 (BMS) total daily dose is about 300 mg and BMS-790052 (BMS) total daily dose is about 60 mg. Suitable ribavirin can be administered with the at least two DAAs, preferably in an amount based on weight of the subject, from about 400 mg to about 1400 mg, suitably about 1000 mg or about 1200 mg per day. For example, a suitable ribavirin daily treatment is weight based, for example, 1000 mg/day<75 kg and 1200 mg/day≧75 kg, divided twice daily (BID).

For still another instance, the combination of two or more DAAs can be a combination of at least one HCV protease inhibitor, at least one HCV polymerase inhibitor, and at least one HCV NS5A inhibitor. In an example, the combination of two or more DAAs comprises GS-5885 (an NS5A inhibitor), GS-9190 (tegobuvir, a non-nucleoside polymerase inhibitor), and GS-9451 (a protease inhibitor or a NS3 protease inhibitor). In some examples, GS-5885 is provided in a daily dose from about 3 mg to about 200 mg, alternatively from about 3 mg to about 100 mg, alternatively from about 30 mg to about 90 mg, including, but not limited to, for example, about 3 mg, about 5 mg, about 10 mg, about 15 mg, about 20 mg, about 25 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg, and GS-9190 is provided in a daily dose from about 10 mg to about 100 mg, alternatively from about 30 mg to about 90 mg, including, but not limited to, for example, about 10 mg, about 20 mg, about 30 mg, about 40 mg, about 50 mg, about 60 mg, about 70 mg, about 80 mg, about 90 mg, or about 100 mg; and GS-9451 can be administered in a daily dose from about 100 mg to about 500 mg, alternatively from about 200 mg to about 400 mg, including, but not limited to, about 100 mg, about 150 mg, about 200 mg, about 250 mg, about 300 mg, about 400 mg, or about 500 mg. Suitably examples include about daily amounts of about 30 mg GS-5885, about 60 mg GS-9190 and about 200 mg GS-9451; alternatively about 60 mg GS-5885, about 60 mg GS-9190, and about 200 mg GS-9451; alternatively about 90 mg GS-5885, about 60 mg GS-9190, and about 200 mg GS-9451. In some embodiments the GS-9190, GS-9451, and GS-5885 is administered with ritonavir or a suitable equivalent, suitably in an amount of about 100 mg to about 400 mg per day, preferably about 100 mg per day. Suitable ribavirin can be administered with the at least two DAAs, preferably in an amount based on weight of the subject, from 400 mg to about 1400 mg, suitably about 1000 mg or about 1200 mg per day. For example, a suitable ribavirin daily treatment is weight based, for example, 1000 mg/day<75 kg and 1200 mg/day≧75 kg, divided twice daily (BID). For still another instance, the combination of two or more DAAs can be a combination of at least one HCV protease inhibitor, at least one HCV polymerase inhibitor, and at least one HCV NS5A inhibitor.

In another embodiment, the present technology provides interferon-free treatment comprising administering daily two DAAs with ribavirin, where the two DAAs include a HCV polymerase inhibitor, for example PSI-7977 and a NS5A inhibitor, for example BMS-790052 for a duration of no more than eleven weeks, preferably no more than eight weeks. PSI-7977 and BMS-790052 are administered in an effective amount to provide an SVR (for example, an SVR8, SVR12, SVR16, or SVR24) with a treatment duration of no more than eleven weeks, no more than ten weeks, no more than nine weeks, no more than eight weeks, no more than seven weeks, no more than six weeks, no more than five weeks, no more than four weeks or no more than three weeks. The patients can be treatment naïve patients or treatment experienced patients. In some embodiments, the patients can have HCV genotype 1, such as 1a or 1b. In some embodiments, the patients can have genotype 2 or 3, such as 2a, 2b or 3a. PSI-7977 can be provided in a total daily dose of from about 100 mg to about 500 mg, alternatively from about 200 mg to about 400 mg, including, but not limited to, for example, about 100 mg, about 150 mg, about 200 mg, about 250 mg, about 300 mg, about 350 mg, about 400 mg, about 450 mg, about 500 mg. BMS-790052 can be administered in combination with PSI-7977 at any daily dose of PSI-7977 provided above. BMS-790052 (BMS) can have a total daily dose of from about 10 mg to about 200 mg, alternatively from about 50 mg to about 100 mg, including, but not limited to, about 10 mg, about 20 mg, about 30 mg, about 40 mg, about 50 mg, about 60 mg, about 75 mg, about 100 mg, about 125 mg, about 150 mg, or about 200 mg. In one suitable example, PSI-7977 is administered in a total daily dose of 400 mg and BMS-790052 is administered in a total daily dose of 60 mg.

The chemical structures of some of these HCV inhibitors as reported by numerous sources are provided below:

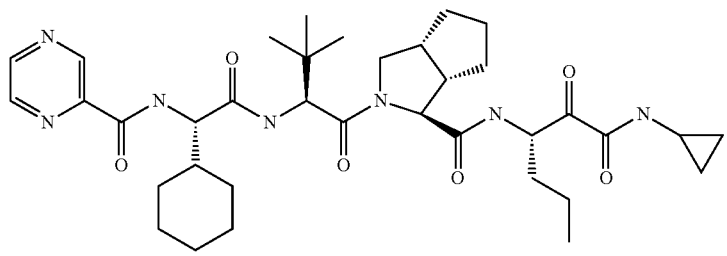
Telaprevir
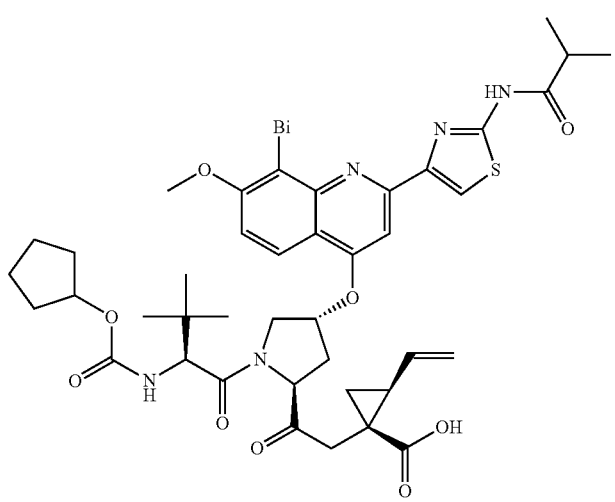
BI-201335
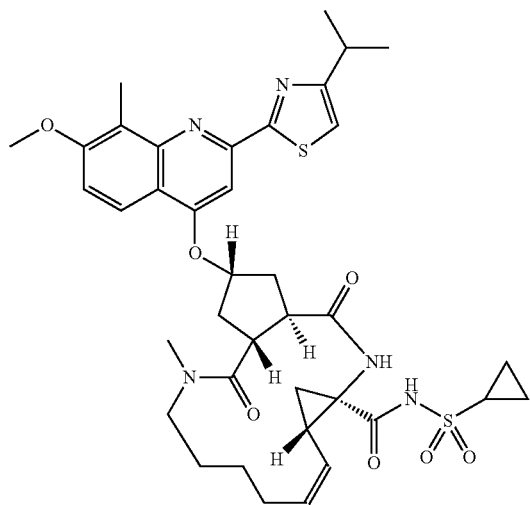
TMC-435 (TMC-435350)
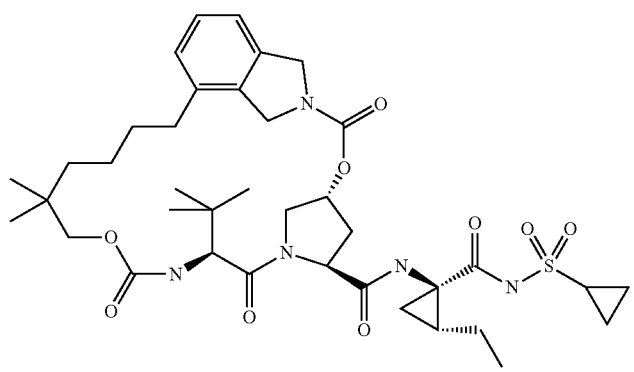
Vaniprevir, MK-7009
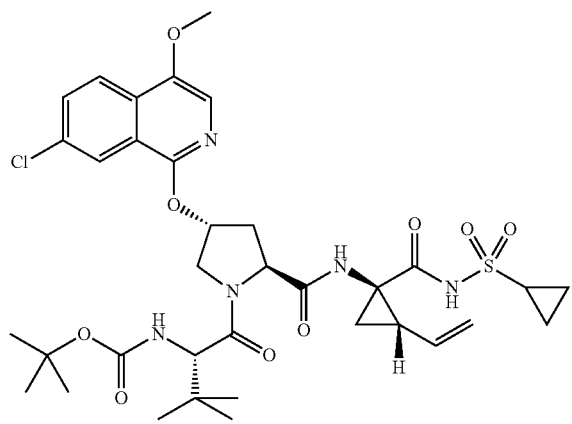
BMS-650032 (Asunaprevir)

-continued
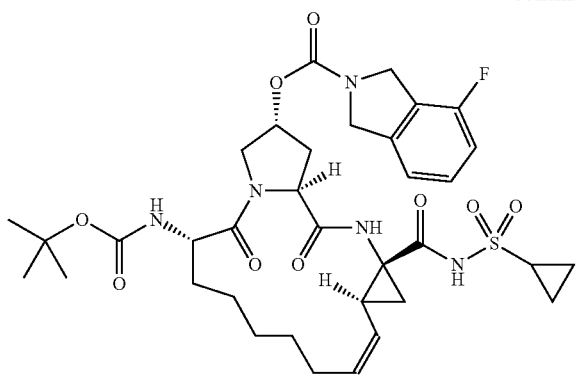
danoprevir
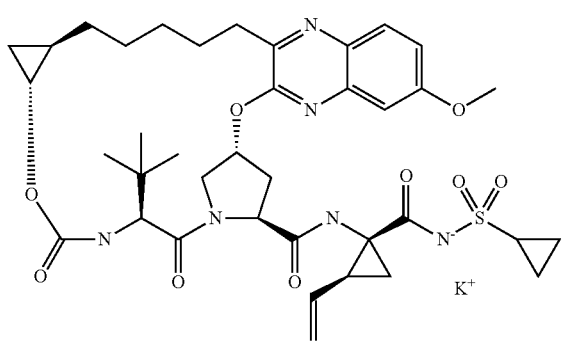
MK-5172
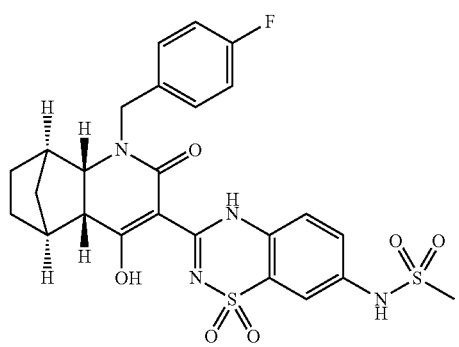
ANA-598 (Setrobuvir)
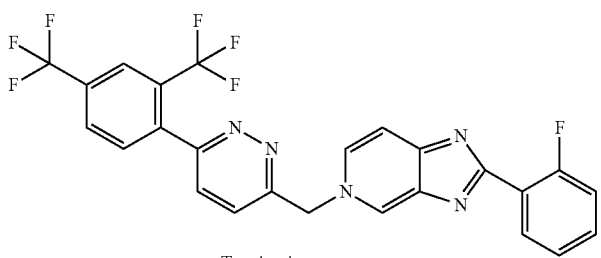
Tegobuvir
GS-333126 (GS-9190 or tegobuvir)
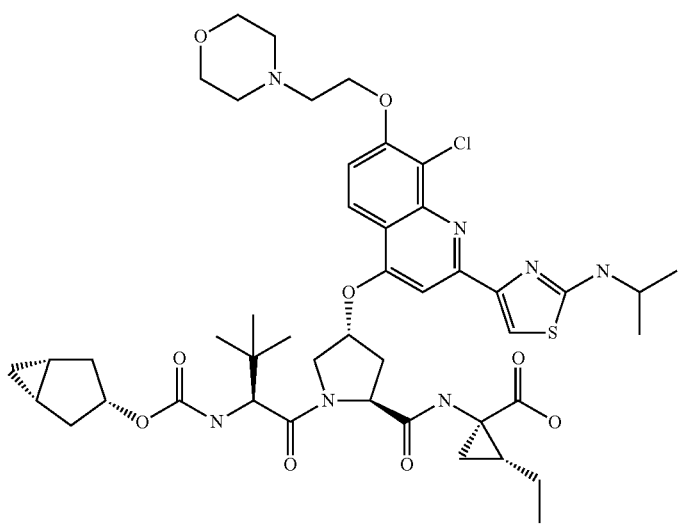
GS-9451
GS-9451

-continued
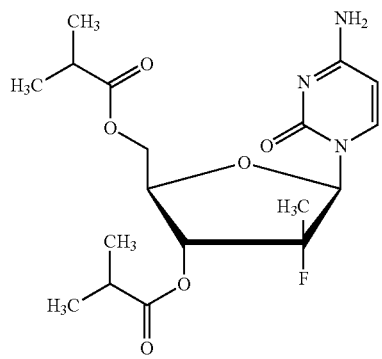
Mericitabine (R-4048 or RG7128 or R7128)
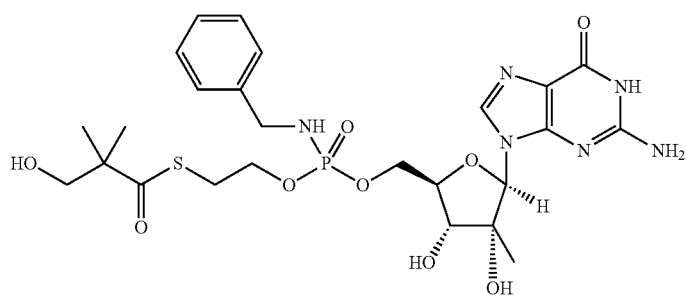
IDX-184
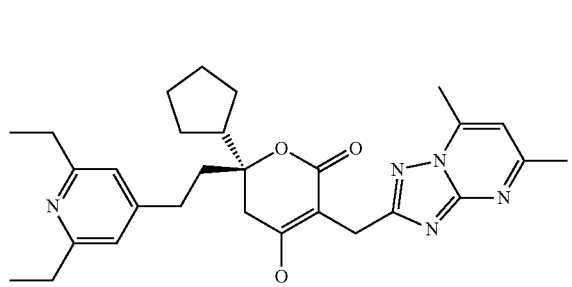
filibuvir (PF-00868554)
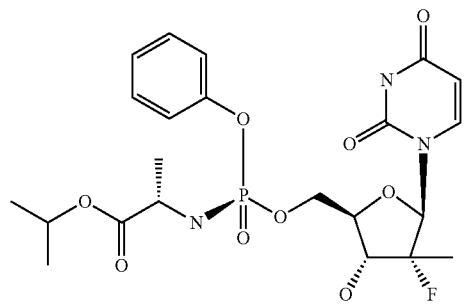
PSI-7977
PSI-7977 (GS-7977)
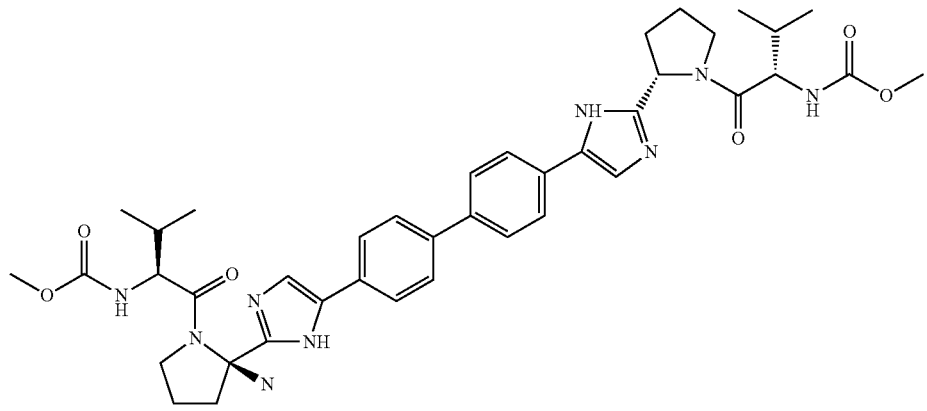
BMS-790052 (daclatasvir)

-continued
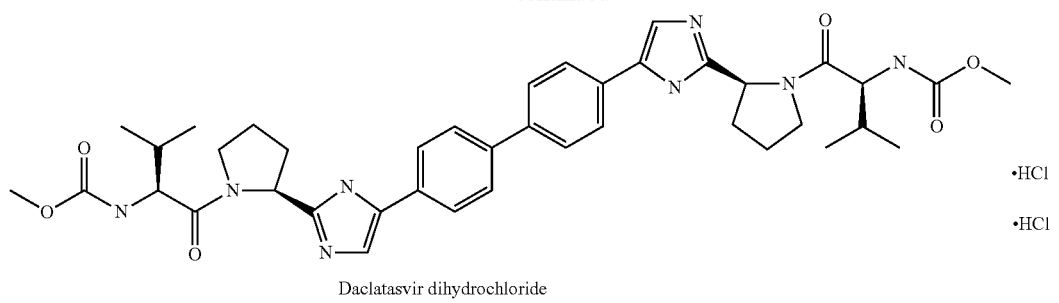
Daclatasvir dihydrochloride
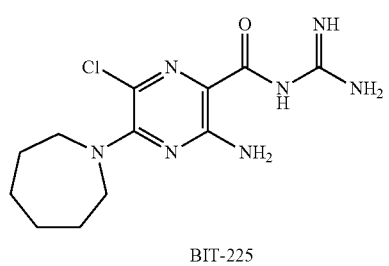
BIT-225
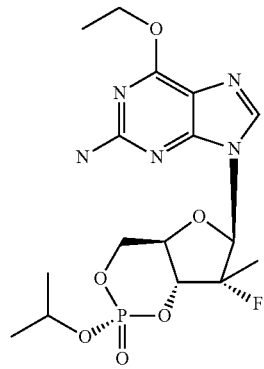
PSI-352938
PSI-352938
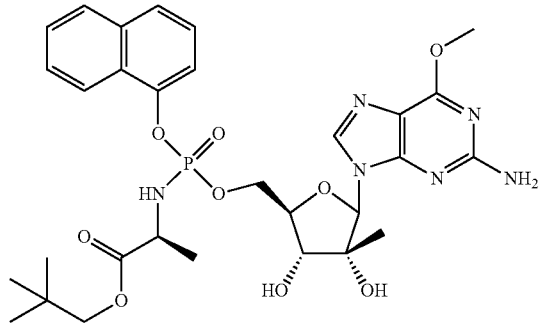
INX-189
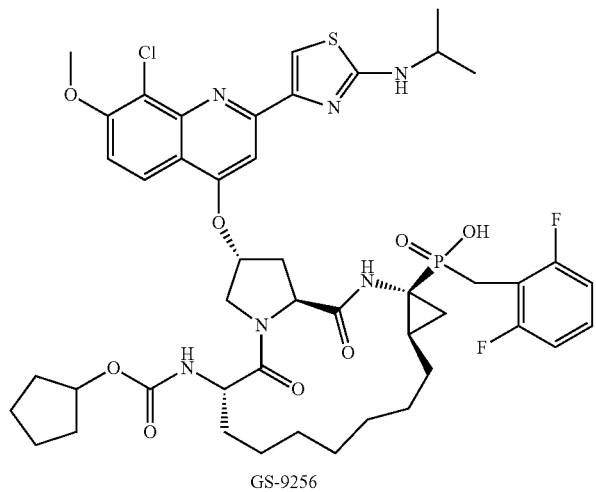
GS-9256

-continued

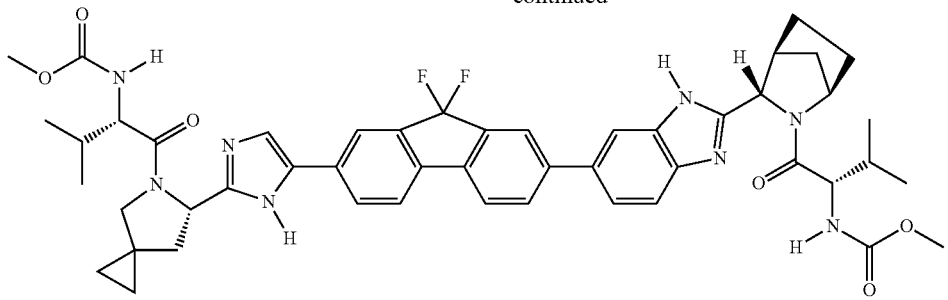

GS-5885

It has also been reported that BMS-791325 has the following structure:

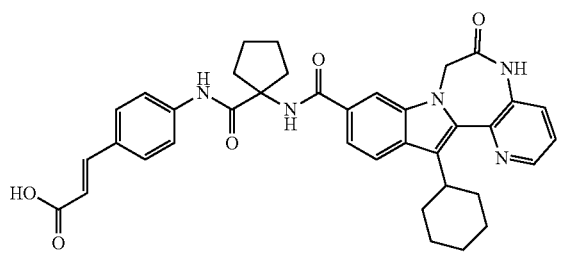

See also publications at http://www1.eas1.eu/eas12011/program/Posters/Abstract680.htm; and http://clinicaltrials.gov/show/NCT00664625. For GS-5885, see publications at http://www.natap.org/2011/EASL/EASL_68.htm; http://www1.eas1.eu/eas12011/program/Posters/Abstract1097.htm; and http://clinicaltrials.gov/ct2/show/NCT01353248.

Any HCV inhibitor or DAA described herein encompasses its suitable salt forms when it is used in therapeutic treatments or pharmaceutical formulations.

The following table lists non-limiting examples of the treatment regimens of the present technology. In each treatment regimen, the at least two DAA with or without ritonavir, are administered daily to an HCV patient under such treatment. Each treatment is interferon-free. Administration of ribavirin is included in each regimen. Each treatment regimen may also optionally comprise administering one or more other additional DAAs to the patient. The duration of each treatment regimen may last, for example and without limitation, no more than 12 weeks, no more than 11 weeks, no more than 10 weeks, no more than 9 weeks, no more than 8 weeks, alternatively no more than 7 weeks, alternatively no more than 6 weeks, alternatively no more than 5 weeks, alternatively no more than 4 weeks and may depend on the patient's response. In any given regimen described below, the drugs can be, for example and without limitation, co-formulated in a single solid dosage form when each has the same dosing frequency.

For instance, two or more drugs in a regimen can be co-formulated in amorphous forms or molecularly dispersed in a matrix comprising a water-soluble polymer and optionally a surfactant; for another instance, therapeutic agent 1 and ritonavir (RTV) are formulated in an amorphous form or molecularly dispersed in a matrix comprising a water-soluble polymer and optionally a surfactant, and therapeutic agent 3 is combined with amorphous Compound 1 and RTV in a single solid dosage form. For yet another instance, Compound 1 and RTV are formulated in a different dosage form than that of therapeutic agent 3.

TABLE 1

Non-Limiting Examples of Interferon-free Treatment Regimens with two or more DAAs (with ribavirin** and with or without ritonavir)

| Regimen | Drugs Used in Treatment | Suitable total daily dosages |
|---|---|---|
| 1 | Therapeutic Agent 1*+ | 150 to 250 mg (pref. 150, 200, 250 mg) |
|  | Therapeutic Agent 4 | 5 mg to 300 mg (pref. 25 mg) |
| 2 | Therapeutic Agent 1*+ | 150 to 250 mg (pref. 150, 200, 250 mg) |
|  | Therapeutic Agent 4+ | 5 mg to 300 mg (pref. 25 to 200 mg) |
|  | Therapeutic Agent 2 | 300 to 1800 mg (pref. 400 mg or 800 mg) |
| 3 | Therapeutic Agent 1*+ | 150-250 mg (pref. 150 mg or 250 mg) |
|  | Therapeutic Agent 3+ | 50 mg-1000 mg (pref. 400 mg) |
|  | Therapeutic Agent 4 | 5 mg-300 mg (pref. 25 mg-200 mg, more pref. 25 mg) |
| 4 | Therapeutic Agent 1*+ | 150-250 mg (150 mg, 200 mg or 250 mg) |
|  | Therapeutic Agent 2 | 300-1800 mg (pref. 200 mg, 800 mg) |
| 5 | Therapeutic Agent 1*+ | 50 mg to 250 mg (pref. 50 mg or 250 mg) |
|  | Therapeutic Agent 3 | 50 mg to 1000 mg (pref. 400 mg to 800 mg) |
| 6 | PSI-7977+ | 100 mg to 500 mg (pref. 200, 400 mg) |
|  | PSI-938 | 100 mg to 500 mg (pref. 300 mg) |
| 7 | BMS-790052+ | 10 mg to 200 mg (pref. 60 mg) |
|  | BMS-650032 | 300 mg to 1500 mg (pref. 1200 mg) |
| 8 | GS-5885+ | 3 mg to 200 mg (pref. 30 mg to 90 mg) |
|  | GS-9190+ | 30 mg to 90 mg (pref. 60 mg) |
|  | GS-9451 | 100 mg to 500 mg (pref. 200 mg) |
| 9 | GS-5885+ | 3 mg to 200 mg (pref. 30 to 90 mg) |
|  | GS-9451 | 100 mg to 500 mg (pref. 200 mg) |
| 10 | BI-201335+ | 100 mg to 400 mg (pref. 120 mg or 240 mg) |
|  | BI-207127 | 300 mg to 3600 mg (pref. 1200 mg to 2100 mg) |
| 11 | PSI-7977+ | 100 mg to 500 mg (pref. 400 mg) |
|  | TMC-435 | 25 mg to 200 mg (pref. 75 mg to 150 mg) |
| 12 | telaprevir+ | 1000 mg to 2500 mg (pref. 2250 mg) |
|  | VX-222 | 200 mg to 800 mg |
| 13 | Danoprevir*+ | 100 mg to 2000 mg (pref. 200 mg or 400 mg) |
|  | R7128 | 100 mg to 2000 mg (pref. 200 mg, 400 mg, 1000 mg or 2000 mg) |
| 14 | Danoprevir+ | 100 mg to 2000 mg (pref. 800 mg or 1000 mg, or 1800 mg or 2000 mg) |
|  | R7128 | 100 mg to 2000 mg (pref. 200 mg, 400 mg, 1000 mg or 2000 mg) |
| 15 | PSI-7977+ | 100 mg to 500 mg (pref. 400 mg) |
|  | daclatasvir (BMS-790052) | 10-200 mg (pref. 60 mg) |

TABLE 1-continued

Non-Limiting Examples of Interferon-free Treatment Regimens with two or more DAAs (with ribavirin** and with or without ritonavir)

| Regimen | Drugs Used in Treatment | Suitable total daily dosages |
|---|---|---|
| 16 | PSI-7977+ | 100 mg to 2000 mg (pref. 1800 mg or 2000 mg) |
|  | asunaprevir (BMS-650032) | 300-1500 mg (pref. 1200 mg) |
| 17 | PSI-7977+ | 100 mg to 500 mg (pref. 400 mg) |
|  | daclatasvir (BMS-790052) | 10-200 mg (pref. 60 mg) |
|  | asunaprevir (BMS-650032) | 300-1500 mg (pref. 1200 mg) |

*ritonavir or a suitable equivalent can be added to any one of these treatments as described and may be added to any of these treatments at a daily total dosage as described in the present technology; preferably ritonavir is co-formulated with therapeutic agent 1 or danoprevir; the dose of ritonavir preferably is 100 mg. Pref. = preferred
**in each regimen, ribavirin preferably is used in a weight based amount from 400 mg to 1400 mg (pref. 1000 to 1200 mg)

Additional non-limiting examples of interferon-free treatment regimens with two or more DAAs, with ribavirin and with or without ritonavir or a suitable equivalent, including the following: (a) Therapeutic Agent 1 at a total daily dose of 5 mg to 150 mg (pref. 5 mg, 25 mg, 50 mg, or 100 mg) with ritonavir or a suitable equivalent, and Therapeutic Agent 4 at a total daily dose of 5 mg to 150 mg (pref. 5 mg, 25 mg, 50 mg, or 100 mg); (b) Therapeutic Agent 1 at a total daily dose of 5 mg to 200 mg (pref. 5 mg, 25 mg, 50 mg, 100 mg) with ritonavir or a suitable equivalent, Therapeutic Agent 4 at a total daily dose of 5 mg to 200 mg (pref. 25 mg or 100 mg), and Therapeutic Agent 2 at a total daily dose of 200 mg to 800 mg (pref. 400 mg or 800 mg); (c) Therapeutic Agent 1 at a total daily dose of 5 mg to 150 mg (pref. 5 mg, 25 mg, 50 mg, or 100 mg) with ritonavir or a suitable equivalent, Therapeutic Agent 3 at a total daily dose of 100 mg to 600 mg (pref. 400 mg), and Therapeutic Agent 4 at a total daily dose of 5 mg to 300 mg (pref. 25 mg to 200 mg, more pref. 25 mg); (d) Therapeutic Agent 1 at a total daily dose of 5 mg to 150 mg (pref. 5 mg, 25 mg, 50 mg, 100 mg) with ritonavir or a suitable equivalent, and Therapeutic Agent 2 at a total daily dose of 200-800 mg; (e) GS-5885 at a total daily dose of 3-200 mg (pref. 30-90 mg). GS-9190 at a total daily dose of 30-90 mg (pref. 60 mg), and GS-9451 at a total daily dose of 100-500 mg (pref. 200 mg); (f) GS-5885 at a total daily dose of 3 mg to 200 mg (pref. 30 mg, 60 mg, or 90 mg), and GS-9451 at a total daily dose of 100 mg to 500 mg (pref. 200 mg); (g) BI-201335 at a total daily dose of 100 mg to 400 mg (pref. 120 mg, 240 mg), and BI-207127 at a total daily dose of 300 mg to 3600 mg (pref. 1200 or 1500 mg, 1800 mg or 2100 mg); (h) PSI-7977 at a total daily dose of 100 mg to-500 mg (pref. 100, 200 mg), and TMC-435 at a total daily dose of 25 mg to 200 mg (pref. 75 mg, 100 mg, or 150 mg); (i) telaprevir at a total daily dose of 1000 mg to 2500 mg (pref. 1500 mg or 2250 mg), and VX-222 at a total daily dose of 100 mg to 800 mg (pref. 100 mg, 200 mg, 400 mg, 600 mg or 800 mg); (j) INX-189 at a total daily dose of 5 mg to 400 mg (pref. 50 mg, 100 mg or 200 mg), and daclatasvir (BMS-790052) at a total daily dose of 10 mg to 200 mg (pref. 60 mg); (k) INX-189 at a total daily dose of 5 mg to 400 mg (pref. 50 mg, 100 mg or 200 mg), and asunaprevir (BMS-650032) at a total daily dose of 300 mg to 1500 mg (pref. 1200 mg); and (l) INX-189 at a total daily dose of 5 mg to 400 mg (pref. 50 mg, 100 mg or 200 mg), daclatasvir (BMS-790052) at a total daily dose of 10 mg to 200 mg (pref. 60 mg), and asunaprevir (BMS-650032) at a total daily dose of 300 mg to 1500 mg (pref. 1200 mg). In any of these examples, ritonavir or a suitable equivalent can be added to any one of these treatments as described and may be added to any of these treatments at a daily total dosage as described in the present technology; preferably ritonavir is co-formulated with therapeutic agent 1 or danoprevir; the dose of ritonavir preferably is 100 mg. In these examples, ribavirin preferably is used in a weight based amount from 400 mg to 1400 mg (pref. 1000 to 1200 mg).

The treatments of the present technology may be effective in treating HCV infection against HCV genotypes 1, 2, 3, 4, 5, 6, including subgenotypes, such as 1a, 1b, 2a, and 3a.

In general and depending on patients' conditions, the total daily dose of the DAAs of the present technology may be administered (either as a single or divided dose) in amounts from about 0.001 mg/kg to about 200 mg/kg, or from about 0.001 mg/kg to about 30 mg/kg, or from about 0.001 mg/kg to about 30 mg/kg, or from about 0.01 mg/kg, to about 10 mg/kg (i.e. mg of the compound or salt per kg body weight), and include any amounts or ranges there between, including, but not limited to increments of 0.001 mg/kg, 0.005 mg/kg, 0.01 mg/kg, 0.05 mg/kg, and multiple factors thereof (e.g. 0.25×, 0.5×, 1×, 2×, 3×, 5×, 10×, 100×, etc.). Suitable dosages of the DAAs of the present technology include, but are not limited to, from about 25 mg to about 2000 mg, from about 25 mg to about 1500 mg, from about 25 mg to about 1600 mg, from about 25 mg to about 1000 mg, from about 25 mg to about 800 mg, from about 25 mg to about 500 mg, from about 25 mg to about 250 mg, from about 50 mg to about 2000 mg, from about 50 mg to about 1500 mg, from about 50 mg to about 1600 mg, from about 50 mg to about 1000 mg, from about 50 mg to about 800 mg, from about 50 mg to about 500 mg, from about 50 mg to about 250 mg, and include, but are not limited to, for example, about 25 mg, about 30 mg, about 35 mg, about 40 mg, about 45 mg, about 50 mg, about 55 mg, about 60 mg, about 65 mg, about 70 mg, about 80 mg, about 90 mg, about 95 mg, about 100 mg, about 110 mg, about 120 mg, about 130 mg, about 140 mg, about 150 mg, about 160 mg, about 165 mg, about 170 mg, about 180 mg, about 190 mg, about 200 mg, about 210 mg, about 220 mg, about 230 mg, about 250 mg, and includes any increments there between, including increments of about 1 mg, about 2 mg, about 3 mg, about 4 mg, about 5 mg, about 6 mg, about 10 mg, about 15 mg, about 20 mg, about 25, and multiples thereof (e.g. 0.25×, 0.5×, 1×, 2×, 3×, 5×, 10×, 100×, etc.). It will be understood, however, that the specific dose level for any particular patient will depend upon a variety of factors including the activity of the specific compound employed, the age, body weight, general health, sex, diet, time of administration, route of administration, rate of excretion, drug combination, and the severity of the disease undergoing therapy.

The cytochrome P-450 inhibitor may be administered in any suitable amount such as, for example, in doses of from about 0.3 mg/kg to about 2 mg/kg or from about 0.6 mg/kg to about 1.5 mg/kg. As non-limiting examples, the cytochrome P-450 inhibitor may be administered in a total daily dose amount of from about 25 mg to about 300 mg, or from about 50 mg to about 250 mg, or from about 100 mg to about 200 mg. In some embodiments, the cytochrome P-450 inhibitor is administered in a total daily dose of about 100 mg to about 400 mg, preferably about 100 mg. In some embodiments, the cytochrome P-450 inhibitor is administered in a total daily dose amount of about 25 mg. In some embodiments, the cytochrome P-450 inhibitor is administered in a total daily dose amount of about 50 mg. In some embodiments, the cytochrome P-450 inhibitor is administered in a total daily dose amount of about 75 mg. In some embodiments, the cytochrome P-450 inhibitor is administered in a total daily dose amount of about 100 mg. In some embodiments, the cytochrome P-450 inhibitor is administered in a total daily dose amount of about 125 mg.

The one or more DAAs and ribavirin can be administered, for example and without limitation, concurrently or sequentially, and at the same or different frequencies. For instance, For example, one DAA can be administered immediately before or after the administration of another DAA. A short delay or time gap may exist between the administration of one DAA and that of another DAA. The frequency of administration may also be different. For example, a first DAA may be administered once a day and a second DAA may be administered twice or three times a day. For example, a first DAA with or without ritonavir may be administered once daily, and a second DAA may be administered twice daily.

The DAAs of the present technology can be co-formulated in a single dosage form. Non-limiting examples of suitable dosage forms include liquid or solid dosage forms. For example, a dosage form of Compound 1 as a solid dosage form is described in U.S. Patent Application Publication No. 2011/0312973, filed Mar. 8, 2011 and entitled "Solid Compositions", the entire content of which is incorporated herein by reference. More preferably, the dosage form is a solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form).

The DAAs of the present technology can be formulated in different dosage forms. It will be understood that the total daily dosage of the compounds and compositions to be administered will be decided by the attending physician within the scope of sound medical judgment.

In one embodiment, a method for treating a naïve subject comprises administering Therapeutic agent 1 at a dose of 150 mg once a day (QD), therapeutic agent 2 at a dose of 400 mg or 800 mg twice a day (BID), ritonavir at a dose of 100 mg once a day (QD), and an effective amount of ribavirin (for example, 1000 mg or 1200 mg, or an amount based on the weight of the subject) QD, for 12 weeks. At the end of treatment, the subject has no detectable virus.

In one embodiment, a method for treating a naïve subject comprises administering Therapeutic agent 1 at a dose of 50 mg QD, Therapeutic agent 2 at a dose of 400 mg or 800 mg BID, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In one embodiment, a method for treating a naïve subject comprises administering Therapeutic agent 1 at a dose of 250 mg QD, Therapeutic agent 2 at a dose of 400 mg BID, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In another embodiment, a method for treating a naïve subject comprises administering Therapeutic agent 1 at a dose of 150 mg QD, Therapeutic agent 2 at a dose of 400 mg BID, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In yet another embodiment, a method for treating a peginterferon+ribavirin (P/RBV) non-responder comprises administering Therapeutic agent 1 at a dose of 150 mg QD, Therapeutic agent 2 at a dose of 400 mg BID, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In yet another embodiment, a method for treating a peginterferon+ribavirin (P/RBV) non-responder comprises administering Therapeutic agent 1 at a dose of 50 mg QD, Therapeutic agent 2 at a dose of 400 mg BID, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In one embodiment, a method for treating a naïve subject comprises administering Therapeutic agent 1 at a total daily dose of 150 mg QD, Therapeutic agent 3 at a total daily dose of 400 mg QD, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In another embodiment, a method for treating a naïve subject comprises administering Therapeutic agent 1 at a total daily dose of 100 mg or 200 mg QD, Therapeutic agent 4 at a total daily dose of 25 mg QD, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

In yet another embodiment, a method for treating a naïve subject comprises administering Therapeutic agent 1 at a total daily dose of 100 mg or 150 mg QD, Therapeutic agent 2 at a total daily dose of 400 mg BID, Therapeutic agent 4 at a total daily dose of 25 mg QD, ritonavir at a dose of 100 mg QD, and an effective amount of ribavirin (for example, 1000 mg or 1200 mg, or an amount based on the weight of the subject) QD, for 12 weeks. At the end of treatment, the subject has no detectable virus.

It should be understood that the above-described embodiments and the following examples are given by way of illustration, not limitation. Various changes and modifications within the scope of the present invention will become apparent to those skilled in the art from the present description.

Example 1

Use of 2-DAA Combination with Ribavirin (RBV) to Treat Treatment-Naïve Subjects Infected with HCV Genotype 1

Previously untreated subjects having HCV infection were treated with a protease inhibitor (in combination with ritonavir), a polymerase inhibitor, and ribavirin. The treatment was without interferon.

Subjects included 11 treatment naïve, non-cirrhotic HCV genotype 1-infected subjects between the ages of 18 and 65.

All subjected had IL28B CC genotype. All subjects completed 12 weeks of therapy with Compound 1 and ritonavir (Compound 1/r) dosed in combination with Compound 3 and ribavirin (RBV). Compound 1 (150 mg once daily (QD)) was dosed with 100 mg QD ritonavir, 400 mg QD Compound 3, and weight-based amounts of RBV (1,000-1,200 mg/day dosed twice daily) in treatment naïve subjects infected with genotype (GT) 1 HCV.

HCV RNA levels were measured by TaqMan assay. Five of the eleven subjects had hepatitis C ribonucleic acid (HCV RNA) <25 IU/mL (i.e., below the limit of quantification) at 2 weeks. Another five subjects had undetectable levels of HCV RNA at 2 weeks. At week 3, three of the eleven subjects had HCV RNA levels of less than 25 IU/mL, and eight subjects had undetectable levels of HCV RNA. Ten of the eleven subjects had undetectable levels of HCV RNA at 4 weeks, and one subject had an HCV RNA level of less than 25 IU/mL. All eleven subjects had undetectable levels of HCV RNA at 5 weeks. HCV RNA levels remained undetectable in all subjects at week 6, 7, 8, 9, 10, 11 and 12. All subjects had undetectable levels of HCV RNA at post-treatment weeks 2 and 4. At post-treatment weeks 8 and 12, a single subject had detectable HCV RNA (breakthrough), and the remaining 10 subjects did not have any detectable level of HCV RNA. These remaining ten subjects were further tested at post-treatment weeks 16 and 24, and all of them had undetectable levels of HCV RNA at both timepoints. One of the remaining ten subjects unexpectedly showed detectable HCV RNA at post-treatment week 36.

Example 2A

Use of 2-DAA Combination with Ribavirin to Treat Treatment-Naïve or Non-Responder Subjects Infected with HCV Genotype 1

Group 1. Previously untreated subjects having HCV infection were treated with a protease inhibitor (in combination with ritonavir), a polymerase inhibitor, and ribavirin. The treatment was without interferon.

Subjects included 19 treatment naïve subjects between the ages of 18 and 65. One subject discontinued the study at week 3. All of the remaining 18 subjects completed 12 weeks of therapy with Compound 1/r dosed in combination with Compound 2 and RBV. Compound 1 (250 mg QD) was dosed with 100 mg QD ritonavir, 400 mg BID Compound 2, and RBV in treatment naïve subjects infected with GT1 HCV.

Group 2. Previously untreated subjects having HCV infection were treated with a protease inhibitor (in combination with ritonavir), a polymerase inhibitor, and ribavirin. The treatment was without interferon.

Subjects included 14 treatment naïve subjects between the ages of 18 and 65. One subject discontinued the study at week 1. Therefore, a total of 13 subjects were under study. All of the thirteen subjects completed 12 weeks of therapy with Compound 1/r dosed in combination with Compound 2 and RBV. Compound 1 (150 mg QD) was dosed with 100 mg QD ritonavir, 400 mg BID Compound 2, and RBV in treatment naïve subjects infected with GT1 HCV.

Group 3. Peginterferon+ribavirin (P/RBV) non-responders were treated with a protease inhibitor (in combination with ritonavir), a polymerase inhibitor, and ribavirin. The treatment was without interferon.

Subjects included 17 P/RBV non-responders between the ages of 18 and 65. Subjects were treated with Compound 1/r dosed in combination with Compound 2 and RBV for 12 weeks. Compound 1 (150 mg QD) was dosed with 100 mg QD ritonavir, 400 mg BID Compound 2, and RBV in P/RBV non-responders infected with GT1 HCV. During the treatment, four patients had breakthroughs and discontinued the study before week 7.

The baseline characteristics of the patients are shown in the table below.

TABLE 2

|  | Group 1 | Group 2 | Group 3 |
|---|---|---|---|
| Genotype (1a/1b) | 17/2 | 11/3 | 16/1 |
| IL28B: | | | |
| CC | 10 | 5 | 0 |
| CT | 7 | 7 | 11 |
| TT | 2 | 2 | 5 |
| Undetermined | 0 | 0 | 1 |
| Median baseline HCV RNA (log IU/mL) | 6.4 [4.1-7.2] | 6.9 [3.1-7.5] | 6.9 [6.0-7.8] |

Results from Group 1. Ten of the nineteen subjects had HCV RNA<25 IU/mL at 2 weeks. Another eight had undetectable levels of HCV RNA at 2 weeks. At week 3, one subject discontinued, four of the remaining 18 subjects had HCV RNA levels of less than 25 IU/mL, and fourteen of the remaining 18 subjects had undetectable levels of HCV RNA. At week 4, seventeen of the remaining 18 subjects had undetectable levels of HCV RNA; one subject had HCV RNA<25 IU/mL. At week 5, all of the remaining 18 subjects had undetectable levels of HCV RNA. At week 6, seventeen of the remaining 18 subjects had undetectable levels of HCV RNA, and one subject had HCV RNA<25 IU/mL. At weeks 7, 8, 9, 10, 11 and 12, all of the remaining 18 subjects had undetectable levels of HCV RNA (one subject was not tested at week 12). At post-treatment weeks 2, 4, 8, and 12 all of the remaining 18 subjects (including the one who was not tested at week 12 during treatment) had undetectable levels of HCV RNA. At post-treatment week 24, seventeen of the remaining 18 subjects were tested, and all of the seventeen subjects tested had undetectable levels of HCV RNA. At post-treatment week 24, all of the remaining 18 subjects were tested and found no detectable levels of HCV RNA.

Results from Group 2. Of the thirteen subjects tested, six had HCV RNA<25 IU/mL at 2 weeks. Another six subjects had undetectable levels of HCV RNA at 2 weeks. At week 3, two subjects had HCV RNA levels of less than 25 IU/mL, and ten subjects had undetectable levels of HCV RNA. Eleven of the thirteen subjects had undetectable levels of HCV RNA at 4 weeks and two had HCV RNA<25 IU/mL. At weeks 5, 6, 7, 8, 9 and 10, all thirteen subjects that were tested had undetectable levels of HCV RNA. One subject had detectable levels of HCV RNA at week 11 (the remaining 12 subjects had undetectable levels of HCV RNA at week 11), but HCV RNA levels in that subject, as well as all other subjects, were undetectable at week 12. At post-treatment weeks 2, 4, 8 and 12, all thirteen subjects tested (including the one who had detectable levels of HCV RNA at week 11 during treatment) had undetectable levels of HCV RNA. At post-treatment weeks 24, twelve of the thirteen subjects were tested and found no detectable levels of HCV RNA.

Results from Group 3. Seven of the seventeen subjects tested had HCV RNA<25 IU/mL at 2 weeks. Another seven subjects had undetectable levels of HCV RNA at 2 weeks. Three subjects had detectable levels of HCV RNA at 2 weeks. At week 3, three subjects had HCV RNA levels of less than 25 IU/mL, twelve subjects had undetectable levels of HCV RNA, and two subjects had detectable levels of HCV RNA. At week 4, two subjects had HCV RNA levels of less than 25 IU/mL, thirteen subjects had undetectable levels of HCV RNA, and two subjects had detectable levels of HCV RNA. Sixteen subjects were tested at 5 weeks; thirteen subjects had undetectable levels of HCV RNA and three subjects had detectable levels of HCV RNA. Fifteen subjects were tested at 6 weeks; twelve subjects had undetectable levels of HCV RNA and three subjects had detectable levels of HCV RNA. All thirteen subjects that were tested at 7 weeks had undetectable levels of HCV RNA. Twelve of the thirteen subjects that were tested at 8 weeks had undetectable levels of HCV RNA; one subject had HCV RNA levels of less than 25 IU/mL. All ten subjects that were tested at 9 weeks had undetectable levels of HCV RNA. Twelve of the thirteen subjects that were tested at 9 weeks had undetectable levels of HCV RNA; one subject had detectable levels of HCV RNA. Twelve of the thirteen subjects that were tested at 10 weeks had undetectable levels of HCV RNA; one subject had detectable levels of HCV RNA. Eleven of the twelve subjects that were tested at 11 weeks had undetectable levels of HCV RNA; one subject had HCV RNA levels of less than 25 IU/mL. Ten of the twelve subjects that were tested at week-12 of the treatment had undetectable levels of HCV RNA; one subject had HCV RNA levels of less than 25 IU/mL, and another subject had detectable levels of HCV RNA. The one subject that had HCV RNA levels of less than 25 IU/mL at week-12 of the treatment had breakthrough at post-treatment week 2. At post-treatment weeks 2 and 4, ten subjects that had undetectable HCV RNA at week-12 of the treatment were tested: eight of the ten subjects had undetectable levels of HCV RNA; and the remaining two subjects had detectable HCV RNA (breakthrough). The eight subjects that had undetectable HCV RNA at post-treatment weeks 2 and 4 were further test at post-treatment weeks 8 and 12 and found no detectable HCV RNA.

The seventeen non-responder subjects in Group 3 included 6 null responders and 11 partial responders. Three out of the six null responders, and five out of the eleven partial responders, achieved SVR12.

The study also showed that IL28B host genotype appeared not to have significantly impact on SVR12 in this study (including Groups 1, 2 and 3).

Example 2B

Use of 2-DAA Combination with Ribavirin to Treat Treatment-Naïve Subjects Infected with Genotype 1, 2 or 3

Genotype 1

Ten previously untreated subjects infected with HCV genotype 1 were treated with a 2-DAA combination with ribavirin. The treatment was interferon-free and was designed to last 12 weeks. The 2-DAA combination included Compound 1/r (200/100 mg QD) and Compound 4 (25 mg QD). The weight based dosing of ribavirin ranged from 1000 to 1200 mg divided twice daily. At weeks 5, 6 and 7 of the treatment, nine of the ten subjects showed no detectable HCV RNA; and the remaining one subject had HCV RNA levels of less than 25 IU/mL. At week 8 of the treatment, five of the nine subjects were tested and showed no detectable HCV RNA. At weeks 9 and 10 of the treatment, four of the five subjects were further tested and found no detectable HCV RNA. At week 11, two of the four subjects were tested and found no detectable HCV RNA.

Additional testing showed that all of the initial ten subjects at weeks 8, 9, 10 and 11 of the treatment had no detectable HCV RNA. At week 12, nine of the initial ten subjects showed undetectable HCV RNA, and one had HCV RNA levels of less than 25 IU/mL. At post-treatment week 2, all of the ten subjects were tested (including the one with HCV RNA levels of less than 25 IU/mL at week 12 of the treatment), and all ten subjects showed no detectable HCV RNA. At post-treatment weeks 4 and 8, all of the ten subjects were tested and found no detectable HCV RNA. Two of the ten subjects were further tested at post-treatment week 12 and found no detectable HCV RNA.

Genotype 2

Ten previously untreated subjects infected with HCV genotype 2 were treated with the same regimen of this Example. At week 4 of the treatment, all of the ten subjects were tested and showed no detectable HCV RNA. At weeks 5 and 6 of the treatment, all of the ten subjects were tested and found no detectable HCV RNA. At weeks 9-11 of the treatment, all of the ten subjects were further tested, and nine of them showed no detectable HCV RNA, and one subject showed HCV RNA levels of less than 25 IU/mL. At week 12 of the treatment, nine of the initial ten subjects were tested, eight of the nine subjects found no detectable HCV RNA and one showed detectable HCV RNA.

The subject showing detectable HCV RNA at week 12 of the treatment was confirmed breakthrough at post-treatment week 2. Eight of the initial ten subjects were also tested at post-treatment week 2 and found no detectable HCV RNA; seven of the initial ten subjects were further tested at post-treatment week 4 and found no detectable HCV RNA; three of the initial ten subjects were further tested at post-treatment week 8 and found no detectable HCV RNA; and one of the initial ten subject was further tested at post-treatment week 12 and found no detectable HCV RNA.

Genotype 3

Similarly, ten previously untreated subjects infected with HCV genotype 3 were treated with the same regimen of this Example. At week 5 of the treatment, two subjects had viral rebound; seven of the remaining eight subjects had no detectable HCV RNA; and one of the remaining eight subjects had HCV RNA levels of less than 25 IU/mL. At week 12 of the treatment, and among the eight non-breakthrough subjects, one subject was lost from the study, another showed detectable HCV RNA, and the remaining six found no detectable HCV RNA.

At post-treatment weeks 2, 4 and 8, two more subjects had breakthrough, and five subjects had no detectable HCV RNA.

One of the two subjects that had viral rebound at week 5 of the treatment was treated with a combination of peginterferon and ribavirin (P/RBV) starting at week 12. After four weeks of the P/RBV treatment, the subject was tested and found no detectable HCV RNA.

Example 2C

Use of 2-DAA Combination with Ribavirin to Treat Treatment-Experienced Subjects Infected with Genotype 1

Six treatment-experienced subjects with HCV genotype 1 infection were treated with a 2-DAA combination with ribavirin for 12 weeks. The treatment was interferon-free. The 2-DAA combination included Compound 1/r (200/100 mg QD) and Compound 4 (25 mg QD). The weight based dosing of ribavirin ranged from 1000 to 1200 mg divided twice daily. These patients had previously undergone a standard interferon/ribavirin therapy but were not responsive (interferon null responders).

At week 6 of the treatment, all six subjects showed no detectable HCV RNA. At week 8 of the treatment, all six subjects were tested and, among them, five showed no detectable HCV RNA and one had HCV RNA levels of less than 25 IU/mL. At weeks 10 and 12 of the treatment, all six subjects were tested and found no detectable HCV RNA.

At post-treatment weeks 2 and 4, all six subjects were tested, one had breakthrough and the remaining five subjects found no detectable HCV RNA. At post-treatment week 8, the five non-breakthrough subjects were further tested and found no detectable HCV RNA.

Example 2D

Use of 3-DAA Combination with Ribavirin to Treat Treatment-Naïve or Treatment-Experienced Subjects Infected with Genotype 1

Treatment-Naïve Patients

Six previously untreated subjects having HCV genotype 1 infection were treated with a 3-DAA combination with ribavirin for 8 weeks. The treatment was interferon-free. The 3-DAA combination included Compound 1/r (150/100 mg QD), Compound 2 (400 mg BID), and Compound 4 (25 mg QD). The weight based dosing of ribavirin ranged from 1000 to 1200 mg divided twice daily. At week 8 of the treatment, all six subjects had no detectable HCV RNA. At post-treatment weeks 2, 4, 8 and 12, all six subjects had no detectable HCV RNA.

Nine previously untreated subjects having HCV genotype 1 infection were treated with a 3-DAA combination with ribavirin for 12 weeks. The treatment was interferon-free. The 3-DAA combination included Compound 1/r (150/100 mg QD or 100/100 mg QD), Compound 2 (400 mg BID), and Compound 4 (25 mg QD). The weight based dosing of ribavirin ranged from 1000 to 1200 mg divided twice daily. At week 8 of the treatment, all nine subjects had no detectable HCV RNA. At week 12 of the treatment, all nine subjects were tested and found no detectable HCV RNA. At post-treatment weeks 2, 4, 8 and 12, all of the nine subjects were further tested and showed no detectable HCV RNA.

Treatment-Experienced Patients

Ten treatment-experienced subjects with HCV genotype 1 infection were treated with a 3-DAA combination with ribavirin: four subjects were treated for 12-week, one subject was treated for 16-week treatment, and the remaining five subjects were treated for 24-week treatment. The treatment was interferon-free. The 3-DAA combination included Compound 1/r (150/100 mg QD or 100/100 mg QD), Compound 2 (400 mg BID), and Compound 4 (25 mg QD). The weight based dosing of ribavirin ranged from 1000 to 1200 mg divided twice daily. These patients had previously undergone a standard interferon/ribavirin therapy but were not responsive (interferon null responders).

At weeks 6, 8, 10 and 12 of the treatment, all ten subjects showed no detectable HCV RNA.

At post-treatment weeks 2, 4 and 8, all of the four subjects in the 12-week treatment regimen found no detectable HCV RNA; and two of the four subjects were further tested at post-treatment week 12 and found no detectable HCV RNA. At post-treatment weeks 2, 4 and 8, the one subject in the 16-week treatment regimen found no detectable HCV RNA. One of the five subjects in the 24-week treatment regimen were tested at post-treatment weeks 2 and 4 and found no detectable HCV RNA.

Example 3

Synergistic concentrations of Compound 1 and Compound 2 in Genotype 1b HCV Replicon Assay Examples 3-5 are for illustration and do not limit the scope of this disclosure in any way. Not to be bound by any theory, the unexpected synergistic effects from combining different classes of HCV inhibitors (e.g., a combination of a protease inhibitor (such as Compound 1) and a polymerase inhibitor (such as Compound 2), or a combination of a protease inhibitor (such as Compound 1) and a NS5A inhibitor (such as compound 4)) may contribute to the effectiveness of the short-duration, interferon-free therapies of the present technology.

Materials:

A replicon cell line was derived from the human hepatoma cell line Huh7. It was derived from HCV genotype 1b (Con1), and is a bicistronic subgenomic replicon, essentially similar to those described in Science 285(5424):110-3 (1999). The first cistron of the construct contains a firefly luciferase reporter and a neomycin phosphotransferase selectable marker. Replicon cells were maintained in Dulbecco's Modified Eagle Media (DMEM) containing 100 IU/ml penicillin, 100 mg/ml streptomycin (Invitrogen), 200 mg/ml G418, an aminoglycoside antibiotic (Invitrogen) and 10% fetal bovine serum (FBS) at 37° C. and 5% CO2.

Replicon Cell Culture:

Replicon cells were seeded at a density of 5000 cells per well of a 96-well plate in 100 µl DMEM containing 5% FBS. The following day, Compounds 1 and 2 were diluted in dimethyl sulfoxide (DMSO) to generate a 200× stock in a series of 6 two-fold dilutions. The dilution series was then further diluted 100-fold in the medium containing 5% FBS.

Combination Studies:

Combination studies were performed to evaluate the interaction effects of therapeutic agent 1 and therapeutic agent 2 in the replicon assay described above. The purpose of these studies was to determine whether there are doses or concentrations of each compound where synergy or antagonism is demonstrated with the other compound. Three experiments with three plates in each experiment were performed on three separate days. Six concentrations of Compound 1 alone and six concentrations of Compound 2 alone were assayed in each plate. In addition, 36 combinations of concentrations of the two compounds were assayed for each plate. The variable analyzed was the fraction of inhibition of the luciferase signal.

The dilutions of each compound were combined with the dilutions of the other compound in a checkerboard fashion. The concentrations tested were chosen to ensure that the $EC_{50}$ for each compound alone is in the middle of the serial dilution range. Medium with inhibitor(s) was added to the cell culture plates already containing 100 µl of DMEM with 5% FBS. The cells were incubated in a tissue culture incubator at 37° C. and 5% $CO_2$ for three days. The inhibitor effects of compounds on HCV replication were determined by measuring activity of a luciferase reporter gene using a Luciferase Assay System kit (Promega) following the manufacturer's instructions. Passive Lysis buffer (30 µl, Promega) was added to each well, and the plates were incubated for 15 minutes with rocking to lyse the cells. Luciferin solution (100 µl, Promega) was added to each well and the luciferase activity was measured using a Victor II luminometer (Perkin-Elmer). To determine the $EC_{50}$, the luciferase inhibition data were analyzed using GraphPad Prism 4 software. Three experiments were performed with three replicates per experiment. The percent inhibition results were analyzed for synergy, additivity and antagonism according to the Pritchard and Shipman model (Antiviral Research 14:181-206 (1990)).

Combination Analysis:

Prichard and Shipman proposed a direct approach to solve this drug-drug interaction problem. The method was able to calculate theoretical additive effects directly from the individual dose-response curves determined in the assay. The calculated theoretical additivity was then compared to the experimental dose-response surface, and subsequently subtracted to reveal any areas of aberrant interaction. The following equation was used to calculate the theoretical additive effects:

$$Z = X + Y(1-X) = X + Y - XY,$$

where Z is the total inhibition produced by the combination of drugs X and Y, with X and Y representing the inhibition produced by drugs X and Y alone respectively.

A difference between the actual observed fraction of inhibition and the predicted value was calculated for each concentration combination for each plate in each experiment to determine whether the observed combined effect was greater than the theoretical additive effect Z calculated from the equation above. For each concentration combination, the replicates (across all plates and experiments) were used to calculate a mean difference between observed and predicted fraction of inhibition, its standard error and its two-sided 95% confidence interval.

Synergy or antagonism for a concentration combination was determined based on the following 2 rules: First, the 95% CI of the mean difference between observed and predicted fraction of inhibition at each concentration combination is calculated. If the lower bound of 95% CI is larger than zero, then the drug combination would be considered having a synergistic effect; if the upper bound of 95% CI is less than zero, then the drug combination would be considered having an antagonistic effect; otherwise, no significant antagonism or synergy at this concentration combination.

Second, the synergistic or antagonistic effect must have its relative mean difference, the absolute mean difference divided by its corresponding observed mean inhibition, greater than 1%. By doing this, small differences of statistical significance caused by very small variance could be excluded.

Combination of Therapeutic Agent 1 and Therapeutic Agent 2:

The inhibitory effects on replicons produced by each drug alone or in combination with the other at concentrations up to ten-fold above the $EC_{50}$ were examined in the genotype 1b (Con1) replicon using a checkerboard titration pattern (two-fold serial dilutions) in a standard three-day antiviral assay. The concentrations tested were chosen to ensure that the $EC_{50}$ values of the compounds were in the middle of the serial dilution range. For Compound 1, concentrations ranged from 0.031 nM to 1.0 nM. For Compound 2, concentrations ranged from 0.125 nM to 4.0 nM. Synergy, additivity, and antagonism were evaluated using the Pritchard and Shipman model.

Figure 2:
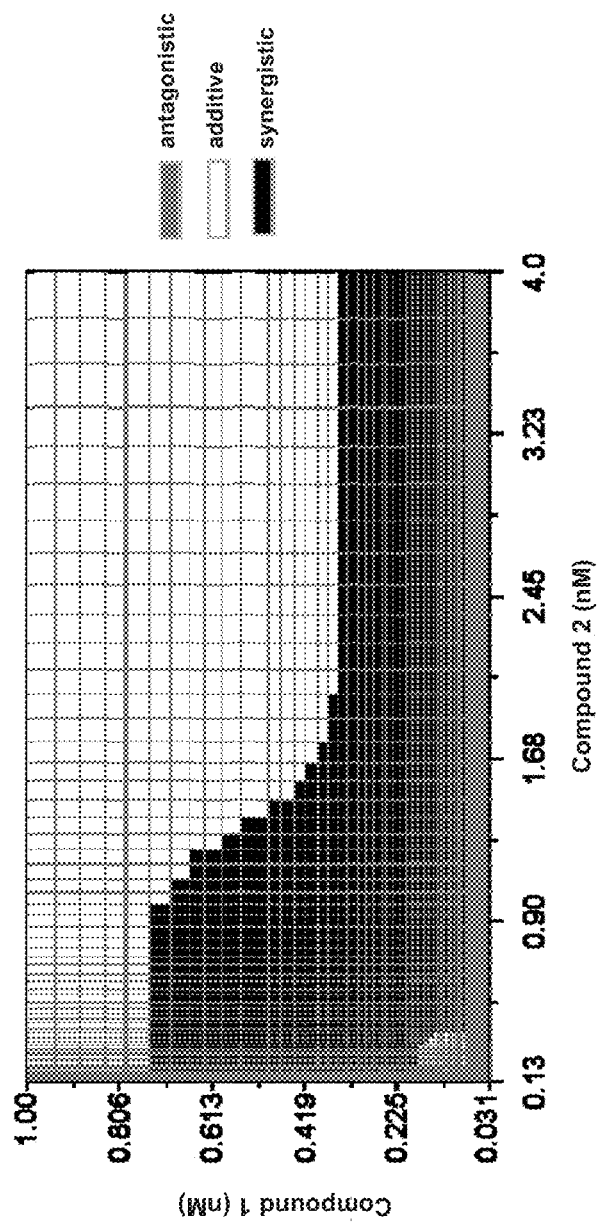
FIG. 2 is a contour plot showing concentrations at which Compound 1 and Compound 2 exhibited syngeristic, additive, or antagonistic interactions in the genotype 1b HCV replicon assay.

Results:

The results of the assay analysis are illustrated in FIGS. 1 and 2 and Table 3. In the 3-D surface plot of FIG. 1, deviations from expected interactions between Compound 1 and Compound 2 are purely additive at concentrations associated with a horizontal plane at 0%. Synergistic interactions between Compound 1 and Compound 2 appear as a peak above the horizontal plane with a height corresponding to the percent above calculated additivity. Antagonistic interactions between Compound 1 and Compound 2 appear as a pit or trough below the horizontal plane with a negative value signifying the percent below the calculated additivity. Synergistic interactions appear as dark grey, additive interactions appear white, and antagonistic interactions appear as speckled.

As illustrated in the 3-D surface plot of FIG. 1 and the contour plot of FIG. 2, an additive or synergistic effect exists at most of the concentrations for Compound 1 and Compound 2. In particular, there is a concentration region showing synergy at most concentrations of Compound 1 and at the lower to mid-range dose concentrations of Compound 2.

Table 3 below lists combinations of concentrations of Compound 1 and Compound 2 with statistically significant synergistic or antagonistic effects based on the Prichard and Shipman model analysis. For each combination of concentrations, Table 3 includes the mean difference in the observed and predicted fraction of inhibition, the standard deviation or error of the mean difference, and the upper and lower limits of the 95% confidence interval.

According to Table 3, all of the combinations of Compound 1 and Compound 2 listed in the table have statistically significant synergistic effects.

The results presented in FIGS. 1 and 2 and Table 3 demonstrate that the combination of therapeutic agent 1 and therapeutic agent 2 achieves additivity or synergy at most of the concentration combinations of the two agents. Taken together, these in vitro replicon results suggest that therapeutic agent 2 should produce a significant antiviral effect in patients when administered in combination with therapeutic agent 1 in patients infected with HCV.

TABLE 3

| Compound 2, nM | Compound 1, nM | Mean difference in fraction of inhibition: Observed − Predicted | Standard error of mean difference | Lower 95% confidence limit | Upper 95% confidence limit |
| --- | --- | --- | --- | --- | --- |
| .125 | .12500 | 0.06176 | 0.023352 | 0.007912 | 0.11561 |
| .125 | .25000 | 0.05321 | 0.022199 | 0.002024 | 0.10440 |
| .125 | .50000 | 0.01176 | 0.002680 | 0.005583 | 0.01794 |
| .250 | .25000c | 0.06626 | 0.020630 | 0.018692 | 0.11384 |
| .250 | .50000 | 0.01061 | 0.002677 | 0.004438 | 0.01679 |
| .500 | .06250 | 0.04373 | 0.014897 | 0.009375 | 0.07808 |
| .500 | .12500 | 0.10416 | 0.026757 | 0.042454 | 0.16586 |
| .500 | .25000 | 0.09327 | 0.019859 | 0.047471 | 0.13906 |
| .500 | .50000 | 0.01422 | 0.003333 | 0.006535 | 0.02191 |
| 1.00 | .06250 | 0.06696 | 0.020488 | 0.019715 | 0.11421 |
| 1.00 | .12500 | 0.14103 | 0.021289 | 0.091939 | 0.19013 |
| 1.00 | .25000 | 0.11027 | 0.016762 | 0.071617 | 0.14892 |
| 1.00 | .50000 | 0.01365 | 0.002312 | 0.008315 | 0.01898 |
| 2.00 | .06250 | 0.05974 | 0.007690 | 0.042004 | 0.07747 |

TABLE 3-continued

| Compound 2, nM | Compound 1, nM | Mean difference in fraction of inhibition: Observed − Predicted | Standard error of mean difference | Lower 95% confidence limit | Upper 95% confidence limit |
| --- | --- | --- | --- | --- | --- |
| 2.00 | .12500 | 0.10032 | 0.011820 | 0.073066 | 0.12758 |
| 2.00 | .25000 | 0.07117 | 0.009428 | 0.049428 | 0.09291 |
| 4.00 | .03125 | 0.03235 | 0.003950 | 0.023236 | 0.04145 |
| 4.00 | .06250 | 0.05141 | 0.004313 | 0.041470 | 0.06136 |
| 4.00 | .12500 | 0.06572 | 0.004692 | 0.054901 | 0.07654 |
| 4.00 | .25000 | 0.03452 | 0.004775 | 0.023509 | 0.04553 |

Example 4

Synergistic Concentrations of Compound 1 and Compound 4 in Genotype 1b HCV Replicon Assay Materials:

The replicon cell line was derived from the human hepatoma cell line Huh7. It was derived from HCV genotype 1b (Con1), and is a bicistronic subgenomic replicon, essentially similar to those described in Science 285(5424):110-3 (1999). The first cistron of the construct contains a firefly luciferase reporter and a neomycin phosphotransferase selectable marker. Replicon cells were maintained in Dulbecco's Modified Eagle Media (DMEM) containing 100 IU/ml penicillin, 100 mg/ml streptomycin (Invitrogen), 200 mg/ml G418 (Invitrogen) and 10% fetal bovine serum (FBS) at 37° C. and 5% $CO_2$.

Replicon Cell Culture:

Replicon cells were seeded at a density of 5000 cells per well of a 96-well plate in 100 µl DMEM containing 5% FBS. The following day, compounds were diluted in dimethyl sulfoxide (DMSO) to generate a 200× stock in a series of 6 two-fold dilutions. The dilution series was then further diluted 100-fold in the medium containing 5% FBS.

Combination Studies:

Combination studies were performed to evaluate the interaction effects of therapeutic agent 1 and therapeutic agent 4 in the replicon assay described above. The purpose of these studies was to determine doses or concentrations of each compound where synergy or antagonism is demonstrated with the other compound. Three experiments with three plates in each experiment were performed on three separate days. Six concentrations of Compound 1 alone and six concentrations of Compound 2 alone were assayed in each plate. In addition, 36 combinations of concentrations of the two compounds were assayed for each plate. The variable analyzed was the fraction of inhibition of the luciferase signal.

The dilutions of each compound were combined with the dilutions of the other compound in a checkerboard fashion. The concentrations tested were chosen to ensure that the $EC_{50}$ for each compound alone is in the middle of the serial dilution range. Medium with inhibitor(s) was added to the cell culture plates already containing 100 µl of DMEM with 5% FBS. The cells were incubated in a tissue culture incubator at 37° C. and 5% $CO_2$ for three days. The inhibitor effects of compounds on HCV replication were determined by measuring activity of a luciferase reporter gene using a Luciferase Assay System kit (Promega) following the manufacturer's instructions. Passive Lysis buffer (30 µl, Promega) was added to each well, and the plates were incubated for 15 minutes with rocking to lyse the cells. Luciferin solution (100 µl, Promega) was added to each well and the luciferase activity was measured using a Victor II luminometer (Perkin-Elmer). To determine the $EC_{50}$, the luciferase inhibition data were analyzed using GraphPad Prism 4 software. Three experiments were performed with three replicates per experiment. The percent inhibition results were analyzed for synergy, additivity and antagonism according to the Pritchard and Shipman model (Antiviral Research 14:181-206 (1990)).

Combination Analysis:

The Prichard and Shipman approach to calculating theoretical additive effects (described in Example 3) was used for the present example.

The difference between the actual observed fraction of inhibition and the predicted value was calculated for each concentration combination for each plate in each experiment to determine whether the observed combined effect was greater than the theoretical additive effect Z calculated from the Prichard and Shipman equation. For each concentration combination, the replicates (across all plates and experiments) were used to calculate a mean difference between observed and predicted fraction of inhibition, its standard error and its two-sided 95% confidence interval.

Synergy or antagonism for a concentration combination was determined based on the same rules set forth in Example 3.

Combination of Therapeutic Agent 1 and Therapeutic Agent 4:

The inhibitory effects in replicon produced by each drug alone or in combination with the other at concentrations up to ten-fold above the $EC_{50}$ were examined in the genotype 1b (Con1) replicon using a checkerboard titration pattern (two-fold serial dilutions) in the standard three-day antiviral assay. The concentrations tested were chosen to ensure that the $EC_{50}$ values of the compounds were in the middle of the serial dilution range. For compound 4, concentrations ranged from 0.0002 nM to 0.0063 nM, and for Compound 1, concentrations ranged from 0.023 nM to 0.75 nM. Synergy, additivity, and antagonism were evaluated using the Pritchard and Shipman model.

Figure 3:
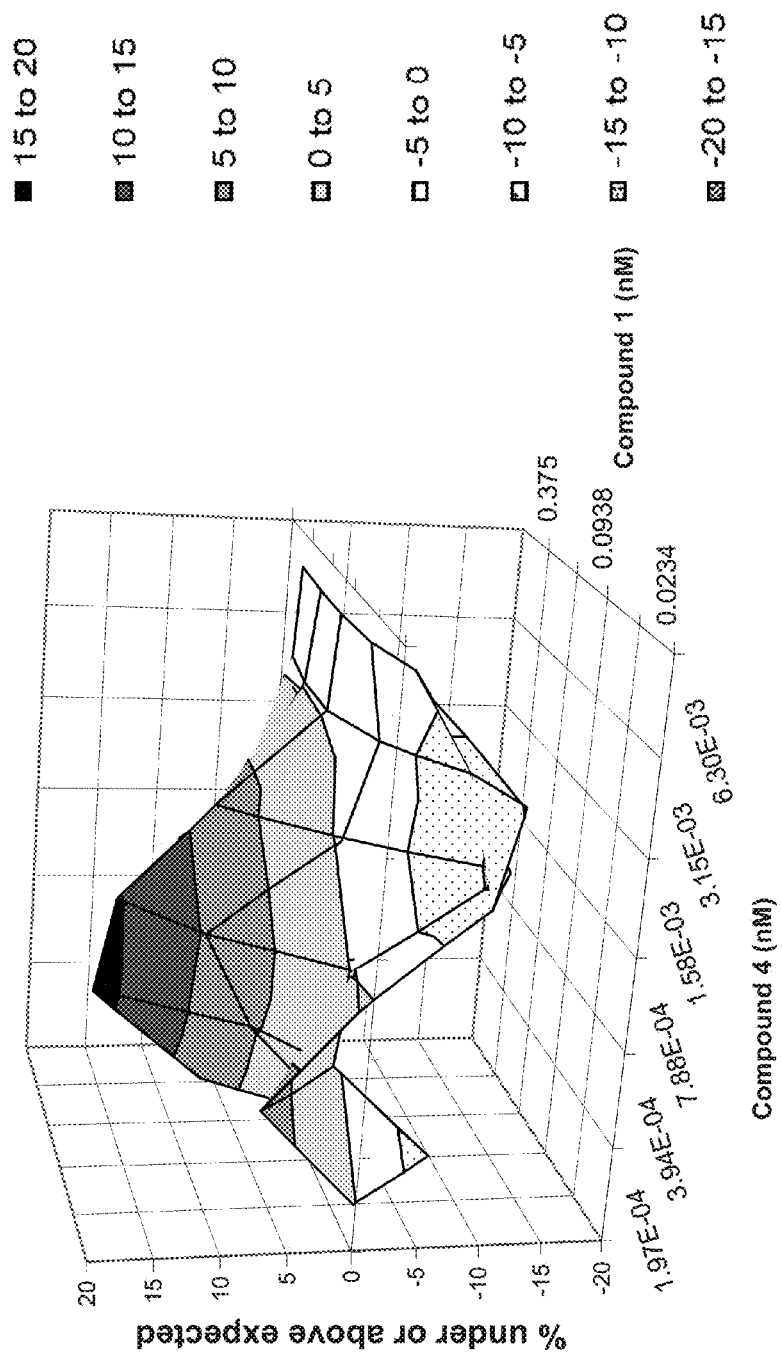
FIG. 3 is a 3-D surface plot illustrating deviations from expected inhibitory effects from varying concentrations of Compound 1 and compound 4 in a genotype 1b HCV replicon assay.
Figure 4:
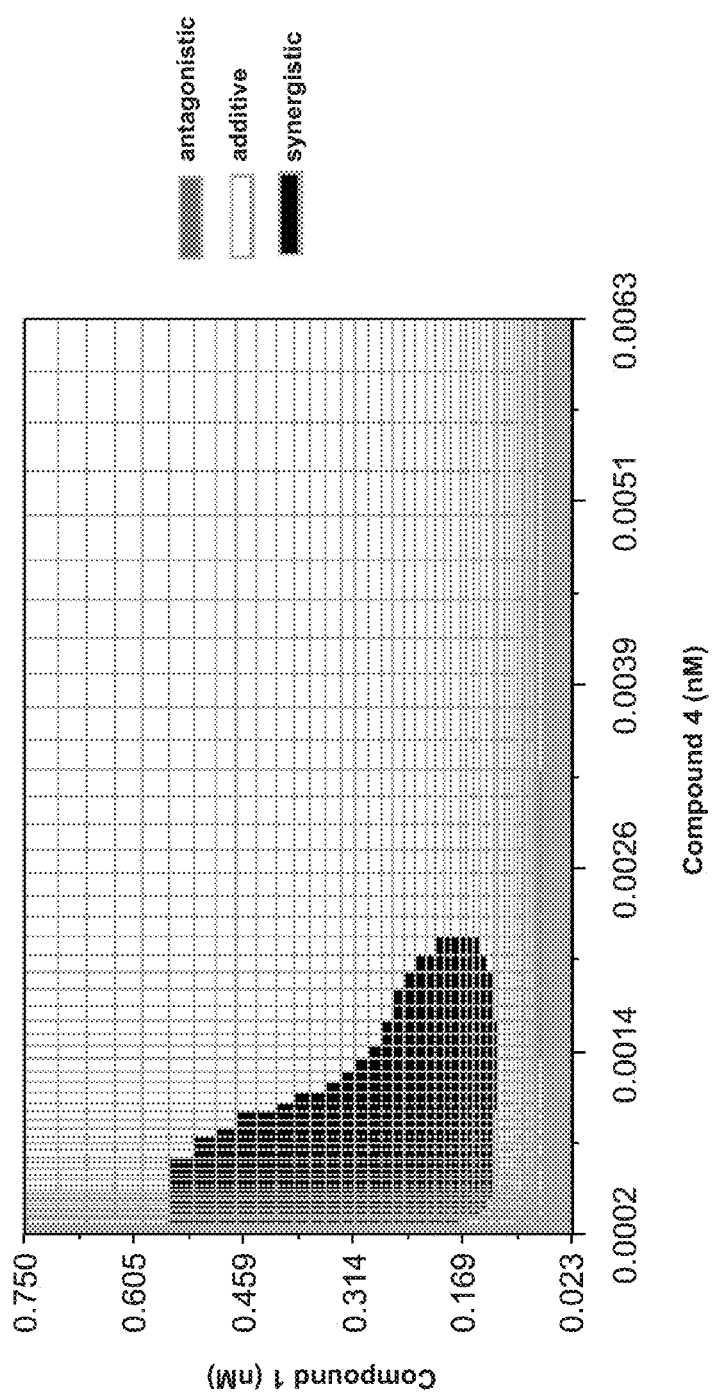
FIG. 4 is a contour plot showing concentrations at which Compound 1 and compound 4 exhibited syngeristic, additive, or antagonistic interactions in the genotype 1b HCV replicon assay.

Results:

The results of the assay analysis are illustrated in FIGS. 3 and 4 and Table 4. In the 3-D surface plot of FIG. 3, deviations from expected interactions between Compound 1 and compound 4 are purely additive at concentrations associated with a horizontal plane at 0%. Synergistic interactions between Compound 1 and compound 4 appear as a peak above the horizontal plane with a height corresponding to the percent above calculated additivity. Antagonistic interactions between Compound 1 and compound 4 appear as a pit or trough below the horizontal plane with a negative value signifying the percent below the calculated additivity. Synergistic interactions appear as shades of dark grey, additive interactions appear white, and antagonistic interactions appear as speckled.

As illustrated in the 3-D surface plot of FIG. 3 and the contour plot of FIG. 4, an additive or synergistic effect exists at most of the concentrations for Compound 1 and compound 4. In particular, there is a concentration region showing synergy at the lower dose concentrations of compound 4 and mid-range dose concentrations of Compound 1.

Table 4 below lists combinations of concentrations of Compound 1 and compound 4 with statistically significant synergistic or antagonistic effects based on the Prichard and Shipman Model analysis. For each combination of concentrations, Table 4 includes the mean difference in the observed and predicted fraction of inhibition, the standard deviation or error of the mean difference, and the upper and lower limits of the 95% confidence interval.

According to Table 4, most of the combinations of Compound 1 and compound 4 listed in the table have statistically significant synergistic effects. A small amount of antagonism was observed at the lowest concentrations of Compound 1.

Figure 5A:
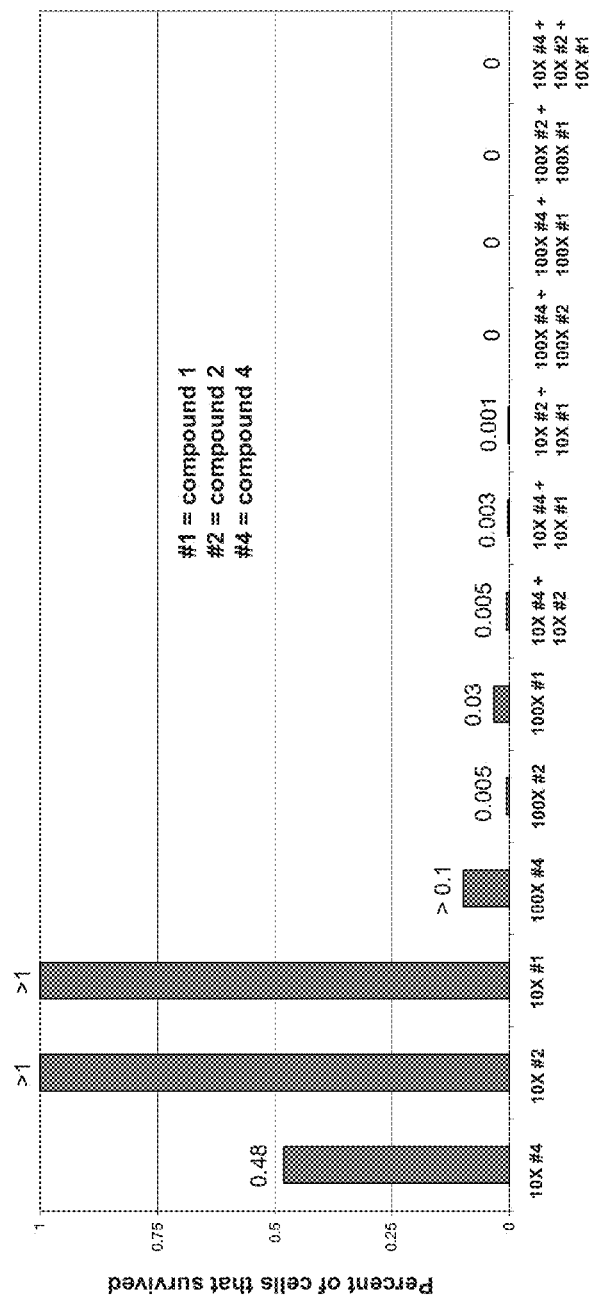
FIG. 5A is a bar graph showing the percentage of cells containing HCV genotype 1a replicon constructs surviving after three weeks of exposure to therapeutic agent 1, therapeutic agent 2, therapeutic agent 4, or a combination of some or all of those therapeutic agents in the presence of G418.

The results presented in FIGS. 3 and 4 and Table 4 demonstrate that the combination of therapeutic agent 4 and therapeutic agent 1 achieves additivity at most of the concentration combinations of the two agents and achieves synergy at certain concentration combinations, in particular, at low concentrations of therapeutic agent 4 and mid-range concentrations of therapeutic agent 1. Taken together, these in vitro replicon results suggest that therapeutic agent 4 should produce a significant antiviral effect in patients when administered in combination with therapeutic agent 1 in patients infected with HCV.

presence of G418 (400 μg/ml) and Compound 1, Compound 2, and/or compound 4 at concentrations that were either 10-fold (10×) or 100-fold (100×) above the EC50 value for the HCV genotype 1a replicon cell line. The EC50 values for Compound 1, Compound 2, and compound 4 used for this experiment were 0.9, 7.7, and 0.01 nM, respectively. After three weeks of treatment, the majority of replicon cells were cleared of replicon RNA and, therefore, were unable to survive in the G418-containing medium since the replicon RNA included the neo marker conferring G418 resistance. The cells containing resistant replicon variants survived and formed colonies, and these colonies were stained with 1% crystal violet in 10% Protocol SafeFix II reagent (Fisher Scientific), and counted. As shown in FIG. 5A, the combination of compound 4 plus either Compound 1 or Compound 2 at either 10-fold or 100-fold above their respective EC50 value resulted in significantly fewer colonies than either Compound 1, Compound 2, or compound 4 alone at 10-fold or 100-fold above their respective EC50 value.

Figure 5B:
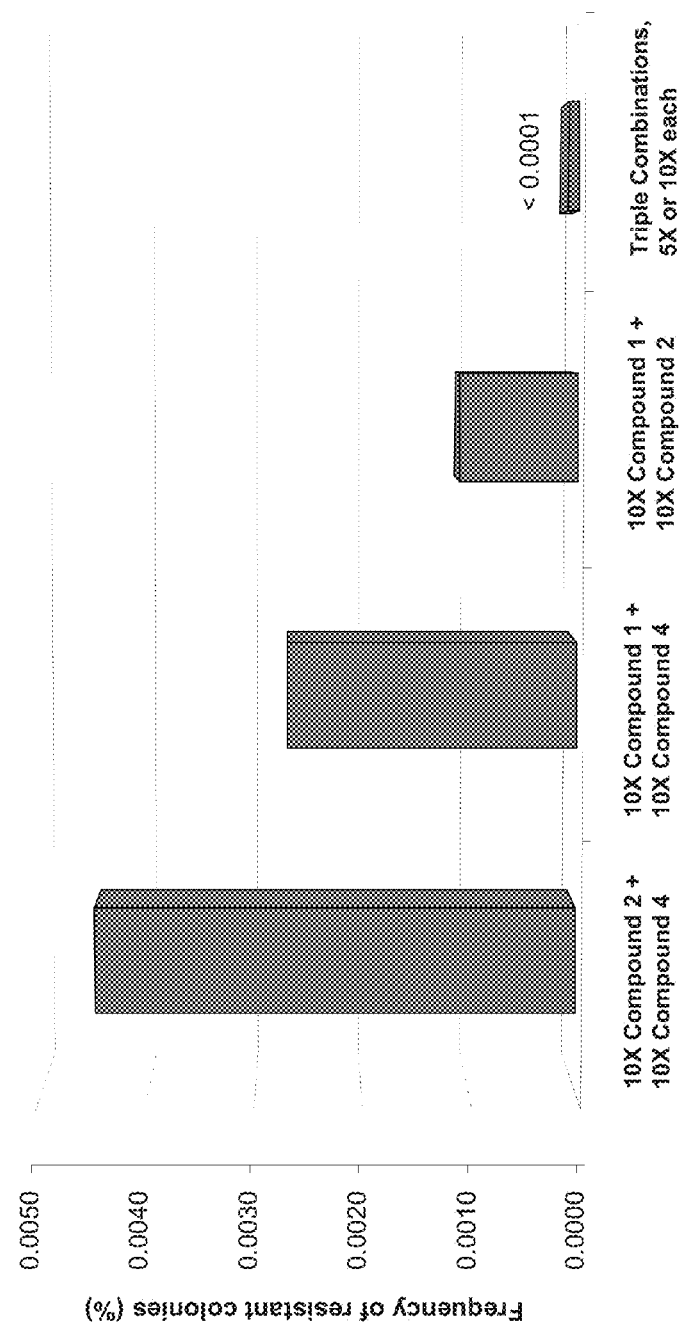
FIG. 5B is another bar graph showing the percentage of surviving 1a-H77 replicon cells grown in the presence of G418, and two or three DAA combinations, for approximately three weeks.

FIG. 5B illustrates the percentage of colonies surviving two vs. three DAA combinations. In colony survival assays, 1a-H77 replicon cells were grown in the presence of a DAA combination and G418 for approximately three weeks, after which time the cells containing resistant replicon variants had formed colonies. The cells were stained with crystal violet and counted. "Triple Combination" is either a combination of

TABLE 4

| Compound 4, nM | Compound 1, nM | Mean difference in fraction of inhibition: Observed − Predicted | Standard error of mean difference | Lower 95% confidence limit | Upper 95% confidence limit |
| --- | --- | --- | --- | --- | --- |
| 0.000197 | 0.375000 | 0.09895 | 0.033975 | 0.02060 | 0.17729 |
| 0.000394 | 0.187500 | 0.16900 | 0.038934 | 0.07922 | 0.25878 |
| 0.000394 | 0.375000 | 0.11401 | 0.027710 | 0.05011 | 0.17791 |
| 0.000788 | 0.187500 | 0.15349 | 0.038860 | 0.06388 | 0.24310 |
| 0.000788 | 0.375000 | 0.09992 | 0.027266 | 0.03704 | 0.16279 |
| 0.001575 | 0.023438 | −0.08326 | 0.027126 | −0.14582 | −0.02071 |
| 0.001575 | 0.046875 | −0.11894 | 0.026099 | −0.17913 | −0.05876 |
| 0.001575 | 0.187500 | 0.07958 | 0.020080 | 0.03328 | 0.12588 |
| 0.003150 | 0.023438 | −0.10156 | 0.018406 | −0.14401 | −0.05912 |
| 0.003150 | 0.046875 | −0.08091 | 0.014615 | −0.11462 | −0.04721 |

Example 5

Reduction of HCV-Infected Cells with Combinations of Therapeutic Agents 1, 2 and 4

In order to quantify the frequency of resistant replicon colonies selected by therapeutic agent 1, therapeutic agent 2, therapeutic agent 4, or various combinations of these agents, the stable subgenomic replicon cell line derived from HCV genotype 1a (H77; Genbank accession number AF011751) was utilized. The replicon construct was bicistronic and the cell line was generated by introducing the constructs into cell lines derived from the human hepatoma cell line Huh-7. The replicon also has a firefly luciferase reporter and a neomycin phosphotransferase (Neo) selectable marker. The two coding regions, separated by the FMDV 2a protease, comprise the first cistron of the bicistronic replicon construct, with the second cistron containing the HCV NS3-NS5B coding region with addition of adaptive mutations E1202G, K1691R, K2040R and S2204I. This HCV replicon cell line was maintained in Dulbecco's modified Eagles medium (DMEM; Invitrogen) containing 10% (v/v) fetal bovine serum, 100 IU/ml penicillin, 100 μg/ml streptomycin, and 200 μg/ml G418 (all from Invitrogen). 1a-H77 replicon cells (105-106) were plated in 150 mm cell culture plates and grown in the Compounds 1, 2 and 4 at concentrations of 5-fold (5×) over their respective EC50 values, or a combination of Compounds 1, 2 and 4 at concentrations of 10-fold (10×) over their respective EC50 values.

Figure 5C:
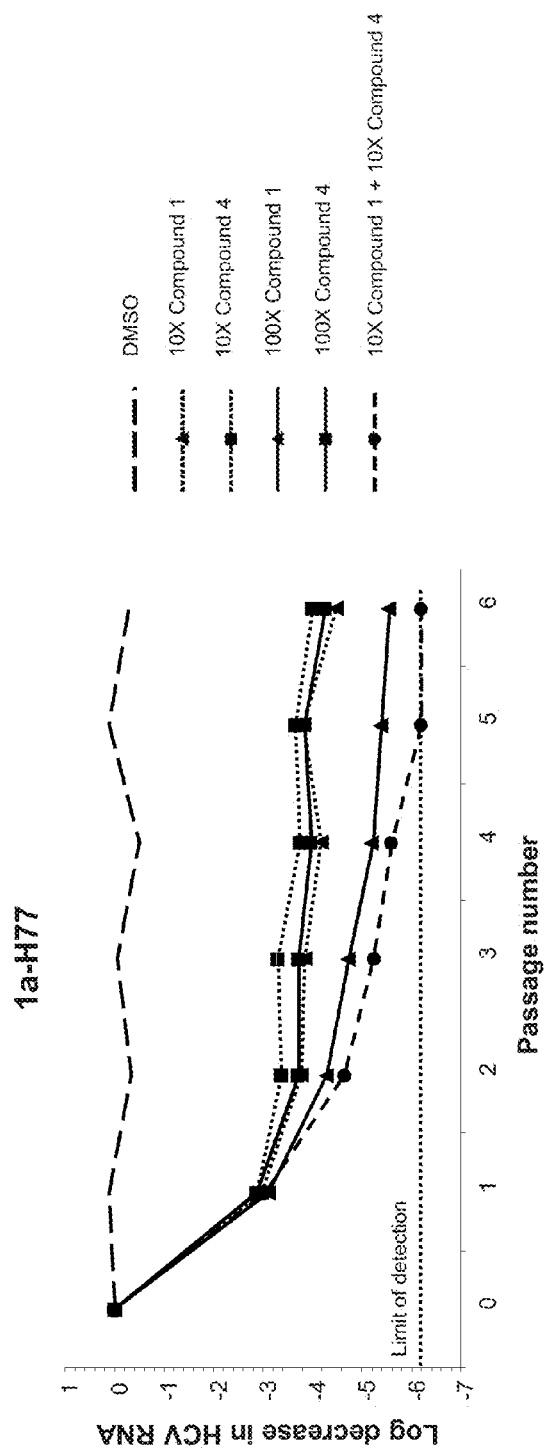
FIG. 5C depicts the effect of Compound 1, Compound 2 and a combination thereof in long-term HCV RNA reduction assays in 1a-H77 replicon cell lines.
Figure 5D:
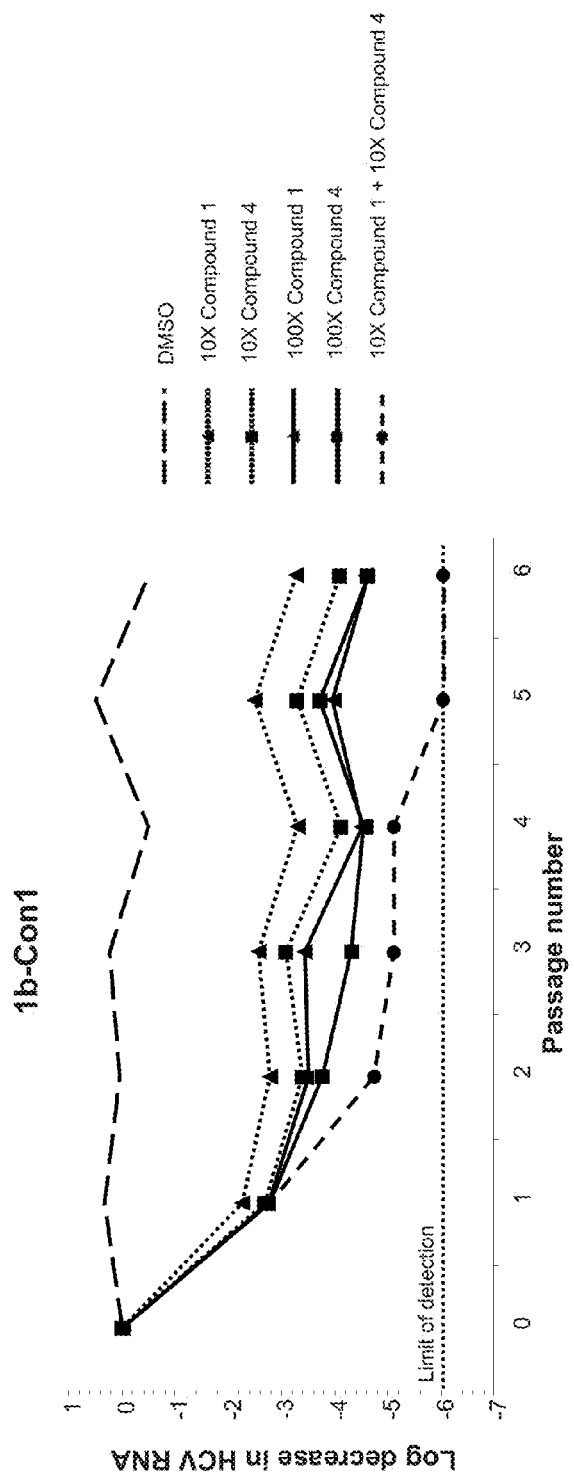
FIG. 5D demonstrates the effect of Compound 1, Compound 2 and a combination thereof in long-term HCV RNA reduction assays in 1b-Con1 replicon cell lines.

FIGS. 5C and 5D show the effect of a combination of Compounds 1 and 4 in long-term HCV RNA reduction assays in genotype 1 replicon cell lines. In long-term replicon RNA reduction assays, 106 replicon cells were plated in the absence of G418. The inhibitors at concentrations of either 10-fold (10×) or 100-fold (100×) over their respective $EC_{50}$ values were added, and the cells were grown to approximately 95% confluence (4 days). At each passage, 106 cells were removed and frozen, and an additional 106 cells were passed into another flask with fresh media and inhibitors. RNA was extracted from 106 cells and HCV RNA was measured in a Real-Time RT-PCR assay. FIGS. 5C and 5D show that in both 1a and 1b replicon cells, the combination of Compounds 1 and 4, each at 10-fold over $EC_{50}$, is more effective at clearing cells of replicon than 100-fold over $EC_{50}$ of either inhibitor alone.

Predominant resistant variants selected by Compound 1, 2, or 4 in genotype 1 replicons were also determined. For Compound 1, the predominant resistance variants in 1a-H77 replicons include R155K, D168A and D168V with fold resistance of 26, 48 and 128, respectively; and the predominant resistance variants in 1b-Con1 replicons include R155K, A156T and D168V with fold resistance of 48, 9 and 190, respectively. For Compound 2, the predominant resistance variants in 1a-H77 replicons include C316Y, M414T, Y448C and S556G with fold resistance of 1600, 36, 980 and 15, respectively; and the predominant resistance variants in 1b-Con1 replicons include C316Y, M414T and D559G with fold resistance of 1400, 26 and 100, respectively. For Compound 4, the predominant resistance variants in 1a-H77 replicons include M28T, M28V, Q30R, Y93C and Y93H with fold resistance of 9000, 60, 800, 1700 and 41000, respectively; and the predominant resistance variants in 1b-Con1 replicons include Y93H with fold resistance of 55. These experiments also showed that in genotype 1a, a number of variants selected by Compounds 2 or 4 conferred higher levels of resistance than those selected by Compound 1, and that in genotype 1b, one variant (C316Y) selected by Compound 2 conferred a higher level of resistance than those selected by either Compound 1 or Compound 4.

The above examples show that the combination of two different classes of DAAs (e.g., a combination of a HCV protease inhibitor and a HCV polymerase inhibitor, or a combination of a HCV protease inhibitor and a HCV NS5A inhibitor, or a combination of a HCV polymerase inhibitor and a HCV NS5A inhibitor) can lead to an improved resistance barrier in patients relative to a single DAA alone, while the combination of three different classes of DAAs (e.g., a combination of a HCV protease inhibitor, a HCV polymerase inhibitor, and a HCV NS5A inhibitor) can lead to even more significant barrier to resistance. Improvement in the barrier to resistance achieved through co-administration of multiple DAAs of different classes or with different mechanism of action is expected to correlate with enhanced efficacy in patients.

Example 6

Clinical Modeling for Interferon-Free DAA Combination Therapies

This example describes a novel clinical model for evaluating optimal doses and durations of interferon-free HCV therapies using combinations of different DAAs. This model reasonably predicted the effectiveness of numerous DAA combinations in interferon-free, short-duration therapies.

A mechanistic model was used to model the relationship between DAA exposures and antiviral efficacy in HCV-infected subjects. This model was used to conduct clinical trial simulations of clinical outcomes following administration of various DAA combination regimens (e.g., specific DAA combinations and different doses of DAAs) and durations of therapy.

Numerous DAAs have been extensively documented to select mutants following short duration of monotherapy (e.g., less than 1 week). The viral dynamic model of this Example included single and double mutants. Specifically, the model included 2 single mutants and one double mutant for each of the 2-DAA combination regimens. Thus, a 2-DAA combination regimen (e.g., a combination of a protease inhibitor and a NS5A inhibitor) included 2 single mutants and one double mutant. A 3-DAA combination (e.g., a combination of a protease inhibitor, a polymerase inhibitor and a NS5A inhibitor, such as a combination of a protease inhibitor, a non-nucleoside polymerase inhibitor (NNPI) and a NS5A inhibitor) included 3 single and 2 double mutants.

The model has 3 components: hepatocytes (uninfected or target cell), infected cell and viral dynamics. The differential equations describing the dynamics of the 3 components are as follows:

(1) Hepatocytes (Uninfected or Target Cell) Dynamics $$dT/dt = s - de*T - (1-\eta)*\beta*T*(VLWT+VLPoly+VLProt+VLNS5A+VLNS5AProt+VLPoly/Prot)$$

(2) Infected Cell Dynamics
(a) Infected with Wild type Virus $$d\,IWT/dt = (1-\eta)*\beta*T*VLWT - \delta*IWT$$

(b) Infected with Polymerase Mutant Virus $$d\,IPoly/dt = (1-\eta)*\beta*T*VLPoly - \delta*IPoly$$

(c) Infected with Protease Mutant Virus $$d\,IProt/dt = (1-\eta)*\beta*T*VLProt - \delta*IProt$$

(d) Infected with NS5A Mutant Virus $$d\,INS5A/dt = (1-\eta)*\beta*T*VLNS5A - \delta*INS5A$$

(e) Infected with Protease-NS5A Double Mutant Virus $$d\,INS5AProt/dt = (1-\eta)*\beta*T*VLNS5AProt - \delta*INS5AProt$$

(f) Infected with Protease-Polymerase Double Mutant Virus $$d\,IPolyProt/dt = (1-\eta)*\beta*T*VLPolyProt - \delta*IPolyProt$$

(3) Viral Dynamics
(a) Wild Type Virus $$d\,VLWT/dt = (1-3*\mu)*\rho*(1-Eff1)*IWT + \mu*(\rho*(1-Eff2)*Fit1*IPoly + \rho*(1-Eff3)*Fit2*IProt + \rho*(1-Eff4)*Fit3*INS5A) - c*VLWT$$

(b) Polymerase Mutant Virus $$d\,VLProt/dt = (1-\mu-\phi)*\rho*(1-Eff2)*Fit1*IPoly + \mu*\rho*(1-Eff1)*IWT + \phi*\rho*(1-Eff5)*Fit4*IPoly\text{-}Prot - c*VLPoly$$

(c) Protease Mutant Virus $$d\,VLProt/dt = (1-\mu-2*\phi)*\rho*(1-Eff3)*Fit2*IProt + \mu*\rho*(1-Eff3)*IWT + \phi*(\rho*(1-Eff5)*Fit4*IPolyProt + \rho*(1-Eff6)*Fit5*INS5AProt) - c*VLProt$$

(d) NS5A Mutant Virus $$d\,VLNS5A/dt = (1-\mu-\phi)*\rho*(1-Eff4)*Fit3*INS5A + \mu*\rho*(1-Eff1)*IWT + \phi*\rho*(1-Eff6)*Fit5*INS5AProt - c*VLNS5A$$

(e) NS5A and Protease Double Mutant Virus $$d\,VLNS5AProt/dt = (1-2*\phi)*\rho*(1-Eff6)*Fit5*INS5AProt + \phi*(\rho*(1-Eff4)*Fit3*INS5A + \rho*(1-Eff3)*Fit2*IProt) - c*VLNS5AProt$$

(f) Poly and Protease Mutant Double Mutant Virus $$d\,VLPolyProt/dt = (1-2*\phi)*\rho*(1-Eff5)*Fit4*IPolyProt + \phi*(\rho*(1-Eff2)*Fit1*IPoly + \rho*(1-Eff3)*Fit2*IProt) - c*VLPolyProt$$

The parameters used in the above equations are described in Table 5.

TABLE 5

Viral Dynamic Parameters

| Parameter | Description |
|---|---|
| s | zero-order production of hepatocytes |
| T | number of Target or uninfected hepatocytes |
| de | first-order rate constant for the death of hepatocytes |
| β | rate-constant for the infection of hepatocytes by virus |

TABLE 5-continued

Viral Dynamic Parameters

| Parameter | Description |
|---|---|
| δ | first-order rate constant for the death of infected hepatocytes |
| η | fractional reduction of the rate-constant for the infection of hepatocytes by virus |
| μ | probability of the formation of single mutants and mutation back to Wild-Type |
| φ | probability of the formation of double mutants and mutation back to single mutant |
| ρ | production rate of the Wild-Type virus |
| c | clearance rate of the virus |
| Eff1, Eff2, Eff3, Eff4 | inhibition of production of Wild Type, polymerase, protease, and NS5A mutant, respectively |
| Eff5, Eff6 | inhibition of production of polymerase-protease and NS5A-protease double mutant, respectively |
| Fit1, Fit2, Fit3 | fitness of polymerase, protease and NS5A mutant relative to wild type virus, respectively |
| Fit4, Fit5 | fitness of polymerase-protease and NS5A-protease double mutant relative to wild type virus, respectively |
| IWT, IPoly, Iprot, INS5A | number of cells infected with wild type, polymerase, protease and NS5A mutants, respectively |
| IPoly-Prot, INS5A-Prot | number of cells infected with polymerase-protease and NS5A-protease double mutant, respectively |
| VLWT, VLPoly, VLProt, VLNS5A | viral load for wild type virus, polymerase, protease and NS5A mutant virus, respectively |
| VLPoly-Prot, VLNS5A-Prot | viral load for polymerase-protease and NS5A-protease double mutant, respectively |

As shown in the differential equations for viral dynamics, the effect of DAA is included as an inhibition of viral load production. For example, the effect of DAA(s) on production of wild type virus is given as $(1-\text{Eff1})*\rho$ where Eff1 is the fraction of viral production that is inhibited. In the absence of drug Eff1=0 and in the presence of drug Eff1 takes a value between 0 and 1. Eff1 is described using an Emax model:

$$\text{Eff1} = \text{Emax}*\text{Conc}/(EC_{50}+\text{Conc})$$

where Emax represents maximum inhibition, Conc is the plasma DAA concentration and $EC_{50}$ is the concentration that inhibits viral load production by 50%. As the fold-change in $EC_{50}$ for the mutants compared to wild type virus was based on values obtained from in vitro replicon studies, $EC_{50}$ was estimated only for wild type virus.

For DAA combinations, the effect was assumed to be multiplicative and incorporated as follows:

$$(1-\text{Eff1})=(1-\text{Eff}_{DAA1})*(1-\text{Eff}_{DAA2})*(1-\text{Eff}_{DAA3})$$

The effect of ribavirin (RBV) was added on infection rate β as an Emax model. In presence of ribavirin, the infection rate decreases by a factor (1−η) where $$\eta = \text{Conc}_{RBV}/(EC_{50\text{-}RBV}+\text{Conc}_{RBV})$$

The model does not include a double mutant to the polymerase+NS5A inhibitors. In a 3-DAA regimens, a polymerase+NS5A double mutant is often wild type for the protease inhibitor. Hence, this double mutant is not expected to significantly affect clinical outcomes for a 3-DAA regimen simulation. On the other hand, the model can be readily adapted to simulate a 2-DAA regimen containing a polymerase inhibitor and a NS5A inhibitor by treating the polymerase inhibitor (e.g., PSI-7977) as a protease inhibitor in the model.

The lowest available limit of detection (LOD) of viral load assays is 10 IU/mL. Assuming 3 virion particles per IU, this constitutes about 0.5 million viruses in the body at LOD. Hence, subjects have to be treated for significant period of time after their viral load falls below the LOD to achieve cure. This duration depends on the potency of the compounds and the individual response to therapy.

In order to predict the duration required for cure, a "threshold" concept was used. For simulations, an HCV-infected subject was assumed to achieve SVR when viral load reaches less than 1 virion in the total plasma and extracellular fluid volume (about 15000 mL), i.e., viral load measurement of <1 copy/15000 mL or <0.33 IU/15000 mL. This translates to about 5 log IU/mL. Cf. Snoeck E et al., CLIN PHARMACOL THER. 87(6):706-13 (2010), wherein based on data from patients treated with peg-IFN and ribavirin, subjects were estimated to achieve SVR when the predicted number of infected cells fell below 1. While such low viral loads cannot be measured experimentally, they can be simulated using the viral dynamic model.

The model can be used to predict SVR for any combination of DAAs, with or without interferon, and with or without ribavirin.

As non-limiting examples, various interferon-free treatment regimens using different combinations of Compound 1, Compound 2 and/or Compound 4, with or without ribavirin, were evaluated using the model of this Example. The following approach was used to include mutants in the model:

a. One single mutant per DAA
b. One double mutant per DAA combination

For a combination of two DAAs, e.g., a combination of Compound 1 and Compound 2, the model included one mutant resistant to Compound 1, one mutant resistant to Compound 2, and one double mutant resistant to both Compound 1 and Compound 2. Compound 1 is coadministered or co-formulated with ritonavir (or another pharmacokinetics enhancer) to improve its drug exposure.

A double mutant to Compound 2 and Compound 4 was not included in the modeling. In the 3-DAA regimens, a Compound 2/Compound 4 double mutant is likely wild type for Compound 1 due to the high potency and resistant profile of Compound 1. Hence, the Compound 2/Compound 4 double mutant is not expected to affect clinical outcomes for treatments containing Compound 1.

Single mutants included in the model were based on mutants observed for the individual DAAs in the Phase 1b and 2a studies (e.g., clinical studies M10-351, M12-116, and M11-602). For double mutants with resistance to 2 DAA classes, the sensitivity ($EC_{50}$) of double mutants to drug was assumed to be a combination of the 2 single mutants. Thus, for Compound 1 and Compound 2, the single mutants were D168V and M414T, respectively, and the double mutant was D168V-M414T. In this scenario, the D168V mutant would be less sensitive to Compound 1 but would be as sensitive to Compound 2 as wild type virus. Similarly, the M414T mutant would be less sensitive to Compound 2 but would be as sensitive to Compound 1 as wild type virus. The double mutant D168V-M414T would be less sensitive to both Compound 1 and Compound 2.

The fold change in $EC_{50}$ for the mutants compared to wild type virus was based on values obtained from in vitro replicon studies. Since monotherapy data for Compound 4 indicated a variety of mutants with different $EC_{50}$s, a value of 1000× fold change in $EC_{50}$ was used for Compound 4 for modeling and simulations.

Baseline prevalence of the mutants was estimated during model fitting, while the mutation rate was based on the literature values. Both baseline prevalence and mutation rate determined mutant fitness.

Pharmacokinetic data and viral load data from 140 treatment-naïve HCV-infected subjects were used to construct the model. For modeling, number of target cells at baseline, number of infected cells at baseline, death rate of target cells and mutation rates were based on literature values. See, e.g., Snoeck et al. supra; Rong et al. SCI TRANSL MED. 2(30):30ra32 (2000); Neal and Pravin, ACOP 2009 (http://2009.go-acop.org/sites/all/assets/webform/Lauren-Neal_ACoP_2009.pdf); Neumann et al. SCIENCE 282(5386):103-7 (1998); Shudo et al. ANTIVIR THER. 13(7):919-26 (2008); and Dahari et al. J THEOR BIOL. 247(2):371-81 (2007). The production rate of virus and infection rate of virus were derived from other parameters in the model. All other parameters were estimated. Exposure-antiviral response modeling was performed using NONMEM 7.2.

Clinical trial simulations were performed using Trial Simulator version 2.2.1. Fifty subjects and 50 replicates were simulated for each treatment. A subject drop out rate from the study due to any reason was assumed to be 8% over 24 weeks based on available literature on trials in subjects with HCV. All simulations were conducted assuming 100% compliance. Covariates included in the simulations were genotype 1a/1b status. Clinical outcomes simulated included: (1) percentage of subjects below limit of detection (LOD) of 10 IU/mL and (2) percentage of subjects achieving SVR.

Clinical trial simulations were conducted to determine optimal dose and duration for SVR. Over 80 scenarios were simulated to predict the percentage of subjects with SVR following administration of various 2- and 3-DAA combinations (e.g., Compound 1+Compound 2, or Compound 1+Compound 4, or Compound 1+Compound 2+Compound 4), without RBV, at a range of doses for each DAA (e.g., Compound 1/ritonavir at 250/100, 150/100 or 100/100 mg QD, Compound 4 at 5, 25 or 100 mg QD, and Compound 2 at 400 or 800 mg BID) and across a range of treatment durations (e.g., 2. 4, 6, 8, 10, 12, 16, and 24 weeks).

Figure 6A:
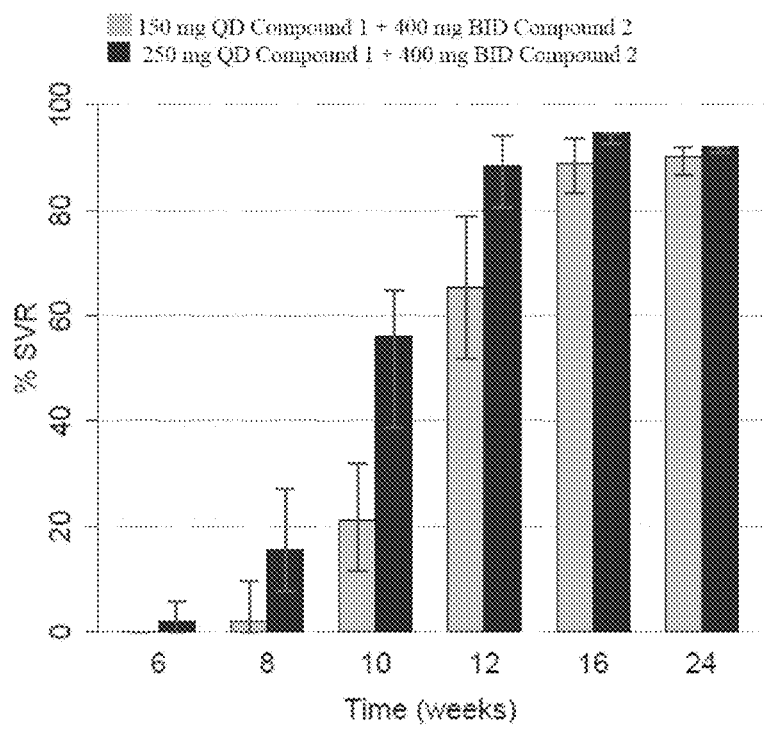
FIG. 6A shows the predicted median and 90% confidence interval of SVR percentage for different treatment durations of a 2-DAA regimen without ribavirin; the 2 DAAs include (i) Compound 1 with ritonavir (Compound 1/r) and (ii) Compound 2.
Figure 6B:
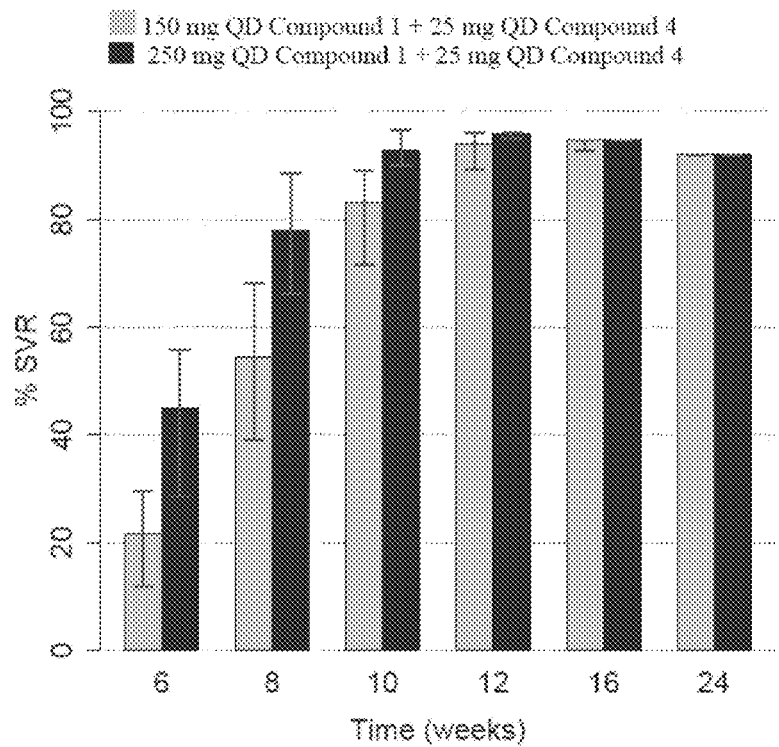
FIG. 6B illustrates the predicted median and 90% confidence interval of SVR percentage for different treatment durations of a 2-DAA regimen without ribavirin; the 2 DAAs include (i) Compound 1 with ritonavir (Compound 1/r) and (ii) Compound 4.
Figure 6C:
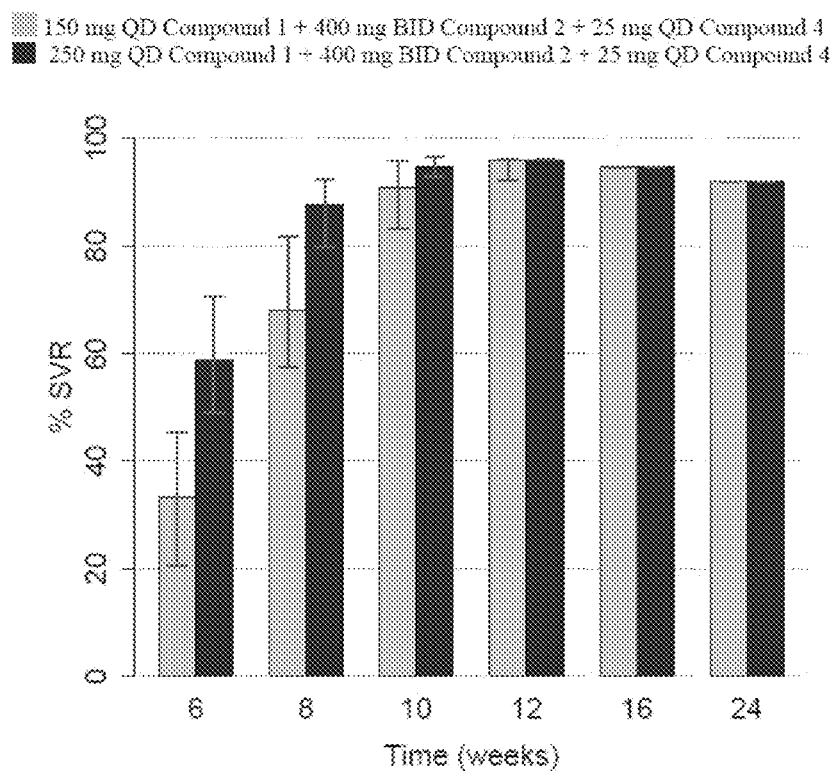
FIG. 6C depicts the predicted median and 90% confidence interval of SVR percentage for different treatment durations of a 3-DAA regimen without ribavirin; the 3 DAAs include (i) Compound 1 with ritonavir (Compound 1/r), (ii) Compound 2 and (iii) Compound 4.

Optimal dose and duration were predicted based on percentage of subjects with viral load of less than −5 log IU/mL threshold for SVR. Selected and relevant results of simulation for the 2- and 3-DAA combinations of Compounds 1, 2 and/or 4 are shown in FIGS. 6A, 6B and 6C for two different doses of Compound 1. FIG. 6A shows the predicted median SVR percentage ("% SVR") and 90% confidence interval (the vertical bar at the top of each SVR percentage column) for different treatment durations using a combination of Compound 1 and Compound 2; FIG. 6B shows the predicted median and 90% confidence interval for different treatment durations using a combination of Compound 1 and Compound 4; and FIG. 6C shows the predicted median and 90% confidence interval for different treatment durations using a combination of Compound 1, Compound 2 and Compound 4. In each simulation, RBV was included, and Compound 1 was used with 100 mg ritonavir, and the subjects are HCV genotype 1, treatment-naïve patients. SVR24 is lower than SVR12 in some cases due to drop out; longer durations are not necessarily predicted to improve SVR but could result in more dropouts resulting in lower SVR.

The model predicted that with 8-12 weeks of dosing at least 80 to 90% subjects can achieve SVR with 2 and 3 DAA combinations. The model also predicted that durations shorter than 8 weeks can cure a significant number of subjects. A 2-DAA regimen was predicted to cure over 40% of the subjects and a 3-DAA regimen was predicted to cure about 60% of the subjects with only 6 weeks of dosing. Dosing for durations of over 12 weeks was not expected to increase the percentage of subjects with SVR significantly. Addition of the $3^{rd}$ DAA was predicted to shorten treatment duration by 2 to 4 weeks as optimal durations for the 3-DAA combination of Compound 1, Compound 2 and Compound 4 were predicted to be 8-10 weeks.

FIGS. 6A, 6B and 6C illustrate the predictions for DAA combinations without ribavirin. The model also predicts similar or comparable SVR percentages for these DAA combinations when used with ribavirin. In addition, the effect of interferon (e.g., pegylated interferon) can also be added by incorporating interferon similar to a DAA but without any resistant mutants.

One of the advantages that the model provides is that it allows examination of various viral parameters and its effect on dose, duration and SVR. For example while experimentally determining the effect of mutants parameters is very difficult if not impossible, they can be examined using the model. Thus SVR in patient population that have different mutants can be predicted with the model.

Figure 7:
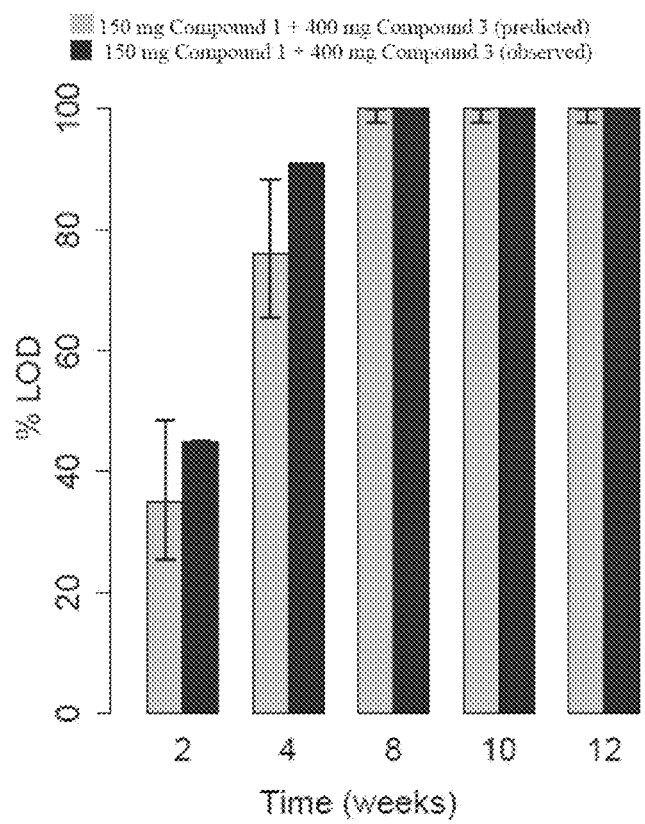
FIG. 7 shows the exposure-response model predicted versus observed percentage of subjects with HCV RNA less than LOD over time in the clinical study described in Example 1.

The model was used to simulate the treatment described in Example 1 which included 150/100 mg Compound 1/ritonavir QD+400 mg Compound 3 QD+weight-based amounts of RBV BID for 12 weeks, and the percentage of subjects with HCV RNA less than LOD at 2, 4, 8, 10, and 12 weeks was summarized in FIG. 7. The mean predicted versus observed percentage of subjects with below LOD ("% LOD") at respective weeks are shown FIG. 7. 95% confidence intervals for the predicted data (the vertical bar at the top of each respective predicted LOD percentage column) were also indicated. As shown in FIG. 7, the model reasonably predicted the clinical outcome of % LOD.

Figure 8:
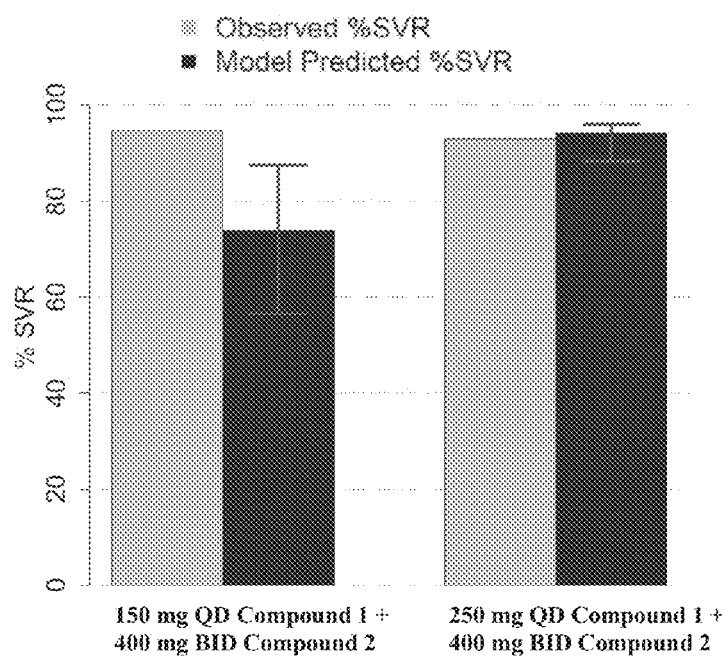
FIG. 8 demonstrates the exposure-response model predicted versus observed percentage of subjects with SVR12 in the clinical study described in Example 2A.

The model was also used to simulate the treatment described in Example 2A. The mean predicted versus observed percentage SVR ("% SVR") after 12-week treatment are shown FIG. 8. 95% confidence intervals for the predicted data (the vertical bar at the top of each respective predicted SVR percentage column) were also indicated. As shown in FIG. 8, the predicted SVR percentages aligned well with the observed SVR percentages. Simulations also predict that the same treatment regimen as described in Example 2A but without ribavirin has similar or comparable LOD percentages for different treatment durations.

The exposure response viral dynamic model of this Example provided a quantitative method to reasonably predict SVR for various combination of antiviral compounds. Based on the exposure-antiviral response modeling and clinical trial simulations, it demonstrated that (1) addition of a $3^{rd}$ DAA to a 2-DAA combination can reduce optimal duration of treatment and/or increase SVR; (2) 8-12 weeks of dosing is the optimal duration of therapy for 2 and 3 DAA combinations of Compound 1/r, Compound 2 and Compound 4; and (3) durations shorter than 8 weeks of interferon-free treatment have been predicted to cure a significant percent of the subjects.

Example 7

Clinical Modeling for Interferon-Free DAA Combination Therapies Containing BMS-790052 and BMS-650032

Figure 9:
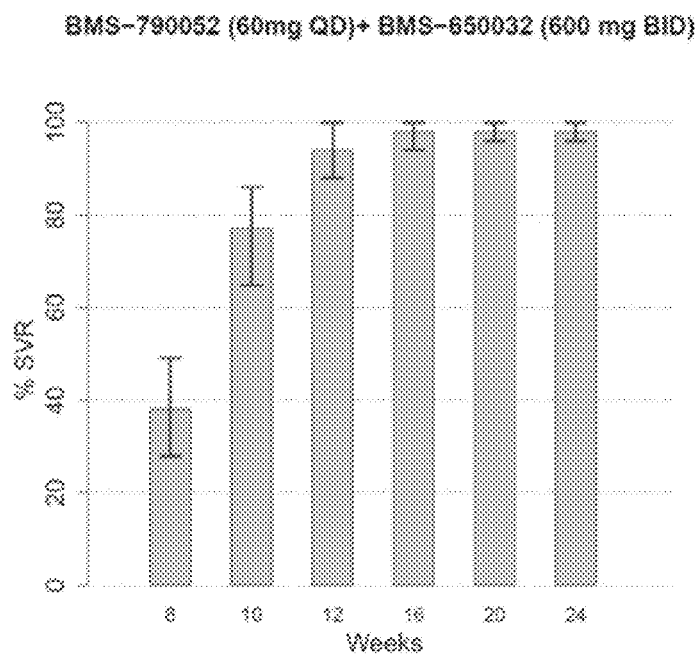
FIG. 9 shows the predicted median and 90% confidence interval of SVR rates for different treatment durations of a 2-DAA regimen containing BMS-790052 and BMS-650032.

The model described above was also used to predict the SVR percentage of interferon-free treatment regimens containing BMS-790052 and BMS-650032 without ribavirin, based on existing published clinical data including two Phase 1 and one Phase 2 study of BMS-790052 and one Phase 1 and one Phase 2a study of BMS-650032. FIG. 9 shows the predicted median SVR percentage and 90% SVR confidence interval for different treatment durations of a 2-DAA regimen containing BMS-790052 (60 mg QD) and BMS-650032 (600 BID) in genotype 1 naïve subjects. The combination of BMS-790052 (60 mg QD) plus BMS-650032 (600 mg BID) in genotype 1 subjects was predicted to achieve improved SVR for durations of 12 weeks or greater with predicted SVR rates of about 70% for 10 weeks of dosing. Similar regimens but containing ribavirin, or regimens with similar dosings of BMS-790052 and BMS-650032 with or without ribavirin, are expected to achieve similar SVR rates.

Example 8

Clinical Modeling for Interferon-Free Therapies Containing PSI-7977

Figure 10:
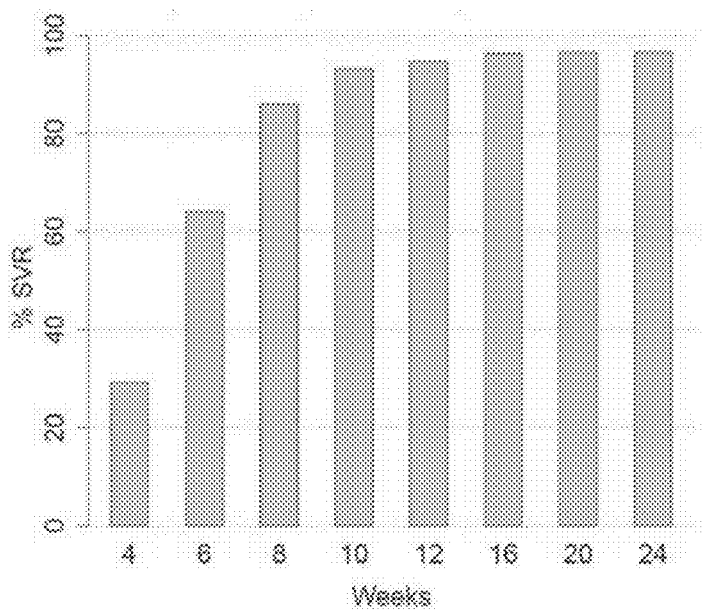
FIG. 10 shows the predicted median of SVR rates for different treatment durations of a 3-DAA regimen containing Compound 1/r, Compound 4 and PSI-7977.

Likewise, a 3-DAA regimen without interferon and ribavirin was modeled for genotype 1 patients based on existing clinical data. The 3-DAA regimen contains 200/100 mg QD Compound 1/r, 50 mg QD Compound 4, and 400 mg QD PSI-7977. FIG. 10 depicts the predicted median SVR rates for different treatment durations of this 3-DAA combination. This 3-DAA combination was predicted to have over 60% SVR in 6 weeks and over 80% SVR at duration of 8-week, 10-week, 12-week or longer treatment. Similar regimens but containing ribavirin, or regimens with similar dosings of Compound 1/r, Compound 4 and PSI-7977 with or without ribavirin, are expected to achieve similar SVR rates.

Figure 11:
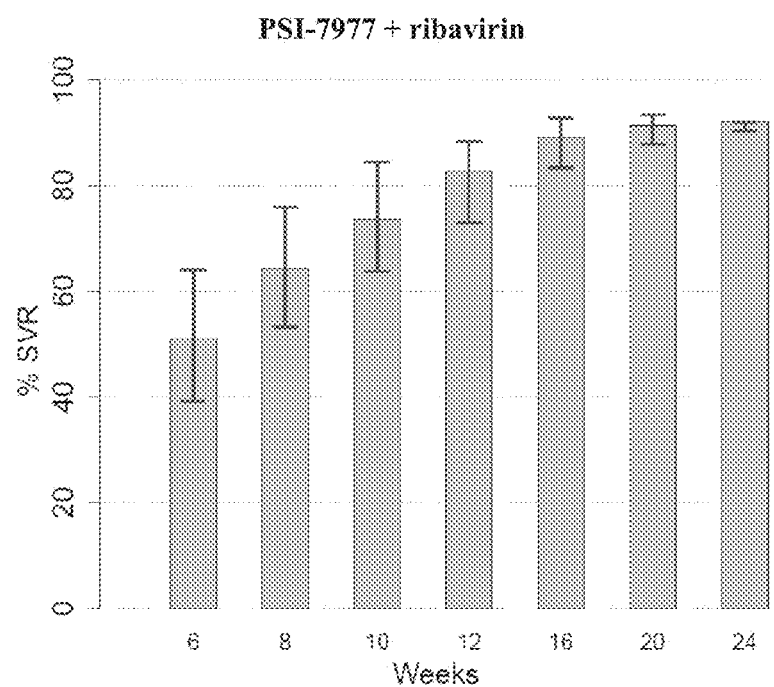
FIG. 11 shows the predicted median and 90% confidence interval of SVR percentage for different treatment durations of a 1-DAA regimen containing PSI-7977 and ribavirin.

The model can also be used to predict SVR for regimens containing single DAA or single DAA with ribavirin. For example, the model predictions for PSI-7977+ribavirin for various durations for treating HCV genotype 1 treatment-naïve patients were obtained. FIG. 11 depicts the predicted median and 90% confidence interval of SVR percentage for different treatment durations of such a regimen containing PSI-7977 (as the sole DAA; 400 mg QD) and ribavirin (600 mg BID). The 90% confidence interval for the predicted SVR (the vertical bar at the top of each respective predicted SVR percentage column) is also indicated in FIG. 11. The prediction was based on the already published clinical data for PSI-7977. SVR rate for PSI-7977+ribavirin was predicted to be around 75-90% following 12 weeks of dosing, and about 55-75% following 8 weeks dosing, in genotype 1 subjects. Similar SVR percentages for genotype 1 treatment-naïve patients are expected for similar regimens containing similar PSI-7977 QD dosing (e.g., 200-600 mg QD) and weight-based amounts of ribavirin (e.g., 1000 to 1200 mg divided twice daily).

Figure 12:
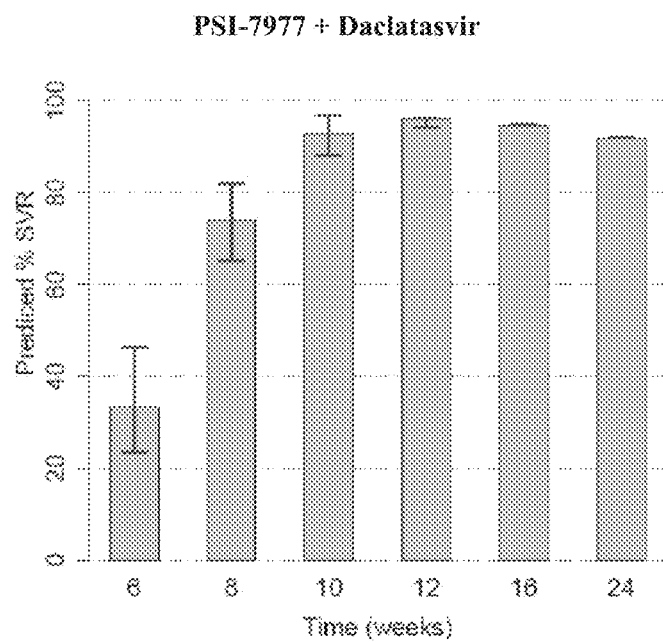
FIG. 12 depicts the predicted median and 90% confidence interval of SVR percentage for different treatment durations of a 2-DAA regimen containing daclatasvir (BMS-790052) 60 mg QD and PSI-7977 400 mg QD.

Data from two Phase 1 and one Phase 2 study of Daclatasvir (BMS-790052) and one Phase 1 and one Phase 2 study of PSI-7977 were used for estimating the pharmacokinetic and viral dynamic model parameters. Predictions for a 2-DAA combination with Daclatasvir (BMS-790052) and PSI-7977 in genotype 1 naïve patients are shown in FIG. 12. The model predicted that following 10-12 weeks of dosing with the combination of Daclatasvir and PSI-7977 without ribavirin, at least 90% of HCV genotype 1 naïve patients can achieve SVR. Similar or better SVR rates are predicted if ribavirin is included in the regimens.

Figure 13:
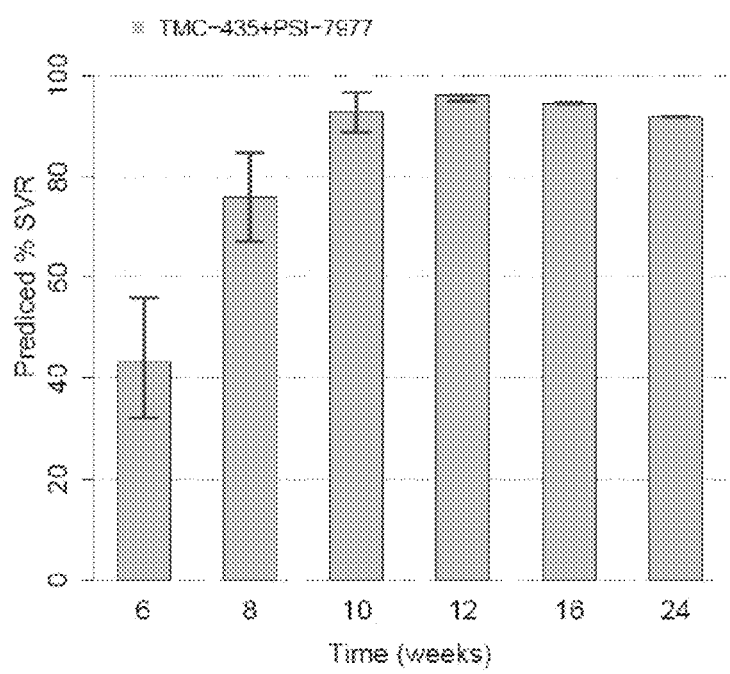
FIG. 13 shows the predicted median and 90% confidence interval of SVR percentage for different treatment durations of a 2-DAA regimen containing TMC-435 150 mg QD and PSI-7977 400 mg QD.

Similarly, data from one Phase 1a study of TMC-435 and one Phase 1 and one Phase 2 study of PSI-7977 were used for estimating the pharmacokinetic and viral dynamic model parameters. Predictions for a 2-DAA combination with the TMC-435 and PSI-7977 in genotype 1 naïve patients are shown in FIG. 13. The model predicts that following 10-12 weeks of dosing with the combination of TMC-435 and PSI-7977 without ribavirin, at least 90% of HCV patients can achieve SVR. Similar or better SVR rates are predicted if ribavirin is included in the regimens.

Example 9

Figure 14:
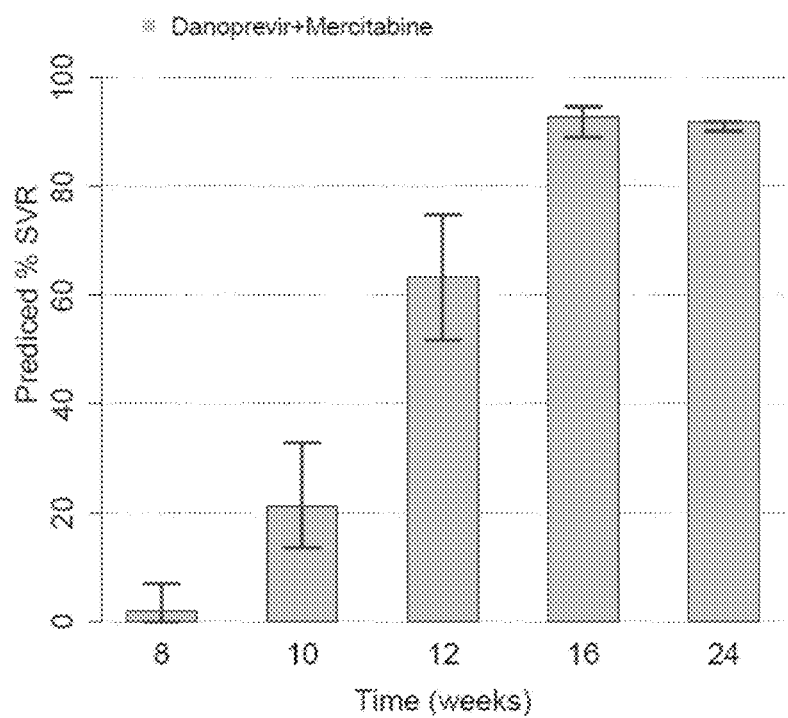
FIG. 14 illustrates the predicted median and 90% confidence interval of SVR percentage for different treatment durations of a 2-DAA regimen containing danoprevir 100 mg BID and mercitabine 750 mg BID.

Clinical Modeling for Interferon-Free DAA Combination Therapies Containing Danoprevir and Mercitabine In addition, data from one Phase 1 and one Phase 2 study of Danoprevir and Mercitabine were used for estimating the pharmacokinetic and viral dynamic model parameters. Ritonavir was co-administered with danoprevir to improve the pharmacokinetics of Danoprevir. Predictions for a 2-DAA combination with Danoprevir and Mercitabine in genotype 1 naïve patients are shown in FIG. 14. The model predicts that following 16 weeks of dosing with the combination of Danoprevir and Mercitabine without ribavirin, at least 90% of HCV patients can achieve SVR. Similar or better SVR rates are predicted if ribavirin is included in the regimens Example 10

Clinical Modeling for Interferon-Free DAA Combination Therapies Containing Tegobuvir (GS-9190), GS-9451 and GS-5885

Figure 15:
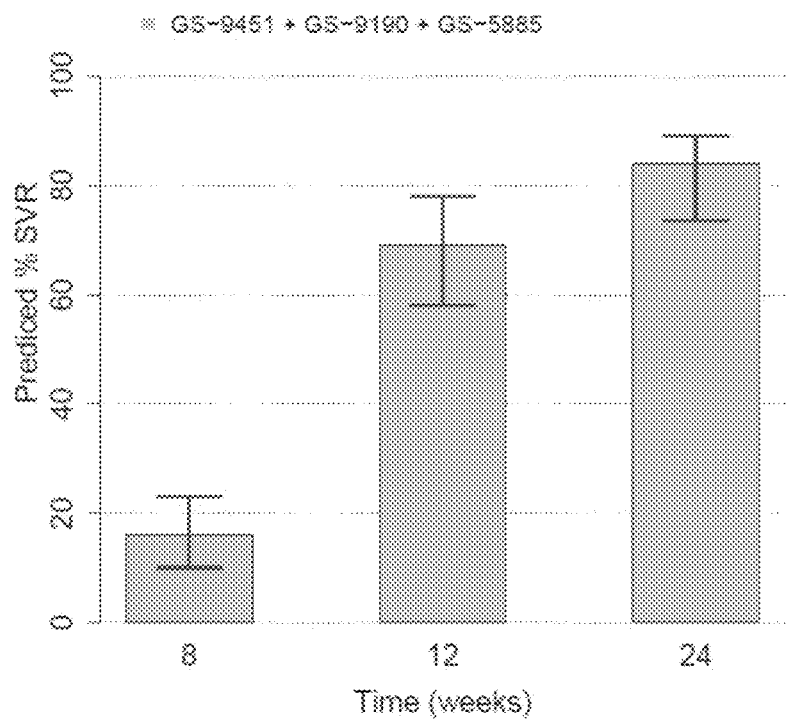
FIG. 15 depicts the predicted median and 90% confidence interval of SVR percentage for different treatment durations of a 2-DAA regimen containing GS-9190 (tegobuvir) 30 mg BID+GS-9451 200 mg QD+GS-5885 90 mg QD.

Data from Phase 1 and Phase 2 studies of GS-9190 (tegobuvir), GS-9451 and GS-5885 were used for estimating the pharmacokinetic and viral dynamic model parameters. Predictions for the combination with GS-9190 (tegobuvir), GS-9451 and GS-5885 in genotype 1 naive patients are shown in FIG. 15. The model predicts that following 12 weeks of dosing with the combination of GS-9190 (tegobuvir)+GS-9451+GS-5885+RBV, about 70% of genotype 1 naïve patients can achieve SVR and following 24 weeks of treatment >80% of genotype 1 naïve patients can achieve SVR. Similar or better SVR rates are expected when ribavirin is included in the regimen.

Example 11

Clinical Modeling for Interferon-Free DAA Combination Therapies Containing PSI-7977 (GS-7977)

Figure 16:
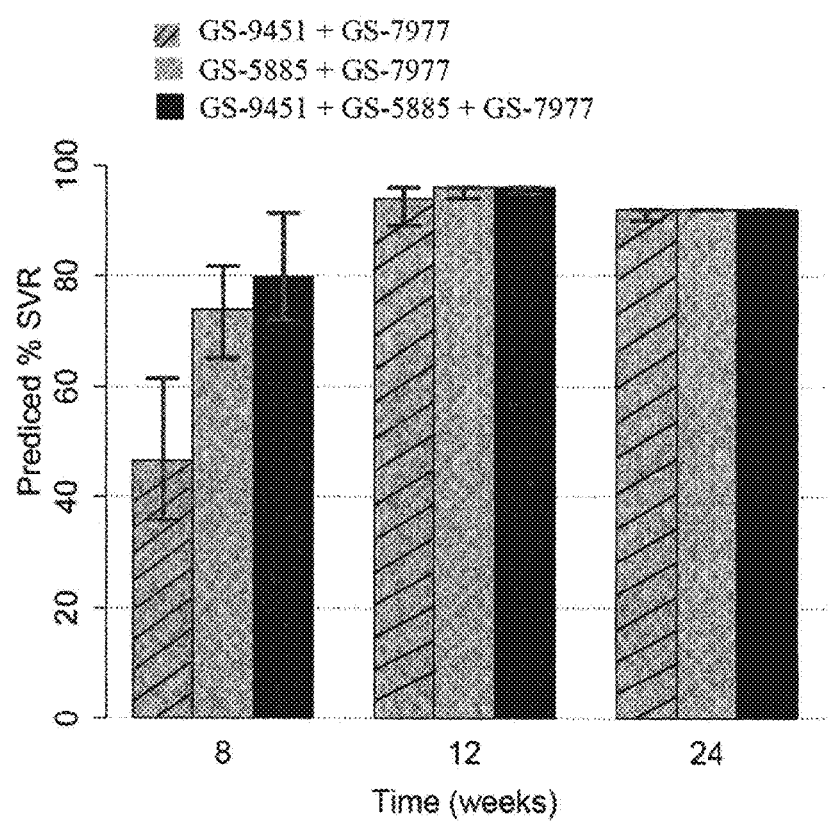
FIG. 16 shows the predicted median and 90% confidence interval of SVR percentage for different treatment durations of the following DAA combo regimens: (1) GS-9451 200 mg QD+GS-7977 (PSI-7977) 400 mg QD; (2) GS-5885 90 mg QD+GS-7977 (PSI-7977) 400 mg QD; and (3) GS-9451 200 mg QD+GS-5885 90 mg QD+GS-7977 (PSI-7977) 400 mg QD.

Data from Phase 1 and Phase 2 studies of GS-9451 and GS-7977 (PSI-7977) were used for estimating the pharmacokinetic and viral dynamic model parameters. Predictions for the combination with GS-9451 and GS-7977 (PSI-7977) in genotype 1 naive patients are shown in FIG. 16.

Data from Phase 1 and Phase 2 studies of GS-5885 and GS-7977 (PSI-7977) were used for estimating the pharmacokinetic and viral dynamic model parameters. Predictions for the combination with GS-5885 and GS-7977 (PSI-7977) in genotype 1 naive patients are shown in FIG. 16.

Data from Phase 1 and Phase 2 studies of GS-9451, GS-5885 and GS-7977 (PSI-7977) were used for estimating the pharmacokinetic and viral dynamic model parameters. Predictions for the combination with GS-9451, GS-5885 and GS-7977 (PSI-7977) in genotype 1 naive patients are shown in FIG. 16.

The model predicts that following 12 weeks of dosing with the combination of GS-9451 and GS-7977 (PSI-7977), or the combination of GS-5885 and GS-7977 (PSI-7977), or the combination of GS-9451, GS-5885 and GS-7977 (PSI-7977), at least 90% of genotype 1 naïve patients can achieve SVR. Similar or better SVR rates are expected when ribavirin is included in these regimens.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A method of treatment for HCV, comprising administering at least two direct acting antiviral agents (DAAs) to an HCV patient infected with HCV genotype 1, wherein said treatment does not include administration of interferon to said patient, and said treatment lasts for 12 weeks, and wherein said at least two DAAs comprise:

Compound 1 having formula of

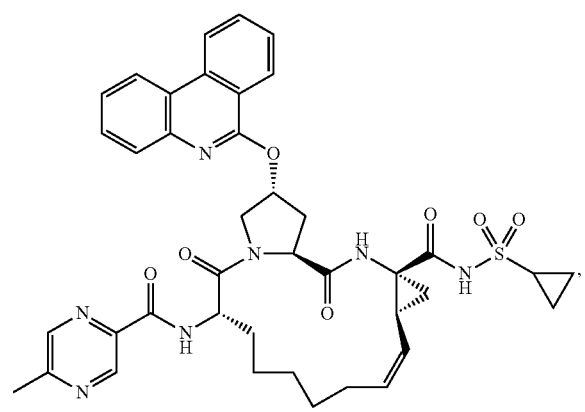 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

or a pharmaceutically acceptable salt thereof, and
Compound 4 having formula of

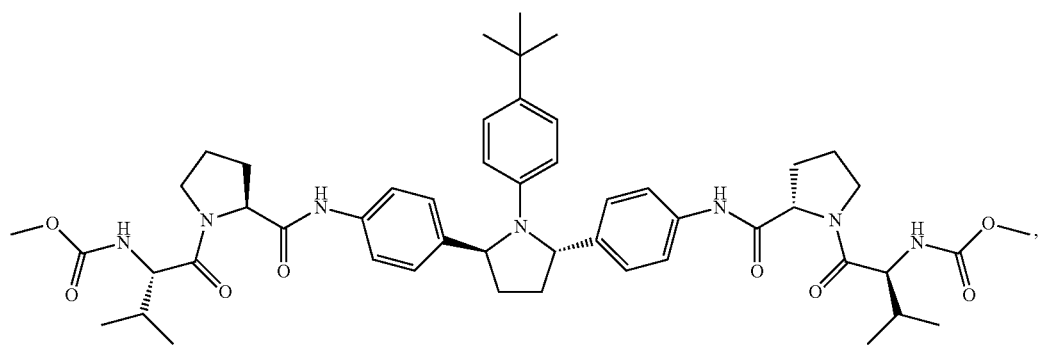

or a pharmaceutically acceptable salt thereof,
wherein Compound 1 or the salt thereof is co-administered with ritonavir.

2. The method of claim 1, wherein said patient is a treatment-naïve patient.

3. The method of claim 1, wherein said at least two DAAs further comprise compound 2 having formula of

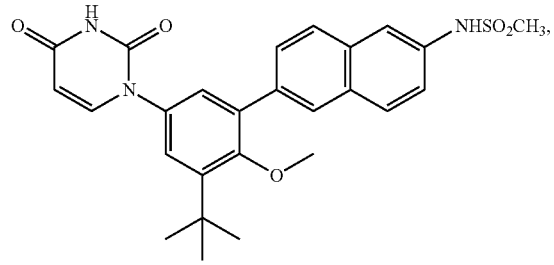

or a pharmaceutically acceptable salt thereof.

4. The method of claim 2, wherein said at least two DAAs further comprise compound 2 having formula of

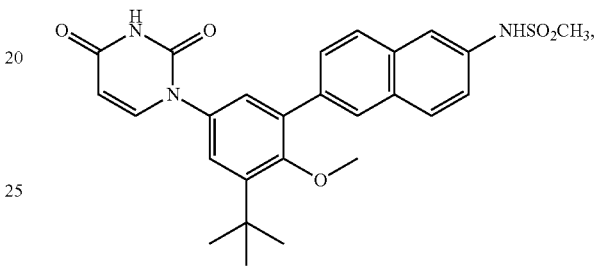

or a pharmaceutically acceptable salt thereof.

5. The method of claim 1, wherein said patient is infected with HCV genotype 1a.

6. The method of claim 2, wherein said patient is infected with HCV genotype 1a.

7. The method of claim 3, wherein said patient is infected with HCV genotype 1a.

8. The method of claim 4, wherein said patient is infected with HCV genotype 1a.

9. A method of treatment for HCV, comprising administering at least two direct acting antiviral agents (DAAs) and ribavirin to an HCV patient infected with HCV genotype 1, wherein said treatment does not include administration of interferon to said patient, wherein said at least two DAAs comprise PSI-7977 and TMC-435, and wherein said treatment lasts for 12 weeks.

10. The method of claim 9, wherein said patient is a treatment-naïve patient.

11. The method of claim 9, wherein said patient is infected with HCV genotype 1a.

12. The method of claim 10, wherein said patient is infected with HCV genotype 1a.

13. A method of treatment for HCV, comprising administering at least two direct acting antiviral agents (DAAs) and ribavirin to an HCV patient infected with HCV genotype 1, wherein said treatment does not include administration of interferon to said patient, wherein said at least two DAAs comprise PSI-7977 and GS-5885, and wherein said treatment lasts for 12 weeks.

14. The method of claim 13, wherein said patient is a treatment-naïve patient.

15. The method of claim 13, wherein said patient is infected with HCV genotype 1a.

16. The method of claim 14, wherein said patient is infected with HCV genotype 1a.

* * * * *